US009193697B2

(12) United States Patent
Yang et al.

(10) Patent No.: US 9,193,697 B2
(45) Date of Patent: Nov. 24, 2015

(54) OXAZOLE DERIVATIVES USEFUL AS MODULATORS OF FAAH

(75) Inventors: ZhiQiang Yang, Schwenksville, PA (US); Philippe G. Nantermet, Lansdale, PA (US); Constantine Kreatsoulas, Elkins Park, PA (US); Keith P. Moore, Bensalem, PA (US); Evan Foster Shalen, Mill Valey, CA (US)

(73) Assignee: MERCK SHARP & DOHME CORP., Rahway, NJ (US)

( * ) Notice: Subject to any disclaimer, the term of this patent is extended or adjusted under 35 U.S.C. 154(b) by 320 days.

(21) Appl. No.: 13/635,303

(22) PCT Filed: Apr. 4, 2011

(86) PCT No.: PCT/US2011/031040
§ 371 (c)(1),
(2), (4) Date: Sep. 14, 2012

(87) PCT Pub. No.: WO2011/126960
PCT Pub. Date: Oct. 13, 2011

(65) Prior Publication Data
US 2013/0018048 A1   Jan. 17, 2013

Related U.S. Application Data

(60) Provisional application No. 61/321,992, filed on Apr. 8, 2010.

(51) Int. Cl.
| | | |
|---|---|---|
| C07D 263/46 | (2006.01) |
| C07D 413/14 | (2006.01) |
| C07D 413/04 | (2006.01) |
| A61K 31/444 | (2006.01) |
| A61K 31/4545 | (2006.01) |
| A61K 31/4439 | (2006.01) |
| A61K 31/5377 | (2006.01) |
| A61K 31/496 | (2006.01) |
| A61K 31/437 | (2006.01) |
| A61K 31/422 | (2006.01) |
| A61K 31/541 | (2006.01) |
| A61K 31/433 | (2006.01) |
| A61K 31/4245 | (2006.01) |
| A61K 31/427 | (2006.01) |
| A61K 31/421 | (2006.01) |
| A61P 19/02 | (2006.01) |
| A61P 29/00 | (2006.01) |
| A61P 25/00 | (2006.01) |
| A61P 25/06 | (2006.01) |
| A61P 25/20 | (2006.01) |
| A61P 25/28 | (2006.01) |
| A61P 25/16 | (2006.01) |
| C07D 471/04 | (2006.01) |
| C07D 491/08 | (2006.01) |
| C07D 417/14 | (2006.01) |
| C07D 487/04 | (2006.01) |
| A61K 31/506 | (2006.01) |

(52) U.S. Cl.
CPC ............ *C07D 263/46* (2013.01); *C07D 413/04* (2013.01); *C07D 413/14* (2013.01)

(58) Field of Classification Search
CPC ... C07D 263/46; C07D 413/14; C07D 413/04
USPC .............. 514/227.8, 376, 333, 318, 274, 340, 514/236.8, 253.1, 300, 303, 275, 254.02, 514/363, 364, 365; 548/228, 138, 143, 200; 546/256, 194, 271.4, 113, 119; 544/316, 131, 364, 331, 369, 137, 58.2
See application file for complete search history.

(56) References Cited

FOREIGN PATENT DOCUMENTS

| | | |
|---|---|---|
| WO | WO2007140005 | 12/2007 |
| WO | WO2009071753 | 6/2009 |
| WO | WO2009152025 A1 | 12/2009 |
| WO | WO2010017079 A1 | 2/2010 |
| WO | WO 2010017079 A1 * | 2/2010 |

OTHER PUBLICATIONS

Pacher, et al, The Endocannabinoid System as an Emerging Target of Pharmacotherapy, Pharmacological Reviews, 2006, 389-362, 58.

* cited by examiner

*Primary Examiner* — Sreeni Padmanabhan
*Assistant Examiner* — Jason A Deck
(74) *Attorney, Agent, or Firm* — Matthew A. Leff; John C. Todaro

(57) ABSTRACT

The present invention is directed to certain Oxazole derivatives which are useful as modulators of Fatty Acid Amide Hydrolase (FAAH) and as FAAH imaging agents. The invention is also concerned with pharmaceutical formulations comprising these compounds as active ingredients and the use of the compounds and their formulations in the treatment of certain disorders, including osteoarthritis, rheumatoid arthritis, diabetic neuropathy, postherpetic neuralgia, skeletomuscular pain, and fibromyalgia, as well as acute pain, migraine, sleep disorder, Alzheimer Disease, and Parkinson's Disease.

4 Claims, No Drawings

SEQUENCE LISTING

<160> NUMBER OF SEQ ID NOS: 3

<210> SEQ ID NO 1
<211> LENGTH: 36
<212> TYPE: DNA
<213> ORGANISM: Unknown
<220> FEATURE:
<223> OTHER INFORMATION: Primer

<400> SEQUENCE: 1
caaggtaccg ccaccatggt gctgagcgaa gtgtgg        36

<210> SEQ ID NO 2
<211> LENGTH: 30
<212> TYPE: DNA
<213> ORGANISM: Unknown
<220> FEATURE:
<223> OTHER INFORMATION: Primer

<400> SEQUENCE: 2
ccggaattct caagatggcc gcttttcagg        30

<210> SEQ ID NO 3
<211> LENGTH: 30
<212> TYPE: DNA
<213> ORGANISM: Unknown
<220> FEATURE:
<223> OTHER INFORMATION: Primer

```
<400> SEQUENCE: 3
ccggaattct cacgatggct gcttttgagg         30
```

OXAZOLE DERIVATIVES USEFUL AS MODULATORS OF FAAH

BACKGROUND OF THE INVENTION

Disclosed herein are compounds that inhibit the activity of fatty acid amide hydrolase (FAAH), compositions that include the compounds, and methods of their use. Compounds disclosed herein as inhibitors of fatty acid amide hydrolase (FAAH) are useful in the treatment of diseases, disorders, or conditions that would benefit from the inhibition of fatty acid amide hydrolase and increases in endogenous fatty acid amides.

Fatty acid amide hydrolase (FAAH) is an enzyme that is abundantly expressed throughout the CNS (Freund et al. Physiol. Rev. 2003; 83:1017-1066) as well as in peripheral tissues, such as, for example, in the pancreas, brain, kidney; skeletal muscle, placenta, and liver (Giang, D. K. et al., Proc. Natl. Acad. Sci. U.S.A. 1997, 94, 2238-2242; Cravatt et al. Proc. Natl. Acad. Sci. U.S.A. 2004, 101, 29, 10821-10826). FAAH hydrolyzes the fatty acid amide (FAA) family of endogenous signaling lipids. General classes of fatty acid amides include the N-acylethanolamides (NAEs) and fatty acid primary amides (FAPAs). Examples of NAEs include anandamide (AEA), palmitoylethanolamide (PEA) and oleoylethanolamide (OEA). An example of FAPAs includes 9-Z-octadecenamide or oleamide. (McKinney M K and Cravatt B F 2005. Annu Rev Biochem 74:411-32). Another class of fatty acid amide family of endogenous signaling lipids is N-acyl taurines that have also been shown to be elevated upon FAAH deletion or inhibition and appear to act on transient receptor potential (TRP) family of calcium channels, although the functional consequences are not yet clear (Saghatelian A, et al. Biochemistry. 2004, 43:14332-9, Saghatelian A, et al. Biochemistry, 2006, 45:9007-9015). In addition to fatty acid amides, FAAH can also hydrolyze certain fatty acid esters, such as, for example, 2-arachidonylglycerol (2-AG) another endocannabinoid (Mechoulam et al. Biochem. Pharmacol. 1995; 50:83-90; Stella et al. Nature, 1997; 388:773-778; Suguria et al. Biochem. Biophys. Res. Commun. 1995; 215:89-97).

Inhibition of FAAH is expected to lead to an increase in the level of anandamide and other fatty acid amides. This increase in fatty acid amides leads to an increase in the noiceptive threshold. Thus, inhibitors of FAAH are useful in the treatment of pain (Cravatt, B F; Lichtman, A H Current Opinion in Chemical Biology 2003, 7, 469-475). Such inhibitors are useful in the treatment of other disorders that can be treated using fatty acid amides or modulators of cannabinoid receptors, such as, for example, anxiety, sleep disorder, Alzheimer disease, and Parkinson's disease, eating disorders, metabolic disorders, cardiovascular disorders, and inflammation (Simon et al Archives of Gen. Psychiatry, 2006, 63, 824-830. Kunos, G et al. *Pharmacol Rev* 2006, 58, 389-462). In some embodiments, FAAH inhibitor compounds may be peripherally restricted and may not substantially affect neural disorders, such as, for example, depression and anxiety. Finally, agonism of cannabinoid receptors has also been shown to reduce the progression of atherosclerosis in animal models (see Steffens et al. Nature, 2005, 434, 782-786; and Steffens et al., Curr Opin. Lipid., 2006, 17, 519-526). Thus, increasing the level of endogenous cannabinergic fatty acid amides (e.g., anandamide) is expected to effectively treat or reduce the risk of developing atherosclerosis.

Inhibition of FAAH also leads to elevation of palmitoylethanolamide which is thought to work, in part, through activation of the peroxisome proliferator-activated receptor α (PPAR-α) to regulate multiple pathways including, for example, pain perception in neuropathic and inflammatory conditions such as convulsions, neurotoxicity, spacticity and to reduce inflammation, for example, in atopic eczema and arthritis (LoVerme J et al. The nuclear receptor peroxisome proliferator-activated receptor-alpha mediates the anti-inflammatory actions of palmitoylethanolamide. *Mol Pharmacol* 2005, 67, 15-19; LoVerme J et al. The search for the palmitoylethanolamide receptor. *Lift Sci* 2005, 77: 1685-1698. Lambert D M et al. The palmitoylethanolamide family: a new class of anti-inflammatory agents? *Curr Med Chem* 2002, 9: 663-674; Eberlein B, et al. Adjuvant treatment of atopic eczema: assessment of an emollient containing N-palmitoylethanolamine (ATOPA study). J Eur Acad Dermatol Venereol. 2008, 22:73-82. Re G, et al. Palmitoylethanolamide, endocannabinoids and related cannabimimetic compounds in protection against tissue inflammation and pain: potential use in companion animals. Vet J. 2007 173: 21-30.). Thus, inhibition of FAAH is useful for the treatment of various pain and inflammatory conditions, such as osteoarthritis, rheumatoid arthritis, diabetic neuropathy, postherpetic neuralgia, skeletomuscular pain, and fibromyalgia.

It is also thought that certain fatty acid amides, such as, for example, OEA, act through the peroxisome proliferator-activated receptor α (PPAR-α) to regulate diverse physiological processes, including, e.g., feeding and lipolysis. Consistent with this, human adipose tissue has been shown to bind and metabolize endocannabinoids such as anandamide and 2-arachidonylglycerol (see Spoto et al., Biochimie 2006, 88, 1889-1897; and Matias et al., J. Clin. Endocrin. & Met., 2006, 91, 3171-3180). Thus, inhibiting FAAH activity in vivo leads to reduced body fat, body weight, caloric intake, and liver triglyceride levels. However, unlike other anti-lipidemic agents that act through PPAR-α, e.g., fibrates, FAAH inhibitors do not cause adverse side effects such as rash, fatigue, headache, erectile dysfunction, and, more rarely, anemia, leukopenia, angioedema, and hepatitis (see, e.g., Muscari, et al., Cardiology, 2002, 97:115-121).

Many fatty acid amides are produced on demand and rapidly degraded by FAAH. As a result, hydrolysis by FAAH is considered to be one of the essential steps in the regulation of fatty acid amide levels in the central nervous system as well as in peripheral tissues and fluids. The broad distribution of FAAH combined with the broad array of biological effects of fatty acid amides (both endocannabinoid and non-endocannabinoid mechanisms) suggests that inhibition of FAAH leads to altered levels of fatty acid amides in many tissues and fluids and may be useful to treat many different conditions. FAAH inhibitors increase the levels of endogenous fatty acid amides. FAAH inhibitors block the degradation of endocannabinoids and increase the tissue levels of these endogenous substances. FAAH inhibitors can be used in this respect in the prevention and treatment of pathologies in which endogenous cannabinoids and or any other substrates metabolized by the FAAH enzyme are involved.

The various fatty acid ethanolamides have important and diverse physiological functions. As a result, inhibitor molecules that selectively inhibit FAAH enzymatic activity would allow a corresponding selective modulation of the cellular and extra-cellular concentrations of a FAAH substrate. FAAH inhibitors that are biologically compatible could be effective pharmaceutical compounds when formulated as therapeutic agents for any clinical indication where FAAH enzymatic inhibition is desired. In some embodiments, FAAH activity in peripheral tissues can be preferentially inhibited. In some embodiments, FAAH inhibitors that do substantially cross the blood-brain-barrier can be used to preferentially inhibit FAAH activity in peripheral tissues. In some embodiments, FAAH inhibitors that preferentially inhibit FAAH activity in peripheral tissues can minimize the effects of FAAH inhibition in the central nervous system. In some embodiments, it is preferred to inhibit FAAH activity in peripheral tissues and minimize FAAH inhibition in the central nervous system.

SUMMARY OF THE INVENTION

The present invention is directed to certain Oxazole derivatives which are useful as inhibitors of Fatty Acid Amide Hydrolase (FAAH). The invention is also concerned with pharmaceutical formulations comprising these compounds as active ingredients and the use of the compounds and their formulations in the treatment of certain disorders, including osteoarthritis, rheumatoid arthritis, diabetic neuropathy, postherpetic neuralgia, skeletomuscular pain, and fibromyalgia, as well as acute pain, migraine, sleep disorder, Alzheimer disease, and Parkinson's disease.

DETAILED DESCRIPTION OF THE INVENTION

In one aspect the invention is directed to compounds of formula I:

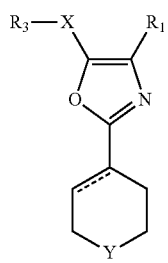

I or a pharmaceutically acceptable salt thereof wherein:
wherein n is 0, 1 or 2;
X is selected from S, O, and $CR_aR_b$;
Y is selected from, O, $NR_c$, and $CR_dR_e$,
$R_a$ and $R_b$ are each independently selected from the group consisting of hydrogen and methyl;
$R_c$ is selected from $C_{1-4}$alkyl, C(=O)R and C(=O)OR and $SO_2R$;
R is selected from
  (1) hydrogen,
  (2) $C_{1-4}$alkyl, optionally substituted with $NH_2$, wherein the $NH_2$ is optionally substituted with $C_{1-3}$alkyl or hydroxy$C_{1-3}$alkyl,
  (3) methoxy$C_{1-4}$alkyl,
  (4) methoxy$C_{1-4}$alkyloxy$C_{1-4}$alkyl,
  (5) $HET^4$
  (6) —$C_{1-2}$alkyl-$HET^4$,
  (7) aryl, and
  (8) —$C_{1-2}$alkyl aryl,
wherein the aryl and HET of choices (5) to (8) are optionally substituted with hydroxyl, methyl, methoxy or halo;
$R_d$ and $R_e$ are each independently selected from the group consisting of hydrogen, hydroxyl, C(O)R', C(O)—O—R, C(=O)NR'R", methyl and hydroxymethyl;
R' and R" are each independently selected from hydrogen and methyl;

$R_1$ is selected from the group consisting of:
  (1) aryl,
  (2) $HET^1$, and
  (3) $C_{3-6}$cycloalkyl,
wherein $R_1$ is optionally mono or di-substituted with substituents $R^4$ and $R^5$; and wherein $R^4$ and $R^5$ are independently selected from the group consisting of:
  (a) halo,
  (b) —CN,
  (c) mono, di or tri-halo $C_{1-4}$ alkyl,
  (d) mono, di or tri-halo $OC_{1-4}$ alkyl,
  (e) —$OC_{1-4}$ alkyl, optionally substituted with hydroxyl, halo or amino,
  (f) —$C_{1-4}$alkyl optionally substituted with one or two substituents selected from hydroxyl, CN, —$CHF_2$ and —$CF_3$,
  (g) —$C_{1-2}$alkyl-$C_{3-6}$cycloalkyl optionally substituted with hydroxy, halo or CN,
  (h) —$S(O)_nC_{1-4}$alkyl,
  (i) —$S(O)_nNR^6R^7$,
  (j) —C(O)—NH—$NR^8R^9$,
  (k) —C(O)—OH,
  (l) —C(O)—$OC_{1-4}$alkyl, optionally substituted with halo, hydroxy, phenyl or methoxy, wherein the phenyl is optionally substituted with halo, hydroxy, phenyl or methoxy,
  (m) —C(O)—O-aryl,
  (n) —C(O)—$NR^{10}R^{11}$,
  (o) —C(O)—$N(R^{10})HET^2$,
  (p) —C(O)—$C_{1-4}$alkyl optionally mono, di or tri substituted with halo,
  (q) —$C(NR^{12})$—$NR^{13}R^{14}$,
  (r) $HET^2$,
  (s) —$CH_2$—$HET^2$,
  (t) —C(O)—$HET^2$
  (u) —$CH(CH_3)$—$HET^2$
  (v) aryl,
  (w) —C(O)—NH—NH—C(O)H,
  (x) —$CH_2$—C(O)—O—$C_{1-4}$alkyl, whereas the $CH_2$ may be optionally substituted with $C_{1-4}$alkyl or hydroxyl,
  (y) —$CH_2$—$C(O)NR^{15}R^{16}$, whereas the $CH_2$ may be optionally substituted with $C_{1-4}$alkyl or hydroxy,
  (z) —$NR^{17}R^{18}$, and
  (aa) hydroxyl,
wherein the aryl or HET of choices (m), (o), (r), (s), (t), (u) and (v) are each optionally mono or di-substituted with substituents selected from
  (1) halo,
  (2) —CN,
  (3) —OH,
  (4) —$C_{1-4}$alkyl optionally substituted with hydroxy, halo or cyano,
  (5) —$CF_3$,
  (6) —$OC_{1-4}$alkyl optionally substituted with hydroxyl or halo,
  (7) —C(O)OH, and
  (8) —C(O)O—$C_{1-3}$alkyl;
  (9) —C(O)—$NR^{19}R^{20}$,
  (10) —$NH_2$,
  (11) Oxo,
  (12) =S,
wherein $R^6$, $R^7$, $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$ and $R^{20}$, are each independently selected from H and $C_{1-4}$alkyl,
or
$R^6$ and $R^7$ or $R^8$ and $R^9$ or $R^{10}$ and $R^{11}$ or $R^{13}$ and $R^{14}$ or $R^{15}$ and $R^{16}$ or $R^{17}$ and $R^{18}$ or $R^{19}$ and $R^{20}$ are joined together to form a ring with the atoms to which they are attached there is formed a 5-membered heterocyclic ring of 4 to 7 atoms, said ring containing 1, 2, 3 or 4 heteroatoms selected from N, O and S, said ring being optionally mono or di-substituted with substituents independently selected from halo, hydroxyl, oxo, $C_{1-4}$alkyl, hydroxy$C_{1-4}$alkyl, halo$C_{1-4}$alkyl, —C(O)—$C_{1-4}$alkyl and —S(O)n$C_{1-4}$alkyl;

$R_3$ is selected from the group consisting of:
(1) aryl, and
(2) HET$^3$, wherein $R_3$ is optionally mono or di-substituted with substituents independently selected from the group consisting of:
(a) hydroxy,
(b) halo,
(c) —$C_{3-6}$cycloalkyl,
(d) —O$C_{3-6}$cycloalkyl,
(e) $C_{1-4}$ alkyl,
(f) —O$C_{1-4}$ alkyl,
(g) —C(O)CH$_3$,
(h) mono, di or tri-halo $C_{1-4}$ alkyl,
(i) mono, di or tri-halo —O$C_{1-4}$ alkyl, and
(j) —S(O)$_n$—$C_{1-4}$alkyl;

wherein aryl is as a mono- or hi-cyclic aromatic ring system; and HET$^1$, HET$^2$, HET$^3$ and HET$^4$ are each independently a 5 to 10-membered aromatic, partially aromatic or non-aromatic mono- or bicyclic ring, or N-oxide thereof, said containing 1 to 4 heteroatoms selected from O, S and N, and optionally substituted with 1 to 2 oxo groups.

Within this aspect there is a genus
wherein:
$R_1$ is selected from the group consisting of:
(1) phenyl,
(2) pyridyl,
(3) pyridazinyl,
(4) pyrimidyl,
(5) pyrazinyl,
(6) piperidinyl,
(7) thiazolyl,
(8) thienyl,
(9) pyrrolyl,
(10) indazolyl,
(11) pyrazololpyridinyl,
(12) pyrrolopyridinyl,
(13) pyrroloimidazolyl,
(14) pyrazolyl,
(15) triazolopyridinyl, and
(16) benzotriazolyl, wherein $R_1$ is optionally mono or di-substituted with substituents $R^4$ and $R^5$; and wherein $R^4$ and $R^5$ are independently selected from the group consisting of:
(a) halo,
(b) mono, di or tri-halo $C_{1-4}$ alkyl,
(c) mono, di or tri-halo O$C_{1-4}$ alkyl,
(d) —O$C_{1-4}$ alkyl, optionally substituted with halo or amino,
(e) —$C_{1-4}$alkyl optionally substituted with one or two substituents selected from hydroxyl, —CHF$_2$ and —CF$_3$,
(f) —$C_{1-2}$alkyl-$C_{3-6}$cycloalkyl optionally substituted with hydroxy, halo or CN,
(g) —S(O)$_n$$C_{1-4}$alkyl,
(h) —S(O)$_n$NR$^6$R$^7$,
(i) —C(O)—O$C_{1-4}$alkyl, optionally substituted with halo, hydroxy, phenyl or methoxy, wherein the phenyl is optionally substituted with halo, hydroxy, phenyl or methoxy,
(j) —C(O)—O-aryl,
(k) —C(O)—NR$^{10}$R$^{11}$,
(l) —C(O)—N(R$^{10}$)HET$^2$,
(m) —C(O)—$C_{1-4}$alkyl optionally mono, di or tri substituted with halo,
(n) HET$^2$,
(o) —CH$_2$—HET$^2$,
(p) —C(O)—HET$^2$
(q) —CH(CH$_3$)—HET$^2$
(r) aryl,
(s) —CH$_2$—C(O)—O—$C_{1-4}$alkyl, whereas the CH$_2$ may be optionally substituted with $C_{1-4}$alkyl or hydroxyl,
(t) —CH$_2$—C(O)NR$^{15}$R$^{16}$, whereas the CH$_2$ may be optionally substituted with $C_{1-4}$alkyl or hydroxy,
(u) —NR$^{17}$R$^{18}$, and
(v) hydroxyl, wherein the aryl or HET of choices (j), (l), (n), (O), (p), (q) and (r) are each optionally mono or di-substituted with substituents selected from
(1) halo,
(3) —OH,
(4) —$C_{1-4}$alkyl optionally substituted with hydroxy, halo or cyano,
(5) —CF$_3$,
(6) —O$C_{1-4}$alkyl optionally substituted with hydroxyl or halo,
(7) —C(O)OH, and
(8) —C(O)O—$C_{1-3}$alkyl;
(9) —C(O)—NR$^{19}$R$^{20}$,
(10) —NH$_2$,
(11) Oxo,
(12) =S, wherein R$^6$, R$^7$, R$^8$, R$^9$, R$^{10}$, R$^{11}$, R$^{12}$, R$^{13}$, R$^{14}$, R$^{15}$, R$^{16}$, R$^{17}$, R$^{18}$, R$^{19}$ and R$^{20}$, are each independently selected from H and $C_{1-4}$alkyl, Within this genus there is a sub-genus
wherein:
$R_1$ is selected from the group consisting of:
(1) phenyl,
(2) pyridyl,
(3) pyrimidyl,
(4) pyrazinyl,
(5) pyridazinyl,
(6) piperidinyl,
(7) indazolyl, optionally mono or di-substituted with substituents $R^4$ and $R^5$, which are independently selected from the group consisting of
(a) mono, di or tri-halo $C_{1-4}$ alkyl,
(b) —$C_{1-4}$alkyl optionally substituted with one or two substituents selected from hydroxyl, —CHF$_2$ and —CF$_3$,
(c) —S(O)$_n$$C_{1-4}$alkyl,
(d) —C(O)—NR$^{10}$R$^{11}$,
(e) HET$^2$, wherein HET$^2$ is optionally mono or di-substituted with substituents selected from:
(1) halo,
(2) —CN,
(3) —OH,
(4) —$C_{1-4}$alkyl optionally substituted with hydroxy, halo or cyano,
(5) —CF$_3$,
(6) —O$C_{1-4}$alkyl optionally substituted with hydroxyl or halo,
(7) —C(O)OH, and
(8) —C(O)O—$C_{1-3}$alkyl, and
(9) —C(O)—NR$^{19}$R$^{20}$, wherein R$^{10}$, R$^{11}$, R$^{19}$ and R$^{20}$ are each independently selected from H and $C_{1-4}$alkyl.

Within this sub-genus there is a class
wherein
HET² is optionally mono or di-substituted with substituents selected from:
(1) halo,
(2) —OH,
(3) —C$_{1-4}$alkyl optionally substituted with hydroxy, halo or cyano,
(4) —CF$_3$,
(5) —OC$_{1-4}$alkyl optionally substituted with hydroxyl or halo, and
(6) —C(O)O—C$_{1-3}$alkyl.
Within this aspect there is a genus
wherein:
X is S.
Within this genus there is a sub-genus
wherein:
Y is selected from, O and CR$_d$R$_e$, wherein
R$_d$ and R$_e$ are each independently selected from the group consisting of hydrogen, hydroxyl, C(O)R', C(O)—O—R', C(=O)NR'R", methyl and hydroxymethyl;
R' and R" are each independently selected from hydrogen and methyl;
Within this sub-genus there is a class
wherein:
Y is O.
Within this aspect there is a genus
wherein:
R$_3$ is selected from the group consisting of
(1) aryl, and
(2) HET³,
wherein choice (1) and (2) are each optionally mono or di-substituted with substituents independently selected from the group consisting of:
(a) halo,
(b) —C$_{3-6}$cycloalkyl,
(c) —OC$_{1-4}$ alkyl,
(d) mono, di or tri-halo C$_{1-4}$ alkyl, and
(e) mono, di or tri-halo —OC$_{1-4}$ alkyl.
Within this sub-genus there is class
wherein
R$_3$ is selected from the group consisting of:
(1) phenyl,
(2) pyrimidinyl,
(3) pyridyl,
wherein R$_3$ is optionally mono or di-substituted with halo, haloC$_{1-4}$alkyl, or —OC$_{1-4}$alkyl optionally substituted with halo.
Within this aspect there is a genus of compounds of Formula

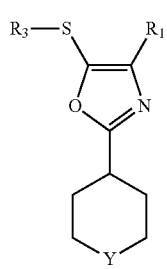

Ia wherein
R$_1$ is selected from the group consisting of: (we will use claim 3 definitional here)
wherein R⁶, R⁷, R¹⁰, R¹¹, R¹⁹ and R²⁰, are each independently selected from H and C$_{1-4}$alkyl;
Y is selected from, O and CR$_d$R$_e$, and
R$_3$ is selected from the group consisting of:
(1) aryl, and
(2) HET⁵,
wherein choice (1) and (2) are each optionally mono or di-substituted with substituents independently selected from the group consisting of
(a) halo,
(b) —C$_{3-6}$cycloalkyl,
(c) —C$_{1-4}$ alkyl,
(d) —OC$_{1-4}$ alkyl,
(e) mono, di or tri-halo C$_{1-4}$ alkyl, and
(f) mono, di or tri-halo —OC$_{1-4}$ alkyl.
Within this genus there is a sub-genus of compounds of the Formula

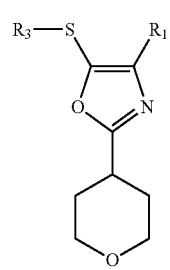

Ib wherein:
R$_1$ is selected from the group consisting of:
(1) phenyl,
(2) pyridyl,
(3) pyrimidyl,
(4) pyrazinyl,
(5) pyridazinyl,
(6) piperidinyl,
(7) indazolyl,
optionally mono or di-substituted with substituents R⁴ and R⁵, which are independently selected from the group consisting of
(a) mono, di or tri-halo C$_{1-4}$ alkyl,
(b) —C$_{1-4}$alkyl optionally substituted with one or two substituents selected from hydroxyl, —CHF$_2$ and —CF$_3$,
(c) —S(O)$_n$C$_{1-4}$alkyl,
(d) —C(O)—NR¹⁰R¹¹,
(e) HET²,
wherein HET² is optionally mono or di-substituted with substituents selected from:
(1) halo,
(2) —CN,
(3) —OH,
(4) —C$_{1-4}$alkyl optionally substituted with hydroxy, halo or cyano,
(5) —CF$_3$,
(6) —OC$_{1-4}$alkyl optionally substituted with hydroxyl or halo,
(7) —C(O)OH, and
(8) —C(O)O—C$_{1-3}$alkyl, and
(9) —C(O)—NR¹⁹R²⁰, wherein $R^{10}$, $R^{11}$, $R^{19}$ and $R^{20}$ are each independently selected from H and $C_{1-4}$alkyl; and $R_3$ is selected from the group consisting of:
(1) aryl, and
(2) $HET^3$,
wherein choice (1) and (2) are each optionally mono or di-substituted with substituents independently selected from the group consisting of:
(a) halo,
(b) —$C_{3-6}$cycloalkyl,
(c) —$OC_{1-4}$ alkyl,
(d) mono, di or tri-halo $C_{1-4}$ alkyl, and
(e) mono, di or tri-halo —$OC_{1-4}$ alkyl.

Within this sub-genus there is a class of compounds of Formula

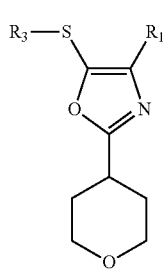

Ib wherein:
$R_1$ is selected from the group consisting of
(1) phenyl,
(2) pyridyl,
(3) pyrimidyl,
(4) pyrazinyl,
(5) pyridazinyl,
(6) piperidinyl,
(7) indazolyl,
optionally mono or di-substituted with substituents $R^4$ and $R^5$, which are independently selected from the group consisting of
(a) mono, di or tri-halo $C_{1-4}$ alkyl,
(b) —$C_{1-4}$alkyl optionally substituted with one or two substituents selected from hydroxyl, —$CHF_2$ and —$CF_3$,
(c) —$S(O)_nC_{1-4}$alkyl,
(d) —C(O)—$NR^{10}R^{11}$,
(e) $HET^2$,
wherein $HET^2$ is optionally mono or di-substituted with substituents selected from:
(1) halo,
(2) —OH,
(3) —$C_{1-4}$alkyl optionally substituted with hydroxy, halo or cyano,
(4) —$CF_3$,
(5) —$OC_{1-4}$alkyl optionally substituted with hydroxyl or halo, and
(6) —C(O)O—$C_{1-3}$alkyl; and $R_3$ is selected from the group consisting of:
(1) phenyl,
(2) pyrimidinyl,
(3) pyridyl,
wherein $R_3$ is optionally mono or di-substituted with halo, halo$C_{1-4}$alkyl, or —$OC_{1-4}$alkyl optionally substituted with halo.

In another aspect, the invention is directed to pharmaceutical compositions which comprise an inert carrier and a compound of Formula I or a pharmaceutically acceptable salt thereof.

In another aspect, the invention is directed to a method of treating a FAAH mediated disease in a patient in need of such treatment comprising: administration to a patient in need of such treatment of a therapeutically effective amount of a compound of formula I, according to claim 1 and a pharmaceutically acceptable carrier.

In another aspect, the invention is directed to a method of treating a disease is selected from osteoarthritis, rheumatoid arthritis, diabetic neuropathy, postherpetic neuralgia, pain, fibromyalgia, pain, migraine, sleep disorder, Alzheimer Disease, and Parkinson's Disease comprising: administration to a patient in need of such treatment of a therapeutically effective amount of a compound of formula I, and a pharmaceutically acceptable carrier.

In another aspect the invention is directed to the use of a compound according of Formula I or a pharmaceutically acceptable salt thereof for the manufacture of a medicament for the treatment of a physiological disorder associated with an excess of FAAH in a mammal.

The compounds of the present invention may contain one or more asymmetric centers and can thus occur as racemates and racemic mixtures, single enantiomers, diastereomeric mixtures and individual diastereomers. Additional asymmetric centers may be present depending upon the nature of the various substituents on the molecule. Each such asymmetric center will independently produce two optical isomers and it is intended that all of the possible optical isomers and diastereomers in mixtures and as pure or partially purified compounds are included within the ambit of this invention. The present invention is meant to comprehend all such isomeric forms of these compounds. Formula I shows the structure of the class of compounds without preferred stereochemistry. The independent syntheses of these diastereomers or their chromatographic separations may be achieved as known in the art by appropriate modification of the methodology disclosed herein. Their absolute stereochemistry may be determined by the x-ray crystallography of crystalline products or crystalline intermediates which are derivatized, if necessary, with a reagent containing an asymmetric center of known absolute configuration. If desired, racemic mixtures of the compounds may be separated so that the individual enantiomers are isolated. The separation can be carried out by methods well known in the art, such as the coupling of a racemic mixture of compounds to an enantiomerically pure compound to form a diastereomeric mixture, followed by separation of the individual diastereomers by standard methods, such as fractional crystallization or chromatography. The coupling reaction is often the formation of salts using an enantiomerically pure acid or base. The diasteromeric derivatives may then be converted to the pure enantiomers by cleavage of the added chiral residue. The racemic mixture of the compounds can also be separated directly by chromatographic methods utilizing chiral stationary phases, which methods are well known in the art. Alternatively, any enantiomer of a compound may be obtained by stereoselective synthesis using optically pure starting materials or reagents of known configuration by methods well known in the art.

In the compounds of generic Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of generic Formula I. For example, different isotopic forms of hydrogen (H) include protium ($^1$H) and deuterium ($^2$H). Protium is the predominant hydrogen isotope found in nature.

Enriching for deuterium may afford certain therapeutic advantages, such as increasing in vivo half-life or reducing dosage requirements, or may provide a compound useful as a standard for characterization of biological samples. Isotopically-enriched compounds within generic Formula I can be prepared without undue experimentation by conventional techniques well known to those skilled in the art or by processes analogous to those described in the Schemes and Examples herein using appropriate isotopically-enriched reagents and/or intermediates.

The present invention also includes all pharmaceutically acceptable isotopic variations of a compound of the Formula I in which one or more atoms is replaced by atoms having the same atomic number, but an atomic mass or mass number different from the atomic mass or mass number usually found in nature.

Examples of isotopes suitable for inclusion in the compounds of the invention include isotopes of hydrogen such as 2H and 3H, carbon such as $^{11}C$, $^{13}C$ and $^{14}C$, nitrogen such as $^{13}N$ and $^{15}N$, oxygen such as $^{15}O$, $^{17}O$ and $^{18}O$, phosphorus such as $^{32}P$, sulfur such as $^{35}S$, fluorine such as $^{18}F$, iodine such as $^{123}I$ and $^{125}I$, and chlorine such as $^{36}Cl$.

Certain isotopically-labelled compounds of Formula I, for example those incorporating a radioactive isotope, are useful in drug and/or substrate tissue distribution studies. The radioactive isotopes tritium, i.e. $^3H$, and carbon-14, i.e. $^{14}C$, are particularly useful for this purpose in view of their ease of incorporation and ready means of detection.

Substitution with heavier isotopes such as deuterium, i.e. $^2H$, may afford certain therapeutic advantages resulting from greater metabolic stability, for example, increased in vivo half-life or reduced dosage requirements, and hence may be preferred in some circumstances. Substitution with positron emitting isotopes, such as $^{11}C$, $^{18}F$, $^{15}O$ and $^{13}N$, can be useful in Positron Emission Topography (PET) studies for examining substrate receptor occupancy. Isotopically-labelled compounds of Formula I can generally be prepared by conventional techniques known to those skilled in the art or by processes analogous to those described in the accompanying Examples using appropriate isotopically-labelled reagents in place of the non-labelled reagent previously employed.

The invention is described using the following definitions unless otherwise indicated.

The teen "halogen" or "halo" includes F, Cl, Br, and I.

The term "alkyl" means linear or branched structures and combinations thereof, having the indicated number of carbon atoms. Thus, for example, $C_{1-6}$alkyl includes methyl, ethyl, propyl, 2-propyl, s- and t-butyl, butyl, pentyl, hexyl, 1,1-dimethylethyl.

The term "alkoxy" means alkoxy groups of a straight, branched or cyclic configuration having the indicated number of carbon atoms. $C_{1-6}$alkoxy, for example, includes methoxy, ethoxy, propoxy, isopropoxy, and the like.

The term "alkylthio" means alkylthio groups having the indicated number of carbon atoms of a straight, branched or cyclic configuration. $C_{1-6}$alkylthio, for example, includes methylthio, propylthio, isopropylthio, and the like.

The term "alkenyl" means linear or branched structures and combinations thereof, of the indicated number of carbon atoms, having at least one carbon-to-carbon double bond, wherein hydrogen may be replaced by an additional carbon-to-carbon double bond. $C_{2-6}$alkenyl, for example, includes ethenyl, propenyl, 1-methylethenyl, butenyl and the like.

The term "alkynyl" means linear or branched structures and combinations thereof of the indicated number of carbon atoms, having at least one carbon-to-carbon triple bond. $C_{3-6}$alkynyl, for example, includes propynyl, 1-methylethynyl, butynyl and the like.

The term "cycloalkyl" means mono-, bi- or tri-cyclic structures, optionally combined with linear or branched structures, the indicated number of carbon atoms. Examples of cycloalkyl groups include cyclopropyl, cyclopentyl, cycloheptyl, adamantyl, cyclododecylmethyl, 2-ethyl-1-bicyclo[4.4.0]decyl, and the like.

The term "aryl" is defined as a mono- or bi-cyclic aromatic ring system and includes, for example, phenyl, naphthyl, and the like.

The term "aralkyl" means an alkyl group as defined above of 1 to 6 carbon atoms with an aryl group as defined above substituted for one of the alkyl hydrogen atoms, for example, benzyl and the like.

The term "aryloxy" means an aryl group as defined above attached to a molecule by an oxygen atom (aryl-O) and includes, for example, phenoxy, naphthoxy and the like.

The term "aralkoxy" means an aralkyl group as defined above attached to a molecule by an oxygen atom (aralkyl-O) and includes, for example, benzyloxy, and the like.

The term "arylthio" is defined as an aryl group as defined above attached to a molecule by a sulfur atom (aryl-S) and includes, for example, thiophenyoxy, thionaphthoxy and the like.

The term "aroyl" means an aryl group as defined above attached to a molecule by an carbonyl group (aryl-C(O)—) and includes, for example, benzoyl, naphthoyl and the like.

The term "aroyloxy" means an aroyl group as defined above attached to a molecule by an oxygen atom (aroyl-O) and includes, for example, benzoyloxy or benzoxy, naphthoyloxy and the like.

The term "HET", such as in "$HET^1$", "$HET^2$", "$HET^3$", "$HET^4$" is defined as a 5- to 10-membered aromatic, partially aromatic or non-aromatic mono- or bicyclic ring, containing 1-4 heteroatoms selected from O, S and N, and optionally substituted with 1-2 oxo groups. Where applicable, the Het group shall be defined to include the N-oxide. Preferably, "HET" is a 5- or 6-membered aromatic or non-aromatic monocyclic ring containing 1-3 heteroatoms selected from O, S and N, for example, pyridine, pyrimidine, pyridazine, furan, thiophene, thiazole, oxazole, isooxazole and the like, or HET is a 9- or 10-membered aromatic or partially aromatic bicyclic ring containing 1-3 heteroatoms selected from O, S, and N, for example, benzofuran, benzothiophene, indole, pyranopyrrole, benzopyran, quionoline, benzocyclohexyl, naphtyridine and the like. "HET" also includes the following: benzimidazolyl, benzofuranyl, benzopyrazolyl, benzotriazolyl, benzothiophenyl, benzoxazolyl, carbazolyl, carbolinyl, cinnolinyl, furanyl, imidazolyl, indolinyl, indolyl, indolazinyl, indazolyl, isobenzofuranyl, isoindolyl, isoquinolyl, isothiazolyl, isoxazolyl, naphthyridinyl, oxadiazolyl, oxazolyl, pyrazinyl, pyrazolyl, pyridopyridinyl, pyridazinyl, pyridyl, pyrinaidyl, pyrrolyl, quinazolinyl, quinolyl, quinoxalinyl, thiadiazolyl, thiazolyl, thienyl, triazolyl, azetidinyl, 1,4-dioxanyl, hexahydroazepinyl, piperazinyl, piperidinyl, pyrrolidinyl, thiomorpholinyl, dihydrobenzimidazolyl, dihydrobenzofuranyl, dihydrobenzothiophenyl, dihydrobenzoxazolyl, dihydrofuranyl, dihydroimidazolyl, dihydroindolyl, dihydroisooxazolyl, dihydroisothiazolyl, dihydrooxadiazolyl, dihydrooxazolyl, dihydropyrazinyl, dihydropyrazolyl, dihydropyridinyl, dihydropyrimidinyl, dihydropyrrolyl, dihydroquinolinyl, dihydrotetrazolyl, dihydrothiadiazolyl, dihydrothiazolyl, dihydrothienyl, dihydrotriazolyl, dihydroazetidinyl, methylenedioxybenzoyl, tetrahydrofuranyl, and tetrahydrothienyl. In one aspect "HET" is selected from pyridyl, pyridazinyl, pyrimidinyl, pyrazinyl, thiazolyl, thienyl, pyrrolyl, oxazolyl, and oxadiazole;

For all of the above definitions, each reference to a group is independent of all other references to the same group when referred to in the Specification. For example, if both $R^1$ and $R^2$ are HET, the definitions of HET are independent of each other and $R^1$ and $R^2$ may be different HET groups, for example furan and thiophene.

The ability of the compounds of Formula I to selectively inhibit FAAH makes them useful for treating, preventing or reversing the progression of a variety of inflammatory and non-inflammatory diseases and conditions.

Diseases, disorders, syndromes and/or conditions, that would benefit from inhibition of FAAH enzymatic activity include, for example, Alzheimer's Disease, schizophrenia, depression, alcoholism, addiction, suicide, Parkinson's disease, Huntington's disease, stroke, emesis, miscarriage, embryo implantation, endotoxic shock, liver cirrhosis, atherosclerosis, cancer, traumatic head injury, glaucoma, and bone cement implantation syndrome.

Other diseases, disorders, syndromes and/or conditions that would benefit from inhibition of FAAH activity, include, for example, multiple sclerosis, retinitis, amyotrophic lateral sclerosis, immunodeficiency virus-induced encephalitis, attention-deficit hyperactivity disorder, pain, nociceptive pain, neuropathic pain, inflammatory pain, noninflammatory pain, painful hemorrhagic cystitis, obesity, hyperlipidemia, metabolic disorders, feeding and fasting, alteration of appetite, stress, memory, aging, hypertension, septic shock, cardiogenic shock, intestinal inflammation and motility, irritable bowel syndrome, colitis, diarrhea, ileitis, ischemia, cerebral ischemia, hepatic ischemia, myocardial infarction, cerebral excitotoxicity, seizures, febrile seizures, neurotoxicity, neuropathies, sleep, induction of sleep, prolongation of sleep, insomnia, and inflammatory diseases. Neurological and psychological disorders that would benefit from inhibition of FAAH activity include, for example, pain, depression, anxiety, generalized anxiety disorder (GAD), obsessive compulsive disorders, stress, stress urinary incontinence, attention deficit hyperactivity disorders, schizophrenia, psychosis, Parkinson's disease, muscle spasticity, epilepsy, diskenesia, seizure disorders, jet lag, and insomnia.

FAAH inhibitors can also be used in the treatment of a variety of metabolic syndromes, diseases, disorders and/or conditions, including but not limited to, insulin resistance syndrome, diabetes, hyperlipidemia, fatty liver disease, obesity, atherosclerosis and arteriosclerosis. FAAH inhibitors are useful in the treatment of a variety of painful syndromes, diseases, disorders and/or conditions, including but not limited to those characterized by non-inflammatory pain, inflammatory pain, peripheral neuropathic pain, central pain, deafferentiation pain, chronic nociceptive pain, stimulus of nociceptive receptors, phantom and transient acute pain.

Inhibition of FAAH activity can also be used in the treatment of a variety of conditions involving inflammation. These conditions include, but are not limited to arthritis (such as rheumatoid arthritis, shoulder tendonitis or bursitis, gouty arthritis, and aolymyalgia rheumatica), organ-specific inflammatory diseases (such as thyroiditis, hepatitis, inflammatory bowel diseases), asthma, other autoimmune diseases (such as multiple sclerosis), chronic obstructive pulmonary disease (COPD), allergic rhinitis, and cardiovascular diseases.

In some cases, FAAH inhibitors are useful in preventing neurodegeneration or for neuroprotection.

In addition, it has been shown that when FAAH activity is reduced or absent, one of its substrates, anandamide, acts as a substrate for COX-2, which converts anandamide to prostamides (Weber et al J Lipid. Res. 2004; 45:757). Concentrations of certain prostamides may be elevated in the presence of a FAAH inhibitor. Certain prostamides are associated with reduced intraocular pressure and ocular hypotensivity. Thus, in one embodiment, FAAH inhibitors may be useful for treating glaucoma.

In some embodiments, FAAH inhibitors can be used to treat or reduce the risk of EMDs, which include, but are not limited to, obesity, appetite disorders, overweight, cellulite, Type I and Type II diabetes, hyperglycemia, dyslipidemia, steatohepatitis, liver steatosis, non-alcoholic steatohepatitis, Syndrome X, insulin resistance, diabetic dyslipidemia, anorexia, bulimia, anorexia nervosa, hyperlipidemia, hypertriglyceridemia, atherosclerosis, arteriosclerosis, inflammatory disorders or conditions, Alzheimer's disease, Crohn's disease, vascular inflammation, inflammatory bowel disorders, rheumatoid arthritis, asthma, thrombosis, or cachexia.

In other embodiments, FAAH inhibitors can be used to treat or reduce the risk of insulin resistance syndrome and diabetes, i.e., both primary essential diabetes such as Type I Diabetes or Type II Diabetes and secondary nonessential diabetes. Administering a composition containing a therapeutically effective amount of an in vivo FAAH inhibitor reduces the severity of a symptom of diabetes or the risk of developing a symptom of diabetes, such as atherosclerosis, hypertension, hyperlipidemia, liver steatosis, nephropathy, neuropathy, retinopathy, foot ulceration, or cataracts.

In another embodiment, FAAH inhibitors can be used to treat food abuse behaviors, especially those liable to cause excess weight, e.g., bulimia, appetite for sugars or fats, and non-insulin-dependent diabetes.

In some embodiments, FAAH inhibitors can be used to treat a subject suffering from an EMD and also suffers from a depressive disorder or from an anxiety disorder. Preferably, the subject is diagnosed as suffering from the depressive or psychiatric disorder prior to administration of the FAAH inhibitor composition. Thus, a dose of a FAAH inhibitor that is therapeutically effective for both the EMD and the depressive or anxiety disorder is administered to the subject.

Preferably, the subject to be treated is human. However, the methods can also be used to treat non-human mammals. Animal models of EMDs such as those described in, e.g., U.S. Pat. No. 6,946,491 are particularly useful.

FAAH inhibitor compositions can also be used to decrease body-weight in individuals wishing to decrease their body weight for cosmetic, but not necessarily medical considerations.

A FAAH inhibitor composition can be administered in combination with a drug for lowering circulating cholesterol levels (e.g., statins, niacin, fibric acid derivatives, or bile acid binding resins). FAAH inhibitor compositions can also be used in combination with a weight loss drug, e.g., orlistat or an appetite suppressant such as diethylpropion, mazindole, orlistat, phendimetrazine, phentermine, or sibutramine.

The term "treating" encompasses not only treating a patient to relieve the patient of the signs and symptoms of the disease or condition but also prophylactically treating an asymptomatic patient to prevent the onset of the disease or condition or preventing, slowing or reversing the progression of the disease or condition. The term "amount effective for treating" is intended to mean that amount of a drug or pharmaceutical agent that will elicit the biological or medical response of a tissue, a system, animal or human that is being sought by a researcher, veterinarian, medical doctor or other clinician. The term also encompasses the amount of a pharmaceutical drug that will prevent or reduce the risk of occurrence of the biological or medical event that is sought to be prevented in a tissue, a system, animal or human by a researcher, veterinarian, medical doctor or other clinician.

The following abbreviations have the indicated meanings:
AIBN=2.2'-azobisisobutyronitrile
B.P.=benzoyl peroxide
Bn=benzyl
$CCl_4$=carbon tetrachloride
D=—$O(CH_2)_3O$—
DAST=diethylamine sulfur trifluoride
DCC=dicyclohexyl carbodiimide
DCI=1-(3-dimethylaminopropyl)-3-ethyl carbodiimide
DEAD=diethyl azodicarboxylate
DIBAL=diisobutyl aluminum hydride
DME=ethylene glycol dimethylether
DMAP=4-(dimethylamino)pyridine
DMF=N,N-dimethylformamide
DMSO=dimethyl sulfoxide
$Et_3N$=triethylamine
LDA=diisopropylamide
m-CPBA=metachloroperberizoic acid
NBS=N-bromosuccinimide
NSAID=non-steroidal anti-inflammatory drug
PCC=pyridinium chlorochromate
PDC=pyridinium dichromate
Ph=phenyl
1,2-Ph=1,2-benzenediyl
Pyr=pyridinediyl
Qn=7-chloroquinolin-2-yl
$R^s$=—$CH_2SCH_2CH_2Ph$
r.t.=room temperature
rac.=racemic
THF=tetrahydrofuran
THP=tetrahydropyran-2-yl Alkyl Group Abbreviations
Me=methyl
Et=ethyl
n-Pr=normal propyl
i-Pr=isopropyl
n-Bu=normal butyl
i-Bu=isobutyl
s-Bu=secondary butyl
t-Bu=tertiary butyl
c-Pr=cyclopropyl
c-Bu=cyclobutyl
c-Pen=cyclopentyl
c-Hex=cyclohexyl Some of the compounds described herein contain one or more asymmetric centers and may thus give rise to diastereomers and optical isomers. The present invention is meant to comprehend such possible diastereomers as well as their racemic and resolved, enantiomerically pure forms and pharmaceutically acceptable salts thereof.

Some of the compounds described herein contain olefinic double bonds, and unless specified otherwise, are meant to include both E and Z geometric isomers.

The pharmaceutical compositions of the present invention comprise a compound of Formula I as an active ingredient or a pharmaceutically acceptable salt, thereof, and may also contain a pharmaceutically acceptable carrier and optionally other therapeutic ingredients. The term "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium, and sodium salts. Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfuric, and tartaric acids.

It will be understood that in the discussion of methods of treatment which follows, references to the compounds of Formula I are meant to also include the pharmaceutically acceptable salts.

The magnitude of prophylactic or therapeutic dose of a compound of Formula I will, of course, vary with the nature and the severity of the condition to be treated and with the particular compound of Formula I and its route of administration. It will also vary according to a variety of factors including the age, weight, general health, sex, diet, time of administration, rate of excretion, drug combination and response of the individual patient. In general, the daily dose from about 0.001 mg to about 100 mg per kg body weight of a mammal, preferably 0.01 mg to about 10 mg per kg. On the other hand, it may be necessary to use dosages outside these limits in some cases.

The amount of active ingredient that may be combined with the carrier materials to produce a single dosage form will vary depending upon the host treated and the particular mode of administration. For example, a formulation intended for oral administration to humans may contain from about 0.5 mg to about 5 g of active agent compounded with an appropriate and convenient amount of carrier material which may vary from about 5 to about 95 percent of the total composition. Dosage unit forms will generally contain from about 1 mg to about 2 g of an active ingredient, typically 25 mg, 50 mg, 100 mg, 200 mg, 300 mg, 400 mg, 500 mg, 600 mg, 800 mg, or 1000 mg.

For the treatment of FAAH mediated diseases the compound of Formula I may be administered orally, topically, parenterally, by inhalation spray or rectally in dosage unit formulations containing conventional non-toxic pharmaceutically acceptable carriers, adjuvants and vehicles. The teen parenteral as used herein includes subcutaneous, intravenous, intramuscular, intrasternal injection or infusion techniques. In addition to the treatment of warm-blooded animals such as mice, rats, horses, cattle, sheep, dogs, cats, etc., the compound of the invention is effective in the treatment of humans.

The pharmaceutical compositions containing the active ingredient may be in a form suitable for oral use, for example, as tablets, troches, lozenges, solutions, aqueous or oily suspensions, dispersible powders or granules, emulsions, hard or soft capsules, syrups or elixirs. Compositions intended for oral use may be prepared according to any method known to the art for the manufacture of pharmaceutical compositions and such compositions may contain one or more agents selected from the group consisting of sweetening agents, flavouring agents, colouring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the technique described in the U.S. Pat. Nos. 4,256,108; 4,166,452; and 4,265,874 to form osmotic therapeutic tablets for control release.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water-miscible solvents such as propylene glycol, PEGS and ethanol, or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropyl methylcellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more colouring agents, one or more flavouring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavouring agents may be added to provide a palatable oral preparation. These compositions may be preserved by the addition of an anti-oxidant such as ascorbic acid.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavouring and colouring agents, may also be present.

The pharmaceutical compositions of the invention may also be in the form of an oil-in-water emulsion. The oily phase may be a vegetable oil, for example olive oil or arachis oil, or a mineral oil, for example liquid paraffin or mixtures of these. Suitable emulsifying agents may be naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening and flavouring agents.

Syrups and elixirs may be formulated with sweetening agents, for example glycerol, propylene glycol, sorbitol or sucrose. Such formulations may also contain a demulcent, a preservative and flavouring and colouring agents. The pharmaceutical compositions may be in the form of a sterile injectable aqueous or oleagenous suspension. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. Among the acceptable vehicles and solvents that may be employed are water, Ringer's solution and isotonic sodium chloride solution. Cosolvents such as ethanol, propylene glycol or polyethylene glycols may also be used. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds of Formula I may also be administered in the form of suppositories for rectal administration of the drug. These compositions can be prepared by mixing the drug with a suitable non-irritating excipient which is solid at ambient temperatures but liquid at the rectal temperature and will therefore melt in the rectum to release the drug. Such materials are cocoa butter and polyethylene glycols.

For topical use, creams, ointments, gels, solutions or suspensions, etc., containing a compound of Formula I are employed. (For purposes of this application, topical application shall include mouth washes and gargles.) Topical formulations may generally be comprised of a pharmaceutical carrier, cosolvent, emulsifier, penetration enhancer, preservative system, and emollient.

Assays

The following assays illustrate the utility of the invention:

The compounds of the invention underwent pharmacological evaluations to determine their inhibitory effect on the enzyme FAAH (Fatty Acid Amide Hydrolase).

To assist in assay development stable cell lines for human, murine and rat full length FAAH were developed. Human FAAH cDNA (Accession No: NM_001441.1) was purchased from Origene (Rockville, Md.). The full length FAAH was subcloned into the mammalian expression vector, pcDEF.neo, using XbaI and EcoRI restriction sites and used for stable cell line generation.

| Construct | Primer | Sequence |
|---|---|---|
| Full length rodent FAAH | 1 | CAAGGTACCGCCACCATGG TGCTGAGCGAAGTGTGG |
| Full length murine FAAH | 2 | CCGGAATTCTCAAGATGGC CGCTTTTCAGG |
| Full length rat FAAH | 3 | CCGGAATTCTCACGATGGC TGCTTTTGAGG |

Murine (accession number NM_010173) and Rat FAAH (accession number NM_024132) was amplified by reverse transcriptase polymerase chain reaction (RT-PCR) from brain cDNA (BD Biosciences, San Jose, Calif.) using primers 1 and 2 or primers 1 and 3 respectively (see Table). The resulting PCR product was ligated into pCR4 TOPO and DNA sequence confirmed. The full length murine FAAH was subcloned into the mammalian expression vector, pcDEFneo using either EcoRI (murine) or KpnI and EcoRI (rat) restriction sites. Chinese hamster ovary cells (CHO) were transfected following manufacturers protocol (AMAXA). Forty eight hours post transfection, cells were trypsinized and transferred to 96 well plates in Iscove's DMEM media supplemented with 2 mM Glutamine, 10% fetal calf serum, 1 mg/ml geneticin and HT Supplement (0.1 mM sodium hypoxanthine, 0.016 mM thymidine) in order to isolate single clones. Following selection in geneticin, individual clones were selected and FAAH activity was assessed using a whole cell fluorescent anandamide assay, modified from Ramarao et al (2005). Following removal of tissue culture media cells were dislodged following addition of Cellstripper (Mediatech, Inc. Manassas, Va.) and transferred to 96 well black clear bottom assay plate, centrifuged at 1,000 rpm for 3 mins and media removed and replaced with assay buffer (50 mM Tris pH8.0, 1 mM EDTA, 0.1% fatty acid free BSA). The reaction was initiated by addition of fluorescent substrate, AMC Arachidonoyl Amide (Cayman Chemical, Ann Arbor, Mich.) to 1 µM and reaction allowed to proceed for 2 hours at room temperature. Release of fluorescence was monitored in a CytoFluor Multiplate Reader. Cells expressing the highest amount of FAAH activity were selected for study with FAAH inhibitors.

Preparation of Lysate and Microsomes

CHO cells expressing FAAH were used to prepare either crude cell lysate or microsome fractions. To harvest cells, tissue culture media was decanted, the monolayer washed three times with $Ca^{++Mg++}$ free PBS and cells recovered after 15 min in enzyme free dissociation media (Millipore Corp, Billerica, Mass.). Cells were collected by centrifuging at 2000 rpm for 15 min, and the cell pellet re-suspended with 50 mM HEPES (pH 7.4) containing 1 mM EDTA and the protease inhibitors aprotinin (1 mg/ml) and leupeptin (100 µM). The suspension was sonicated at 4° C. and the cell lysate recovered after centrifuging at 12,000×g (14,600 rpm, SS34 rotor) for 20 min at 4° C. to form a crude pellet of cell debris, nuclei, peroxisomes, lysosomes, and mitochondria; the supernatant or cell lysate was used for FAAH enzyme assay. In some cases, microsomes fractions enriched in FAAH were prepared by centrifuging the cell lysate further at 27,000 rpm (100,000×g) in SW28 rotor for 50 minutes at 4° C. The pellet containing FAAH-enriched microsomes was re-suspend in 50 mM HEPES, (pH 7.4) 1 mM EDTA, and any remaining DNA sheared by passage of material through a 23 gauge needle and aliquots of enzyme were store at −80° C. prior to use.

FAAH Assays

Several assays have been used to demonstrate the inhibitory activity. Enzyme activity was demonstrated in a radioenzymatic test based on measuring the product of hydrolysis (ethanolamine [$^3$H]) of anandamide [ethanolamine 1-.sup.3H] (American Radiolabeled Chemicals; 1 mCi/ml) with FAAH (Life Sciences (1995), 56, 1999-2005 and Journal of Pharmacology and Experimented Therapeutics (1997), 283, 729-734), Analytical. Biochemistry (2003), 318, 270-5. In addition, routine assays were performed monitoring hydrolysis of arachidonyl-7-amino-4-methylcoumarin amide (AAMCA) by following increase in fluorescence upon release of 7-amino 4-methyl coumarin ($\lambda_{EX}$=355 nm, $\lambda_{EM}$=460 nm). Analytical. Biochemistry (2005), 343, 143-51.

Assays are performed on either cell lysate or microsome fractions prepared as described or in whole cell format employing either the fluorescent substrate AAMCA (Cayman chemical, Ann Arbor, Mich.,) or $^3$H-anandamide ([ETHA-NOLAMINE-1-3H] American Radiolabeled Chemicals; 1 mCi/ml). The cell lysate or microsome assay is performed in black PerkinElmer OptiPlates-384F by adding FAAH_CHO (whole cell, cell lysate or microsome) in assay buffer (50 mM Phosphate, pH 8.0, 1 mM EDTA, 200 mM KCl, 0.2% glycerol, 0.1% fatty acid free BSA) to each well, followed by either DMSO or compound and allowed to incubate at 22-25° C. for fifteen minutes. AAMCA substrate was used to achieve a final concentration of 1 µM and reaction allowed to proceed at room temperature for 1-3 hours. Fluorescent release as a measure of FAAH activity was monitored by reading the plate in an Envision plate Reader (Ex: 360/40 nM; Em: 460/40 nM). Whole cell assay is conducted with cells harvested after rinsing tissue culture flasks three times with $Ca^{++}Mg^{++}$ free PBS, incubating for 10 min in Enzyme free dissociation media and centrifuging for 5 minutes at 1,000 rpm in table top centrifuge. Cells are resuspended in assay buffer at desired cell number in ($4\times10^4$ cells/assay in 96-well format; $1\times10^4$ cells/assay in 384-well format) and assayed as described.

Alternatively, assays are performed using anandamide [ethanolamine 1-.sup.3H] (specific activity of 10 Ci/mmol) diluted with cold anandamide to achieve a final assay concentration of 1 µM anandamide (~50,000 cpm). Enzyme (CHO cell lysate, brain or liver homogenate) is incubated in assay buffer (50 mM Phosphate, pH 8.0, 1 mM EDTA, 200 mM KCl, 0.2% glycerol, 0.1% fatty acid free BSA) with inhibitor at 25° C. for 30 minutes. The reaction was terminated by addition of 2 volumes of chloroform:methanol (1:1) and mixed by vortexing. Following a centrifugation step, 2000 rpm for 10 mM. at room temperature, the aqueous phase containing the released $^3$H-ethanolamide was recovered and quantitated by liquid scintillation as a reflection of FAAH enzyme activity.

Ramarao M. K., et al. A fluorescence-based assay for fatty acid amide hydrolase compatible with high-throughput screening. Anal. Biochem. 343:143-51 (2005)

Wilson S I, et 1. A high-throughput-compatible assay for determining the activity of fatty acid amide hydrolase. Anal Biochem. 318:270-5 (2003).

Each of Examples was tested and found to demonstrate biological activity. Results for specific Examples are provided below. Each of Examples was found to have an IC50 of 10 µM or lower in these assays.

| Example # | Human lysate IC50 (nM) | Human whole cell IC50 (nM) |
|---|---|---|
| A7.13 | 67.48 | 771.3 |
| A7.15 | 1418 | 10000 |
| A7.14 | 65.35 | 443.3 |
| A7.16 | 925.4 | 10000 |
| A7.17 | 75.13 | 547.1 |
| A7.18 | 839.2 | 4416 |
| A7.19 | 287.3 | 3283 |
| A7.20 | 1700 | 10000 |
| A7.21 | 25.94 | 124.1 |
| A7.22 | 45.79 | 382.6 |
| A7.23 | 61.67 | 435.8 |
| A7.24 | 200.5 | 1328 |
| C6.1 | 11.86 | 104.9 |
| A7.25 | 525.4 | 4673 |
| A7.26 | 747.7 | 6547 |
| A7.27 | 481.5 | 5005 |
| A7.28 | 3090 | 10000 |
| A7.29 | 1911 | 10000 |
| A7.30 | 2140 | 10000 |
| C6.3 | 15.89 | 31.04 |
| C6.2 | 8.678 | 47.2 |
| B5.2 | 4.192 | 10.92 |
| B5.1 | 17.9 | 45.06 |
| B5.3 | 12.83 | 38.49 |
| B5.4 | 27.62 | 63.8 |
| B5.5 | 255.4 | 1051 |
| B5.6 | 117.8 | 420.7 |
| B5.7 | 92.22 | 169.1 |
| B5.8 | 145.5 | 736.9 |
| B5.9 | 9.605 | 114.6 |
| B5.10 | 67.56 | 98.09 |
| B5.11 | 13.08 | 36.92 |
| B5.12 | 113 | 278.9 |
| B5.13 | 320.2 | 847.1 |
| B5.14 | 9146 | 10000 |
| A7.31 | 10000 | 10000 |
| A7.31a | 2220 | 5067 |
| B5.15 | 4526 | 10000 |
| A7.2 | 293.1 | 935.1 |
| A7.1 | | 313.8 |
| A7.3 | | 852.1 |
| A7.4 | | 454.3 |
| A7.5 | | 4251 |
| A7.6 | | 4138 |
| B5.33 | | 9.503 |
| B5.34 | | 14.25 |
| A7.7 | | 2215 |
| A7.8 | | 1185 |
| A7.9 | | 10000 |
| A7.10 | | 10000 |
| B5.36 | | 63.77 |
| B5.35 | | 9.065 |
| A7.32 | | 141.8 |
| A7.33 | | 1811 |
| B5.16 | | 155.3 |
| B5.17 | | 1528 |
| B5.18 | | 374.9 |
| B5.19 | | 2670 |
| B5.20 | | 383.1 |
| B5.21 | | 706.7 |
| B5.22 | | 40.29 |
| B5.23 | | 774.3 |
| B5.24 | | 10000 |
| B5.25 | | 205 |
| B5.26 | | 506.1 |
| B5.27 | | 140.7 |
| B5.29 | | 10000 |
| B5.30 | | |
| B5.31 | | 1340 |
| B5.32 | | 677.8 |
| A7.11 | | 701.3 |
| A7.34 | | 149.9 |
| A7.35 | | 10000 |
| A7.36 | | 10000 |
| A7.37 | | 1915 |
| A7.38 | | 10000 |
| A7.39 | | 2815 |
| A7.40 | | 9705 |
| A7.12 | | 290.2 |
| B5.37 | | 307.6 |
| B5.38 | | 184.9 |
| B5.39 | | 26.16 |

Preparation of the Compounds of the Invention.

The compounds of the present invention can be prepared according to the procedures denoted in the following reaction Schemes and Examples or modifications thereof using readily available starting materials, reagents, and conventional procedures thereof well-known to a practioner of ordinary skill in the art of synthetic organic chemistry. Specific definitions of variables in the Schemes are given for illustrative purposes only and are not intended to limit the procedures described.

General Scheme

Scheme A describes the synthesis of 2,4,5-trisubstituted oxazole type A7. Bromoketones A3 or A4 are heated with carboxamides to cyclize and give 2,4-disubstituted oxazoles type A5. Bromination at 5-position followed by cross-coupling affords A7. When A7 bears a piperidine group (X=NH), further substitution of nitrogen can be done using standard alkylation, acylation or sulfonylation procedures.

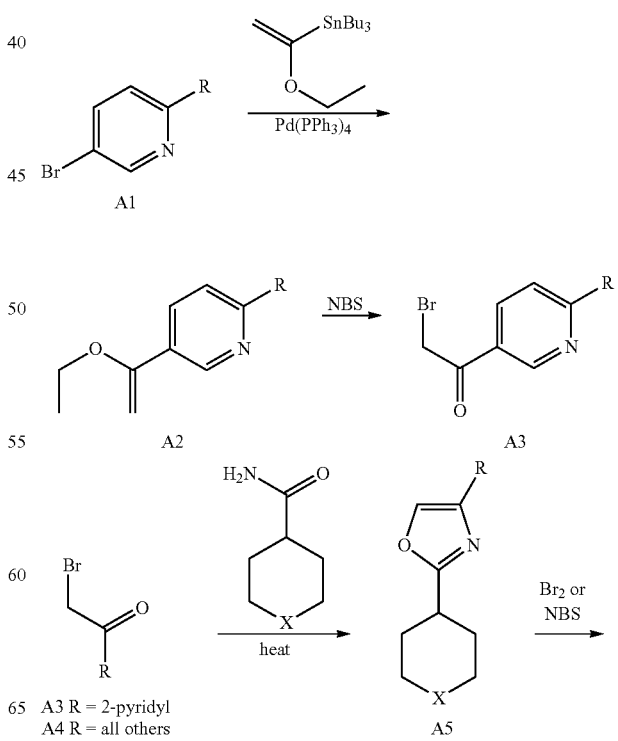

Scheme A

A3 R = 2-pyridyl
A4 R = all others

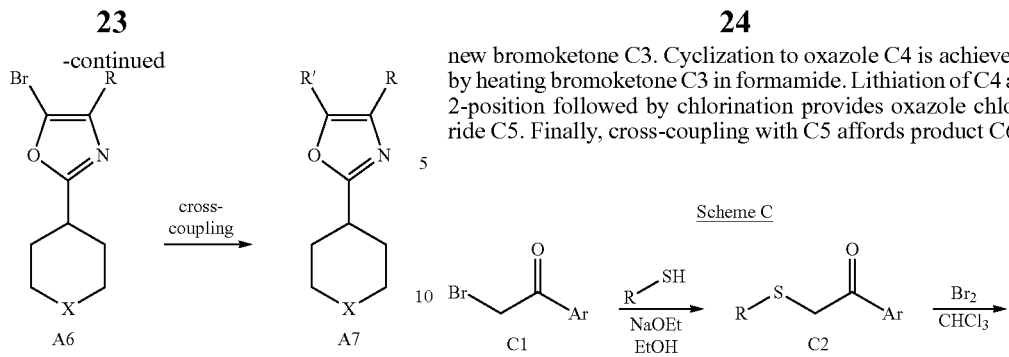

new bromoketone C3. Cyclization to oxazole C4 is achieved by heating bromoketone C3 in formamide. Lithiation of C4 at 2-position followed by chlorination provides oxazole chloride C5. Finally, cross-coupling with C5 affords product C6.

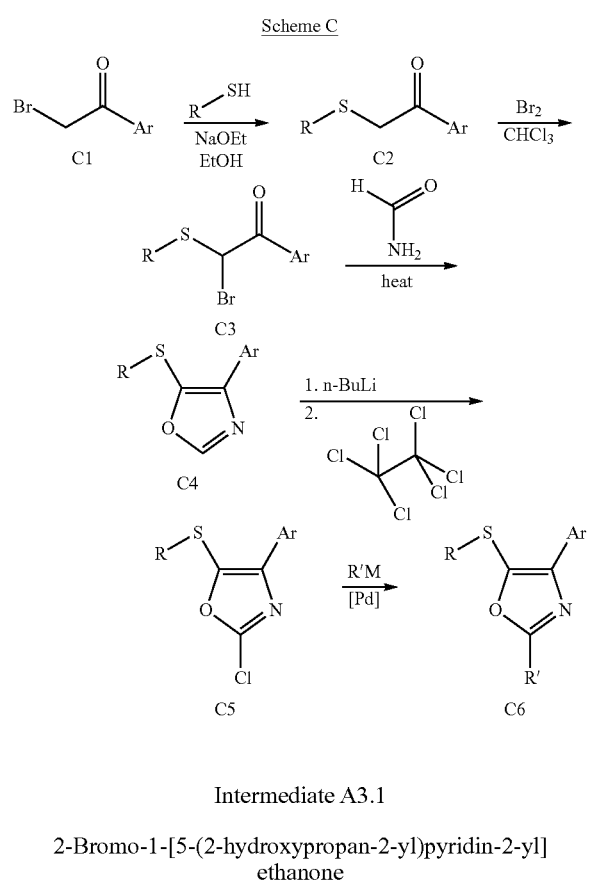

Scheme B describes the alternative synthetic route of trisubstituted oxazoles B5 with the final substitution at the 4-position. Thioethylamine B1 is coupled with tetrahydropyran or cyclohexane carboxylic acids to give amide B2. Treatment of B2 with NCS followed by tin chloride or TEA affords 2,5-disubstituted oxazoles B3. Bromination at 4-position of oxazole followed by Suzuki coupling give products type B5.

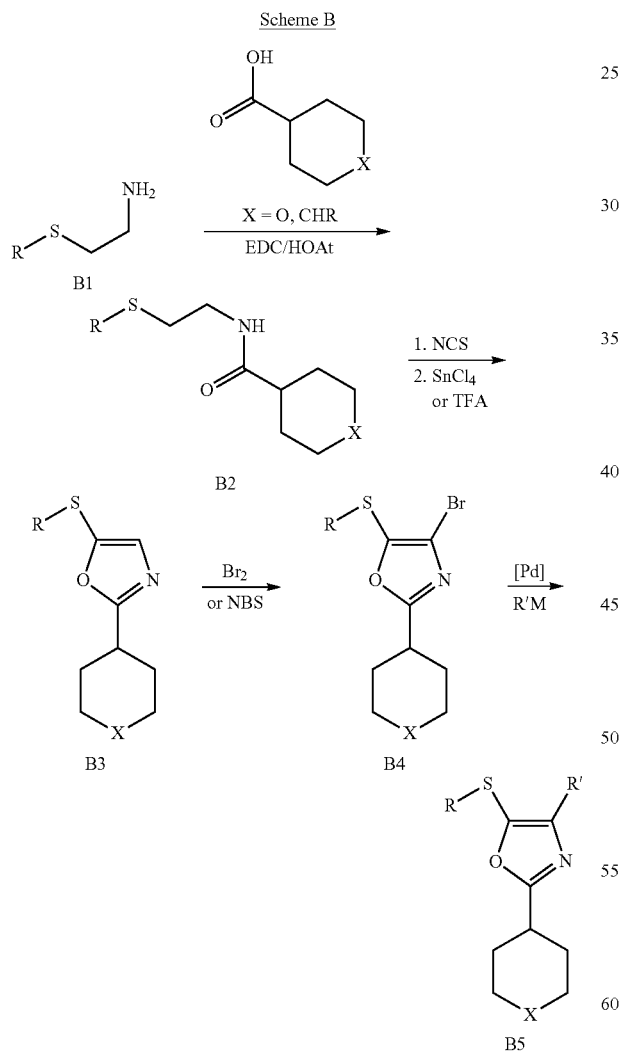

Scheme C describes another way of synthesis of trisubstituted oxazoles type C6 with the final substitution at the 2-position. α-Bromoketone C1 was converted to α-thioketone C2 via a $S_N2$-type reaction, followed by α-bromination to give Intermediate A3.1

2-Bromo-1-[5-(2-hydroxypropan-2-yl)pyridin-2-yl]ethanone

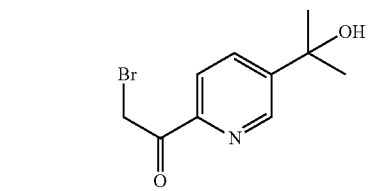

Step A3.1-1:
2-[6-(1-Ethoxyethenyl)pyridin-3-yl]propan-2-ol

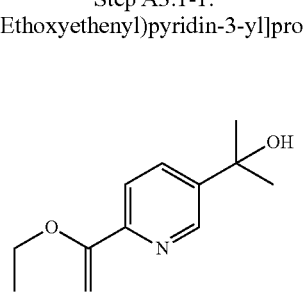

Tributyl(1-ethoxyethenyl)stannane (8.60 ml, 25.5 mmol) was added to a stirred, room temperature mixture of A1 (5.0 g, 23.1 mmol) and tetrakis(triphenylphosphine)palladium(0)

(1.34 g, 1.16 mmol) in 1,4-dioxane (101 ml). The mixture was stirred at 120° C. for overnight. After cooling, the reaction mixture was diluted with EtOAc and aqueous sat. KF, stirred vigorously for 1 h, filtered through Celite. The two layers were separated. The water layer was extracted with EtOAc. The combined organic layers were dried over $Na_2SO_4$, filtered and conc. The residue was purified by silica flash chromatography (5-40% EtOAc in hex) to give the product as a yellowish oil. LC-MS: $[M+H]^+=208.1$.

Step A3.1-2: 2-Bromo-1-[5-(2-hydroxypropan-2-yl)pyridin-2-yl]ethanone

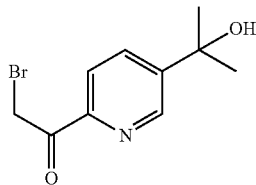

NBS (2.92 g, 16.4 mmol) was added to a stirred mixture of A2 (3.40 g, 16.4 mmol) in a mixture of THF (75 ml) and water (5 ml) and the mixture was stirred at room temperature for 30 min. The solvent was moved by concentration and the residue was purified by silica flash chromatography (10-75% EtOAc in hex). LC-MS: $[M+H]^+=258.2$. $^1$H NMR ($CDCl_3$, 400 MHz) δ 9.12 (d, J=2.0, Hz, 1H), 8.30 (dd, J=2.0, 8.4 Hz, 1H), 7.56 (d, J=8.4 Hz, 1H), 4.51 (s, 1H), 4.43 (s, 2H), 1.58 (s, 6H).

Intermediate A6.1

2-{5-[5-Bromo-2-(tetrahydro-2H-pyran-4-yl)-1,3-oxazol-4-yl]pyridin-2-yl}propan-2-ol

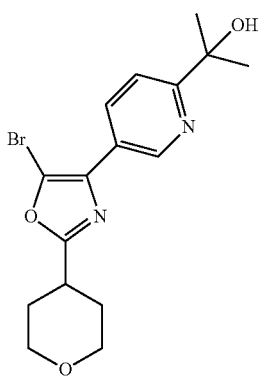

Step A6.1-1: 2-{5-[2-(Tetrahydro-2H-pyran-4-yl)-1,3-oxazol-4-yl]pyridin-2-yl}propan-2-ol

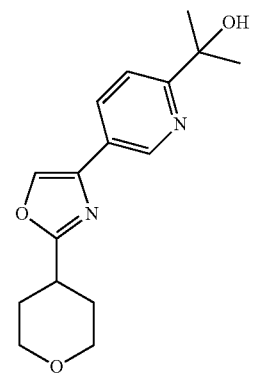 [SMILES: CC(C)(O)c1ccc(-c2coc(C3CCOCC3)n2)cn1]

A solution of tetrahydro-2H-pyran-4-carboxamide (2.43 g, 18.8 mmol) and bromoketone A3 (2.43 g, 9.41 mmol) in DMPU (18.8 mL) was heated at 100° C. for 7 h. The reaction was cooled and used as crude. LC-MS: $[M+H]^+=289.4$.

Step A6.1-2: 2-{5-[5-Bromo-2-(tetrahydro-2H-pyran-4-yl)-1,3-oxazol-4-yl]pyridin-2-yl}propan-2-ol

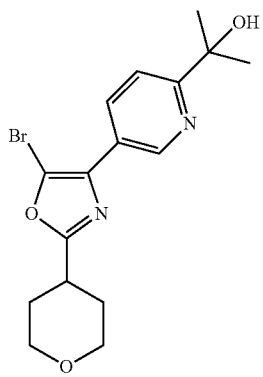 [SMILES: CC(C)(O)c1ccc(-c2nc(C3CCOCC3)oc2Br)cn1]

NBS (0.833 g, 4.68 mmol) was added to a stirred, cooled room temperature mixture of B3-1 (2.7 g, 9.36 mmol) in chloroform (46.8 ml) and the mixture was stirred at room temperature for 1 h. Additional 200 mg of NBS was added and the reaction was stirred at room temperature for 1 h. Additional 100 mg of NBS was added and the reaction was stirred at room temperature for another 1 h. The solvent was removed by concentration and the residue was purified by silica gel (10-100% EtOAc in hex). The product obtained still contained significant amount of DMPU. Second purification with reverse-phase chromatography (C-18, 10-90% MeCN in $H_2O$) afforded the pure product. LC-MS: $[M+H]^+=369.4$.

$^1$H NMR ($CDCl_3$, 400 MHz) δ 9.10 (dd, J=0.8, 2.0, Hz, 1H), 8.24 (dd, J=2.0, 8.4 Hz, 1H), 7.44 (dd, J=0.8, 8.4 Hz, 1H), 4.89 (s, 1H), 4.06 (td, J=3.2, 12.0 Hz, 2H), 3.55 (dt, J=2.8, 11.8 Hz, 2H), 3.10 (m, 1H), 2.07-1.93 (m, 4H), 1.57 (s, 6H).

Example A7.1

2-(5-{5-[(5-Chloropyridin-2-yl)sulfanyl]-2-(tetrahydro-2H-pyran-4-yl)-1,3-oxazol-4-yl}pyridin-2-yl)propan-2-ol

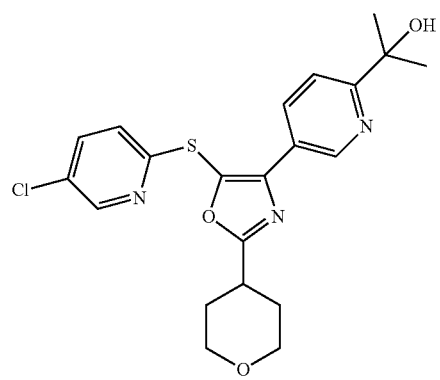

A mixture of oxazole 5-bromide A6.1 (172 mg, 0.467 mmol), 5-chloropyridine-2-thiol (136 mg, 0.934 mmol), K$_3$PO$_4$ (297 mmol, 1.40 mmol), N,N-dimethylglycine (9.6 mg, 0.093 mmol) and CuI (18 mg, 0.093 mmol) in DMF (4.67 mL) was heated at 145° C. for 5 h. Purification by reverse-phase HPLC (C-18, 35-95% MeCN in H$_2$O, with 0.05% TFA) provided the product. $^1$H NMR (CDCl$_3$, 400 MHz) δ 9.15 (bs, 1H), 8.39 (d, J=2.8 Hz, 1H), 8.32 (d, J=8.4 Hz, 1H), 7.54 (dd, J=3.0, 8.4 Hz, 1H), 7.42 (d, J=7.6 Hz, 1H), 6.95 (d, J=8.4 Hz, 1H), 4.84 (bs, 1H), 4.06 (td, J=3.6, 8.4 Hz, 2H), 3.57 (dt, J=3.2, 11.6 Hz, 2H), 3.17 (m, 1H), 2.10-1.97 (m, 4H), 1.55 (s, 6H). HRMS (ES) [M+1]$^+$ calcd for C$_{21}$H$_{23}$ClN$_3$O$_3$S: 432.1143. Found: 432.1141.

Intermediate A6.2

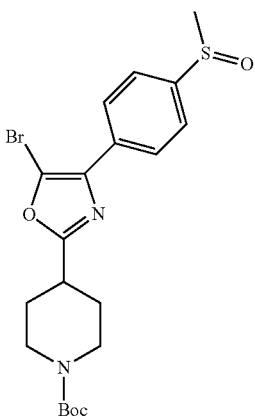 [SMILES: CS(=O)c1ccc(-c2nc(C3CCN(C(=O)OC(C)(C)C)CC3)oc2Br)cc1]

tert-Butyl 4-{5-bromo-4-[4-(methylsulfinyl)phenyl]-1,3-oxazol-2-yl}piperidine-1-carboxylate Step A6.2-1: tert-butyl 4-{4-[4-(methylsulfanyl)phenyl]-1,3-oxazol-2-yl}piperidine-1-carboxylate

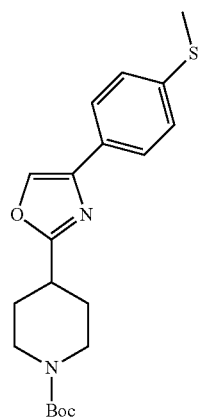 [SMILES: CSc1ccc(-c2coc(C3CCN(C(=O)OC(C)(C)C)CC3)n2)cc1]

2-Bromo-1-[4-(methylsulfanyl)phenyl]ethanone (5 g, 19.15 mmol) and tert-butyl 4-carbamoylpiperidine-1-carboxylate (4.37 g, 19.15 mmol) were dissolved in DMPU (40.8 mL) and heated to 145° C. for 15 min. The resulting solution was then cooled to room temperature, partitioned between aqueous LiCl and ethyl acetate. The combined organics were dried over sodium sulfate and concentrated in vacuo. The resulting crude oil was purified using silica gel chromatography (300 g, using 20-80% ethyl acetate in hexane gradient) to yield 1.8 g of the desired product as a yellow oil. LCMS (M+1)=375.40

Step A6.2-2: tert-butyl 4-{5-bromo-4-[4-(methylsulfanyl)phenyl]-1,3-oxazol-2-yl}piperidine-1-carboxylate

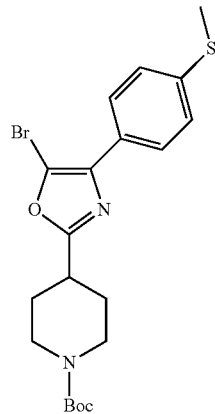 [SMILES: CSc1ccc(-c2nc(C3CCN(C(=O)OC(C)(C)C)CC3)oc2Br)cc1]

tert-butyl 4-{4-[4-(methylsulfanyl)phenyl]-1,3-oxazol-2-yl}piperidine-1-carboxylate (585 mg, 1.56 mmol) was dissolved in dichloromethane (15.6 mL) under argon atmosphere. N-bromosuccinimide (306 mg, 1.72 mmol) was added portionwise as a solid to the stirring solution. The resulting solution stirred at 25° C. for 6 hours. The solution was then diluted with chloroform and washed with aqueous sodium bisulfite. The organics were dried over sodium sulfate and concentrated in vacuo to yield 680 mg of the desired product as yellow oil. LCMS (M+1)=453.40

Step A6.2-3: tert-butyl 4-{5-bromo-4-[4-(methylsulfinyl)phenyl]-1,3-oxazol-2-yl}piperidine-1-carboxylate

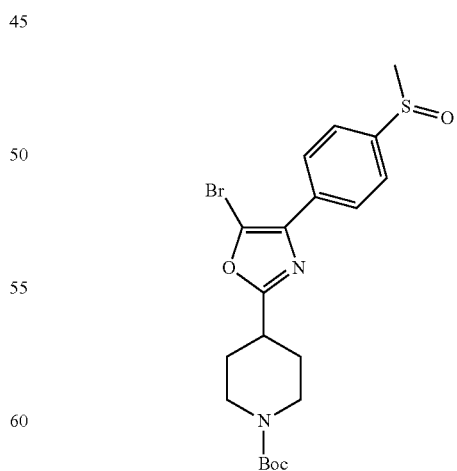

tert-Butyl 4-{5-bromo-4-[4-(methylsulfanyl)phenyl]-1,3-oxazol-2-yl}piperidine-1-carboxylate (705 mg, 1.55 mmol) was dissolved in methylene chloride (15.5 nit) under argon atmosphere. 3-Chloroperoxybenzoic acid (383 mg, 1.55 mL)

was dissolved in methylene chloride (3.1 mL) and added via syringe to the stirring solution. The resulting solution was stirred at 25° C. for 1 hour. The solution was then diluted with methylene chloride (15 mL) and washed with saturated sodium bicarbonate followed by brine. The organics were dried over sodium sulfate and concentrated in vacuo to yield 680 mg of the desired product as colorless oil. LCMS (M+1)= 469.40

Example A7.13 tert-Butyl 4-{5-[5-chloropyridin-2-yl)sulfanyl]-4-[4-(methylsulfinyl)phenyl]-1,3-oxazol-2-yl}piperidine-1-carboxylate

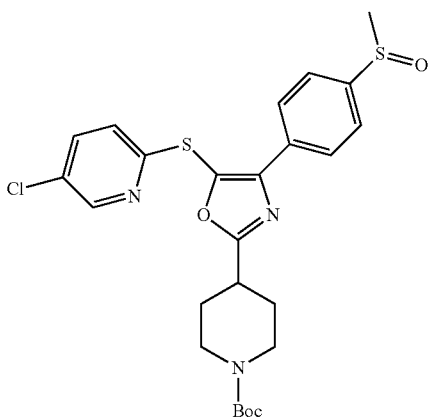 [SMILES: CS(=O)c1ccc(-c2nc(C3CCN(C(=O)OC(C)(C)C)CC3)oc2Sc2ccc(Cl)cn2)cc1]

Intermediate 6.2 (685 mg, 1.46 mmol), 5-chloropyridine-2-thiol (531 mg, 3.65 mmol), and potassium carbonate (605 mg, 4.38 mmol) were dissolved in NMP (14.6 mL) and the resulting solution was heated to 85° C. in a sealed tube for 16 hours. The solution was then cooled to 25° C. and diluted with ethyl acetate and washed with aqueous lithium chloride (×3), dried over sodium sulfate and concentrated in vacuum. The crude oil was purified using silica gel chromatography (100 g, using a 25-100% ethyl acetate in hexane gradient) to afford 658 mg of the desired product as a clear oil. LCMS (M+1)= 534.5.
$^1$H NMR (CDCl$_3$): δ 8.38 (d, J=2.1 Hz, 1H), 8.21 (d, J=6.8 Hz, 2H), 7.7 (d, J=6.8 Hz, 2H), 7.54 (dd, J=8.5 Hz, 2.1 Hz, 1H), 6.94 (d, J=8.5 Hz, 1H), 4.15 (m, 2H), 3.1 (m, 3H), 2.73 (s, 3H), 2.15 (m, 2H), 1.95 (m, 2H), 1.51 (s, 9H).

Example A7.15

4-{5-[(5-Chloropyridin-2-yl)sulfanyl]-4-[4-(methylsulfinyl)phenyl]-1,3-oxazol-2-yl}piperidinium chloride

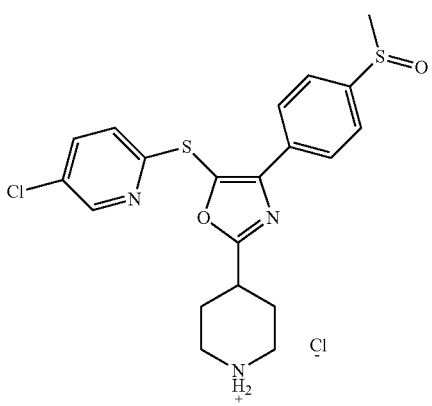 [SMILES: CS(=O)c1ccc(-c2nc(C3CCNCC3)oc2Sc2ccc(Cl)cn2)cc1 ; Cl]

Example A7.13 (850 mg, 1.59 mmol) was dissolved in methylene chloride (15.9 mL) under argon atmosphere. Hydrochloric acid (1.59 mL, 6.37 mmol, 4 M solution) in dioxane was added dropwise to the stirring solution and the resulting solution was stirred for 4 hours at 25° C. The solution was then concentrated in vacuo, diluted with methylene chloride and concentrated a second time in vacuum to afford 725 mg of the desired product as a white solid. LCMS (M+1)= 434.4. $^1$H NMR (CDCl$_3$): δ 8.38 (d, J=2.1 Hz, 1H), 8.21 (d, J=6.8 Hz, 2H), 7.7 (d, J=6.8 Hz, 2H), 7.54 (dd, J=8.5 Hz, 2.1 Hz, 1H), 6.94 (d, J=8.5 Hz, 1H), 3.25 (m, 2H), 3.05 (m, 1H), 2.85 (m, 2H), 2.73 (s, 3H), 2.15 (m, 2H), 1.95 (m, 2H).

Example A7.18

1-(4-{5-[(5-Chloropyridin-2-yl)sulfanyl]-4-[4-(methylsulfinyl)phenyl]-1,3-oxazol-2-yl}piperidin-1-yl)ethanone

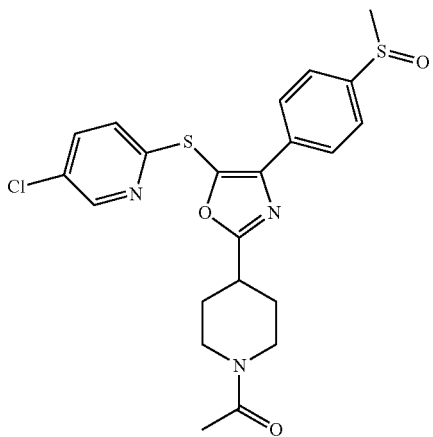 [SMILES: CC(=O)N1CCC(c2nc(-c3ccc(S(C)=O)cc3)c(Sc3ccc(Cl)cn3)o2)CC1]

Example A7.15 (25.0 mg, 0.053 mmol), Hunig's base (12.1 μL, 0.069 mmol), 1-ethyl-3-(3-dimethylaminopropyl)carbodiimide (12.2 mg, 0.064 mmol), 1-hydroxy-7-azabenzotriazole (0.72 mg, 5.3 μmol), and acetic acid (4.5 mg, 0.074 mmol) were dissolved in DMF (1.0 mL) and stirred at 25° C. for 16 hours. The crude mixture was diluted with ethyl acetate and washed with 10% potassium monohydrogen sulfate, saturated sodium bicarbonate, aqueous lithium chloride, dried over sodium sulfate and concentrated in vacuum. The crude product was purified using reverse phase chromatography. The appropriate fractions were extracted into ethyl acetate and washed with saturated sodium bicarbonate and brine to yield 21 mg of clear oil. $^1$H NMR (CDCl$_3$): δ 838 (d, J=2.1 Hz, 1H), 8.21 (d, J=6.8 Hz, 2H), 7.7 (d, J=6.8 Hz, 2H), 7.54 (dd, J=8.5 Hz, 2.1 Hz, 1H), 6.94 (d, J=8.5 Hz, 1H), 4.15 (m, 2H), 3.1 (m, 3H), 2.73 (s, 3H), 2.18 (s, 3H), 2.15 (m, 2H), 1.95 (m, 2H). LCMS (M+1)=476.4.

Example A7.19

5-chloro-2-({4-[4-(methylsulfinyl)phenyl]-2-[1-(methylsulfonyl)piperidin-4-yl]-1,3-oxazol-5-yl}sulfanyl)pyridine

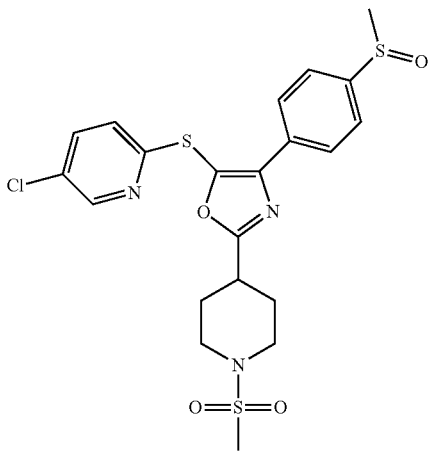 [SMILES: CS(=O)c1ccc(-c2nc(C3CCN(S(C)(=O)=O)CC3)oc2Sc2ccc(Cl)cn2)cc1]

Example A7.15 (25.0 mg, 0.053 mmol) and Hunig's base (11.7 mg, 0.090 mmol) were dissolved in methylene chloride (1.0 mL) under argon atmosphere. Methanesulfonyl chloride (9.1 mg, 0.080 mmol) was added dropwise via syringe and the resulting solution was stirred at 25° C. for 4 hours. The crude mixture was concentrated in vacuo and the crude product was purified using reverse phase chromatograpy. The appropriate fractions were extracted into ethyl acetate and washed with saturated sodium bicarbonate and brine to yield 22.0 mg of clear oil. $^1$H NMR (CDCl$_3$): δ 8.38 (d, J=2.1 Hz, 1H), 8.21 (d, J=6.8 Hz, 2H), 7.7 (d, J=6.8 Hz, 2H), 7.54 (dd, J=8.5 Hz, 2.1 Hz, 1H), 6.94 (d, J=8.5 Hz, 1H), 4.15 (m, 2H), 3.1 (m, 3H), 2.83 (s, 3H), 2.73 (s, 3H), 2.15 (m, 2H), 1.95 (m, 2H). LCMS (M+1)

Example A7.20

5-chloro-2-({2-(1-methylpiperidin-4-yl)-4-[4-(methylsulfinyl)phenyl]-1,3-oxazol-5-yl}sulfanyl)pyridine

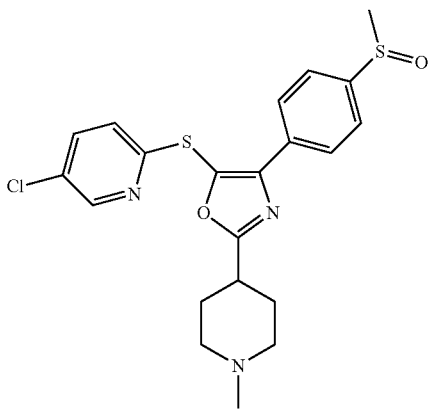 [SMILES: CN1CCC(c2nc(-c3ccc(S(C)=O)cc3)c(Sc3ccc(Cl)cn3)o2)CC1]

Example A7.15 (25.0 mg, 0.053 mmol) and sodium triacetoxyborohydride (28.2 mg, 0.13 mmol) were dissolved in a 2:1 solution of methanol and dichloroethane (1.0 mL). Formaldehyde (39.6 μL, 0.53 mmol, 37% solution in water). The resulting solution was stirred at 25° C. for 16 hours. The solution was diluted with ethyl acetate and washed with 10% potassium monohydrogen sulfate, saturated sodium bicarbonate, dried over sodium sulfate, and concentrated in vacuum. The crude product was purified using reverse phase chromatography. The appropriate fractions were extracted into ethyl acetate and washed with saturated sodium bicarbonate and brine to yield 14 mg of clear oil. $^1$H NMR (CDCl$_3$): δ 8.38 (d, J=2.1 Hz, 1H), 8.21 (d, J=6.8 Hz, 2H), 7.7 (d, J=6.8 Hz, 2H), 7.54 (dd, J=8.5 Hz, 2.1 Hz, 1H), 6.94 (d, J=8.5 Hz, 1H), 4.15 (m, 2H), 3.1 (m, 3H), 2.73 (s, 3H), 2.25 (s, 3H), 2.15 (m, 2H), 1.95 (m, 2H). LCMS (M+1)=448.4.

Intermediate A7.29i

2-Bromoethyl 4-{5-[(5-chloropyridin-2-yl)sulfanyl]-4-[4-(methylsulfinyl)phenyl]-1,3-oxazol-2-yl}piperidine-1-carboxylate

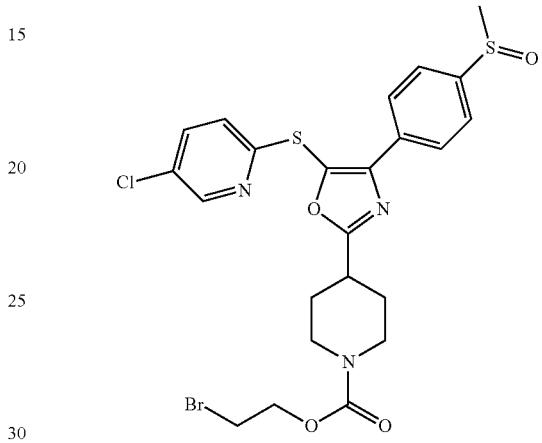

Example A7.15 (175 mg, 0.403 mmol) and Hünig base (62.5 mg, 0.484 mmol) were dissolved in methylene chloride (4.03 ml.) under argon atmosphere. 2-bromoethyl carbonochloridate (83 mg, 0.444 mmol) was added dropwise via syringe to the stirring solution and the resulting solution was stirred for 4 hours at 25° C. The solution was then concentrated in vacuum and the crude product was purified using reverse-phase chromatography. The appropriate fractions were extracted into ethyl acetate and washed with saturated sodium bicarbonate and brine to yield 189 mg of a clear oil. LCMS (M+1)=586.4

Example A7.29

2-(dimethylamino)ethyl 4-{5-[(5-chloropyridin-2-yl)sulfanyl]-4-[4-(methylsulfinyl)phenyl]-1,3-oxazol-2-yl}piperidine-1-carboxylate

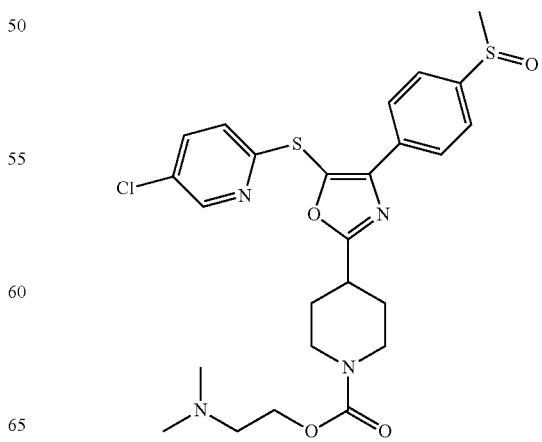

Intermediate A7.29i (60.0 mg, 0.103 mmol), cesium carbonate (33.4 mg, 0.103 mmol), and dimethylamine (205 μL, 0.410 mmol, 2 M solution in methanol) were dissolved in dimethylformamide (1.05 mL). The resulting solution was heated in a sealed tube and heated to 65° C. for 16 hours. The solution was then diluted with ethyl acetate and washed with aqueous lithium chloride. The organics were dried over sodium sulfate and concentrated in vacuo. The crude product was purified using reverse phase chromatography. The appropriate fractions were extracted into ethyl acetate and washed with saturated sodium bicarbonate and brine to yield 43 mg of a clear oil. $^1$H NMR (CDCl$_3$): δ 8.38 (d, J=2.1 Hz, 1H), 8.21 (d, J=6.8 Hz, 2H), 7.7 (d, J=6.8 Hz, 2H), 7.54 (dd, J=8.5 Hz, 2.1 Hz, 1H), 6.94 (d, J=8.5 Hz, 1H), 4.23 (t, J=5.8 Hz, 2H), 4.15 (m, 2H), 3.1 (m, 3H), 2.73 (s, 3H), 2.6 (t, J=5.8 Hz, 2H), 2.32 (s, 6H), 2.15 (m, 2H), 1.95 (m, 2H). LCMS (M+1)= 549.5.

Intermediate A6.3 tert-Butyl 4-[5-bromo-2-(tetrahydro-2H-pyran-4-yl)-1,3-oxazol-4-yl]piperidine-1-carboxylate

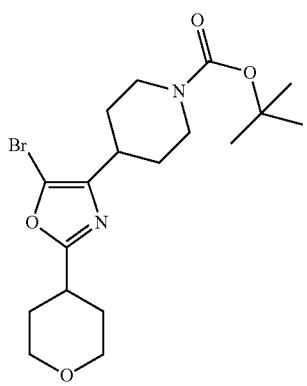

Step A6.3-1: tert-Butyl 4-[2-(tetrahydro-2H-pyran-4-yl)-1,3-oxazol-4-yl]piperidine-1-carboxylate

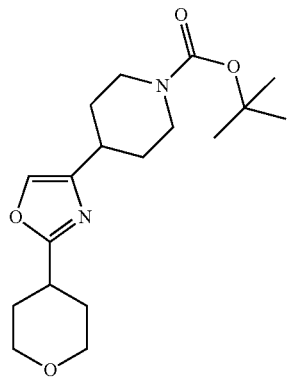 [SMILES: CC(C)(C)OC(=O)N1CCC(c2coc(C3CCOCC3)n2)CC1]

tert-Butyl 4-(bromoacetyl)piperidine-1-carboxylate (1.07 g, 3.49 mmol) and tetrahydro-2H-pyran-4-carboxamide (0.95 g, 7.36 mmol) were mixed heated in DMPU (6.99 mL) at 150° C. for 4 hrs. LC-MS indicated that the reaction was completed and the product showed loss of Boc group. Et$_3$N (1.46 mL, 10.5 mol) and Boc$_2$O (0.915 g, 4.19 mmol) were added and the mixture was stirred at RT for 30 min. The reaction was diluted with water and dichloromethane. The two layers were separated and the organic layer was extracted with dichloromethane. The combined organic layers were washed with H$_2$O (twice) and brine, dried over Na$_2$SO$_4$, filtered and conc. The crude (still containing DMPU) was used without purification. LC-MS: [M+H]$^+$=337.4.

Step A6.3-2: tert-Butyl 4-[5-bromo-2-(tetrahydro-2H-pyran-4-yl)-1,3-oxazol-4-yl]piperidine-1-carboxylate

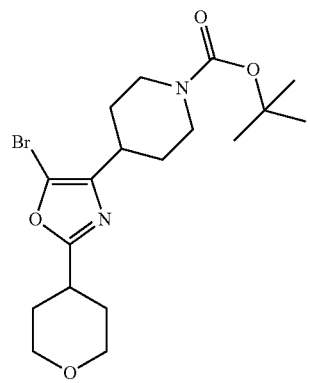 [SMILES: CC(C)(C)OC(=O)N1CCC(c2nc(C3CCOCC3)oc2Br)CC1]

Br$_2$ (0.181 ml, 3.51 mmol) was added to a stirred mixture of Reactant 2 (1.18 g, 3.51 mmol) in CHCl$_3$ (17.54 ml) and the mixture was stirred at room temperature for 1 h. The reaction was diluted with CH$_2$Cl$_2$ and washed with H$_2$O (2×) and brine. The organic layer was dried over Na$_2$SO$_4$, filtered and conc. The residue was purified by silica gel flash column (0-50% EtOAc in hex). [M+H]$^+$=415.3.

Intermediate A7.31i tert-Butyl 4-{5-[(5-chloropyridin-2-yl)sulfanyl]-2-(tetrahydro-2H-pyran-4-yl)-1,3-oxazol-4-yl}piperidine-1-carboxylate

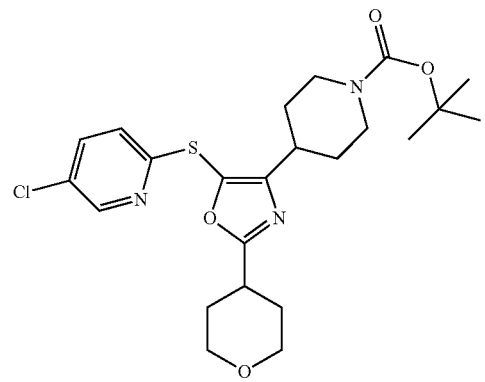 [SMILES: CC(C)(C)OC(=O)N1CCC(c2nc(C3CCOCC3)oc2Sc2ccc(Cl)cn2)CC1]

A mixture of the bromide intermediate A6.3 (593 mg, 1.43 mol), 5-chloropyridine-2-thiol (249 mg, 1.71 mol), K$_3$PO$_4$ (758 mmol, 3.57 mmol), N,N-dimethylglycine (29 mg, 0.286 mmol) and CuI (54 mg, 0.286 mmol) in DMF (7.14 mL) was heated at 145° C. for 5 h. A second portion of reagents except of K$_3$PO$_4$ was added and the reaction continued overnight.

The reaction was diluted with H₂O and extracted with CH₂Cl₂. The combined organic layers were dried (Na₂SO₄), filtered and conc. The residue was purified by ISCO (0-50% of EtOAc in hex). [M+H]⁺=480.4.

Example A7.31

5-chloro-2-{[4-(piperidin-4-yl)-2-(tetrahydro-2H-pyran-4-yl)-1,3-oxazol-5-yl]sulfanyl}pyridine

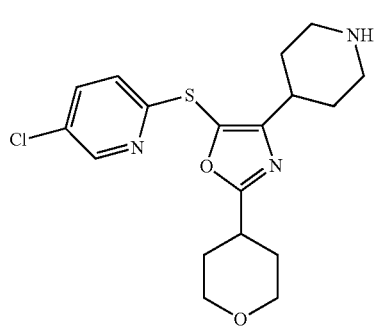 [SMILES: Clc1ccc(Sc2oc(C3CCOCC3)nc2C2CCNCC2)nc1]

TFA (1 mL, 12.98 mmol) was added to a stirred solution of the above intermediate A7.21 (334 mg, 0.696 mmol) in DCM (10 mL) and the mixture was stirred at room temperature for 1 h. The solvent was removed and the residue was purified by reverse-phase HPLC. NMR (CDCl₃, 400 MHz) δ 9.46 (bs, 1H), 8.92 (bs, 1H), 8.35 (d, J=2.8 Hz, 1H), 7.54 (dd, J=2.8, 8.4 Hz, 1H), 6.91 (d, J=8.4 Hz, 1H), 4.02 (td, J=3.6, 8.4 Hz, 2H), 3.57 (dt, J=3.6, 11.6 Hz, 3H), 3.09-3.01 (m, 3H), 2.21-2.12 (m, 2H), 2.07-1.86 (m, 8H). FIRMS (ES) [M+1]⁺ calcd for C₁₈H₂₃ClN₃O₂S: 380.1194. Found: 380.1198.

Example A7.32

Methyl 4-{5-[(5-chloropyridin-2-yl)sulfanyl]-2-(tetrahydro-2H-pyran-4-yl)-1,3-oxazol-4-yl}piperidine-1-carboxylate

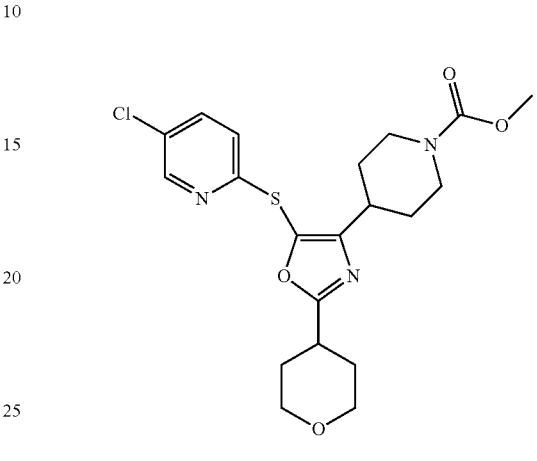

To a stirring solution of example A7.22 hydrochloride chloride (20 mg, 0.048 mmol) in chloroform (320 μl) was added saturated aqueous sodium bicarbonate (160 μl) followed by methyl chloroformate (4.46 μl, 0.058 mmol). After two minutes, the organic layer was removed and the solvent was evaporated under an air stream. The title compound was isolated by preparative HPLC (18 mg, 86%). ¹H NMR (CDCl₃, 400 MHz) δ 8.36 (dd, J=0.73, 2.56 Hz, 1H), 7.51 (dd, J=2.56, 8.42 Hz, 1H), 6.81 (dd, J=0.73, 8.42 Hz, 1H), 4.02 (dt, J=3.48, 11.54 Hz, 2H), 3.68 (s, 3H), 3.51 (td, J=2.93, 10.80 Hz, 2H), 3.04-3.11 (m, 1H), 2.81-2.90 (m, 4H), 1.90-2.00 (m, 5H), 1.75-1.90 (m, 2H), 1.68 (m, 2H). HRMS [M+1]⁺ Calculated: 438.1249, Measured: 438.1250.

| Ex # | Structure | IUPAC name | M + 1 |
|---|---|---|---|
| A7.1 | 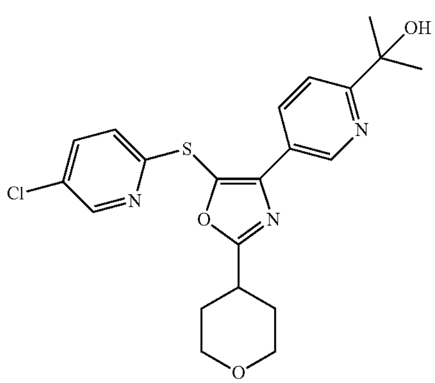 [SMILES: CC(C)(O)c1ccc(-c2nc(C3CCOCC3)oc2Sc2ccc(Cl)cn2)cn1] | 2-(5-{5-[(5-chloropyridin-2-yl)sulfanyl]-2-(tetrahydro-2H-pyran-4-yl)-1,3-oxazol-4-yl}pyridin-2-yl)propan-2-ol | 432.4 |

| Ex # | Structure | IUPAC name | M + 1 |
|---|---|---|---|
| A7.2 | 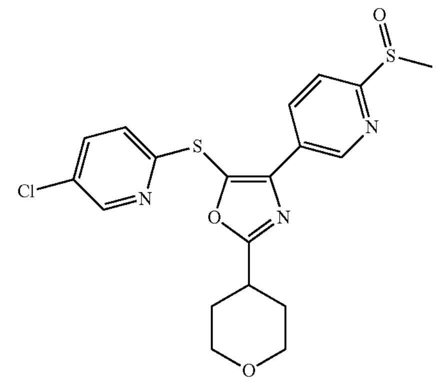 [SMILES: CS(=O)c1ccc(-c2nc(C3CCOCC3)oc2Sc2ccc(Cl)cn2)cn1] | 5-chloro-2-({4-[6-(methylsulfinyl)pyridin-3-yl]-2-(tetrahydro-2H-pyran-4-yl)-1,3-oxazol-5-yl}sulfanyl)pyridine | 436.3 |
| A7.3 | 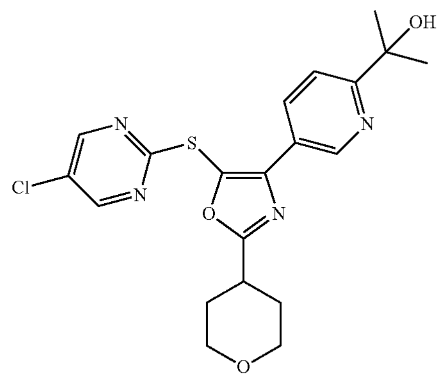 | 2-(5-{5-[(5-chloropyrimidin-2-yl)sulfanyl]-2-(tetrahydro-2H-pyran-4-yl)-1,3-oxazol-4-yl}pyridin-2-yl)propan-2-ol | 433.3 |
| A7.4 | 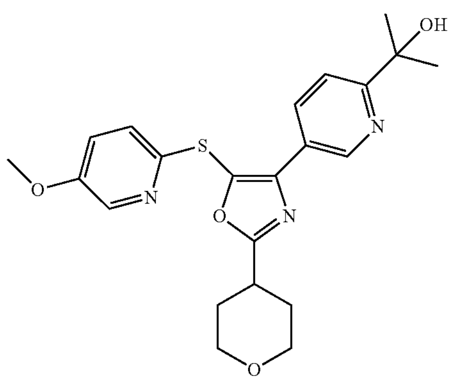 [SMILES: COc1ccc(Sc2oc(C3CCOCC3)nc2-c2ccc(C(C)(C)O)nc2)nc1] | 2-(5-{5-[(5-methoxypyridin-2-yl)sulfanyl]-2-(tetrahydro-2H-pyran-4-yl)-1,3-oxazol-4-yl}pyridin-2-yl)propan-2-ol | 428.3 |
| A7.5 | 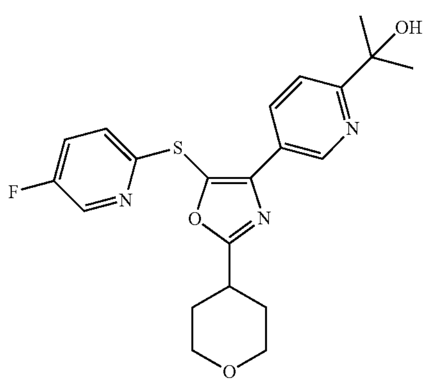 [SMILES: CC(C)(O)c1ccc(-c2nc(C3CCOCC3)oc2Sc2ccc(F)cn2)cn1] | 2-(5-{5-[(5-fluoropyridin-2-yl)sulfanyl]-2-(tetrahydro-2H-pyran-4-yl)-1,3-oxazol-4-yl}pyridin-2-yl)propan-2-ol | 416.3 |

| Ex # | Structure | IUPAC name | M + 1 |
| --- | --- | --- | --- |
| A7.6 | 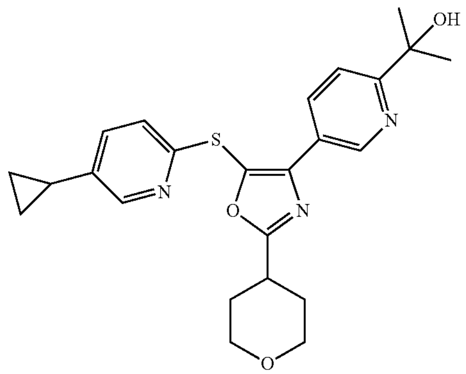 [SMILES: CC(C)(O)c1ccc(-c2nc(C3CCOCC3)oc2Sc2ccc(C3CC3)cn2)cn1] | 2-(5-{5-{(5-cyclopropylpyridin-2-yl)sulfanyl]-2-(tetrahydro-2H-pyran-4-yl)-1,3-oxazol-4-yl}pyridin-2-yl)propan-2-ol | 438.3 |
| A7.7 | 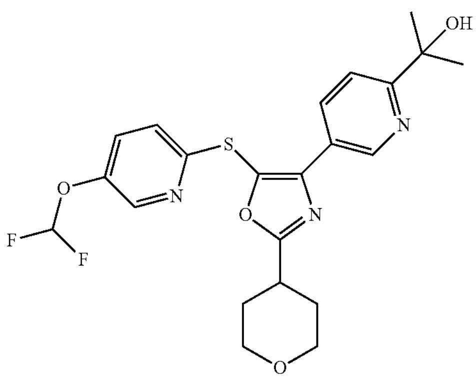 [SMILES: CC(C)(O)c1ccc(-c2nc(C3CCOCC3)oc2Sc2ccc(OC(F)F)cn2)cn1] | 2-{5-[5-{[5-(difluoromethoxy)pyridin-2-yl]sulfanyl}-2-(tetrahydro-2H-pyran-4-yl)-1,3-oxazol-4-yl]pyridin-2-yl}propan-2-ol | 464.3 |
| A7.8 | 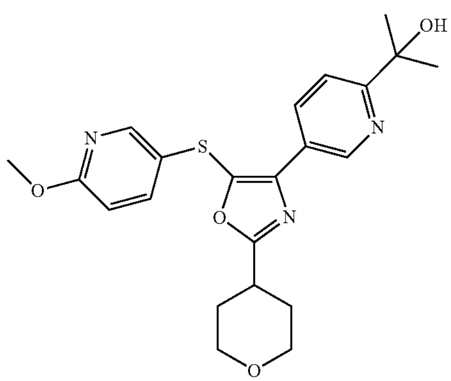 [SMILES: COc1ccc(Sc2oc(C3CCOCC3)nc2-c2ccc(C(C)(C)O)nc2)cn1] | 2-(5-{5-{(6-methoxypyridin-3-yl)sulfanyl]-2-(tetrahydro-2H-pyran-4-yl)-1,3-oxazol-4-yl}pyridin-2-yl)propan-2-ol | 428.3 |
| A7.9 | 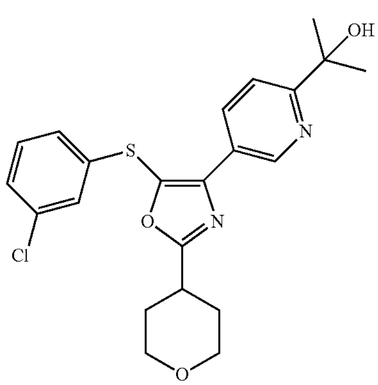 [SMILES: CC(C)(O)c1ccc(-c2nc(C3CCOCC3)oc2Sc2cccc(Cl)c2)cn1] | 2-(5-{5-[(3-chlorophenyl)sulfanyl]-2-(tetrahydro-2H-pyran-4-yl)-1,3-oxazol-4-yl}pyridin-2-yl)propan-2-ol | 431.3 |

| Ex # | Structure | IUPAC name | M + 1 |
|---|---|---|---|
| A7.10 | 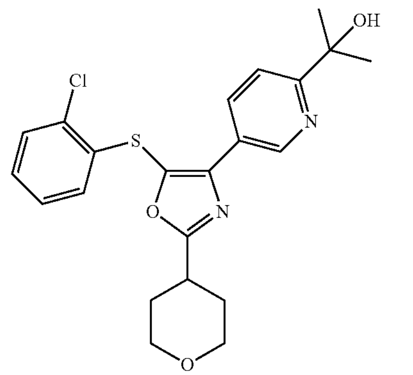 [SMILES: CC(C)(O)c1ccc(-c2nc(C3CCOCC3)oc2Sc2ccccc2Cl)cn1] | 2-(5-{5-[(2-chlorophenyl)sulfanyl]-2-(tetrahydro-2H-pyran-4-yl)-1,3-oxazol-4-yl}pyridin-2-yl)propan-2-ol | 431.3 |
| A7.11 | 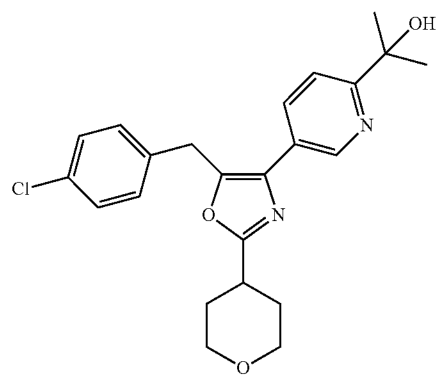 [SMILES: CC(C)(O)c1ccc(-c2nc(C3CCOCC3)oc2Cc2ccc(Cl)cc2)cn1] | 2-{5-[5-(4-chlorobenzyl)-2-(tetrahydro-2H-pyran-4-yl)-1,3-oxazol-4-yl]pyridin-2-yl}propan-2-ol | 413.2 |
| A7.12 | 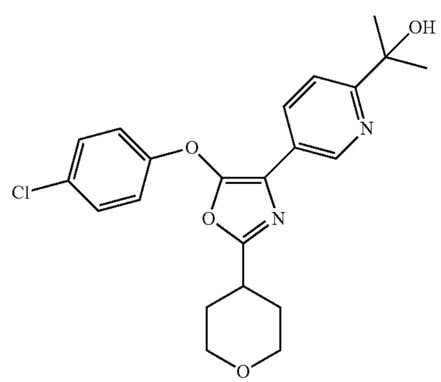 | 2-{5-[5-(4-chlorophenoxy)-2-(tetrahydro-2H-pyran-4-yl)-1,3-oxazol-4-yl]pyridin-2-yl}propan2-ol | 415.3 |
| A7.13 | 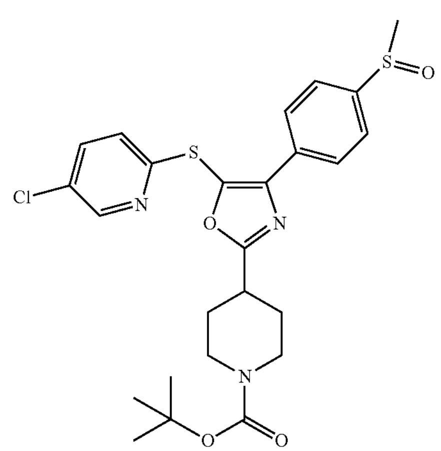 [SMILES: CS(=O)c1ccc(-c2nc(C3CCN(C(=O)OC(C)(C)C)CC3)oc2Sc2ccc(Cl)cn2)cc1] | tert-butyl 4-{5-[(5-chloropyridin-2-yl)sulfanyl]-4-[4-(methylsulfinyl)phenyl]-1,3-oxazol-2-yl}piperidine-1-carboxylate | 534.5 |

-continued

| Ex # | Structure | IUPAC name | M + 1 |
|---|---|---|---|
| A7.14 | 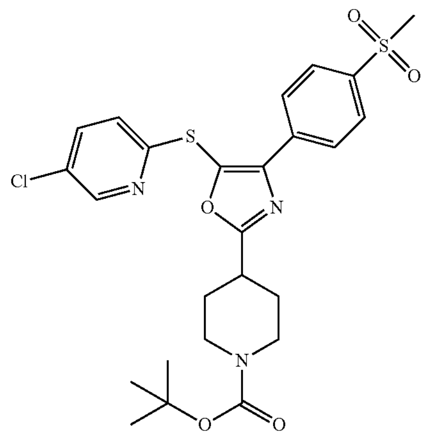 [SMILES: CC(C)(C)OC(=O)N1CCC(c2nc(-c3ccc(S(C)(=O)=O)cc3)c(Sc3ccc(Cl)cn3)o2)CC1] | tert-butyl 4-{5-[(5-chloropyridin-2-yl)sulfanyl]-4-[4-(methylsulfonyl)phenyl]-1,3-oxazol-2-yl}piperidine-1-carboxylate | 550.1 |
| A7.15 | 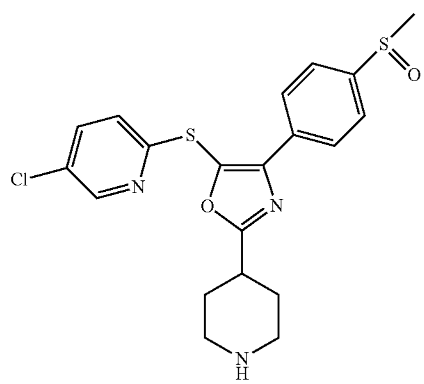 [SMILES: CS(=O)c1ccc(-c2nc(C3CCNCC3)oc2Sc2ccc(Cl)cn2)cc1] | 5-chloro-2-({4-[4-(methylsulfinyl)phenyl]-2-(piperidin-4-yl)-1,3-oxazol-5-yl}sulfanyl)pyridine | 434.4 |
| A7.16 | 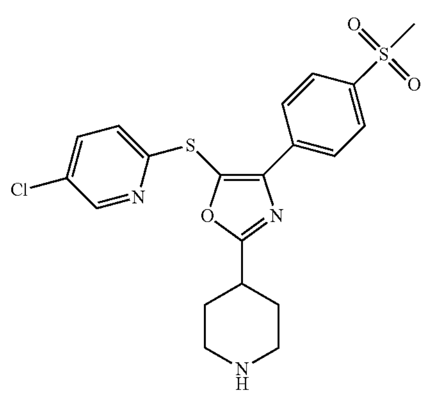 [SMILES: CS(=O)(=O)c1ccc(-c2nc(C3CCNCC3)oc2Sc2ccc(Cl)cn2)cc1] | 5-chloro-2-({4-[4-(methylsulfonyl)phenyl]-2-(piperidin-4-yl)-1,3-oxazol-5-yl}sulfanyl)pyridine | 450.1 |

| Ex # | Structure | IUPAC name | M + 1 |
|---|---|---|---|
| A7.17 | 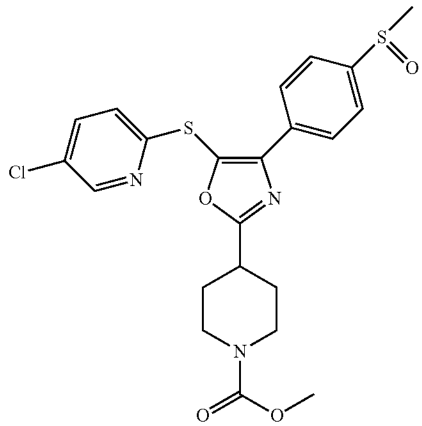 [SMILES: COC(=O)N1CCC(c2nc(-c3ccc(S(C)=O)cc3)c(Sc3ccc(Cl)cn3)o2)CC1] | methyl 4-{5-[(5-chloropyridin-2-yl)sulfanyl]-4-[4-(methylsulfinyl)phenyl]-1,3-oxazol-2-yl}piperidine-1-carboxylate | 492.1 |
| A7.18 | 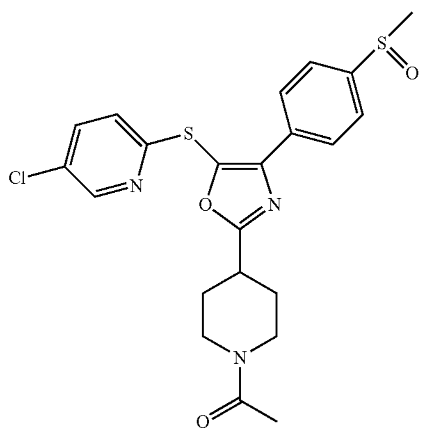 [SMILES: CC(=O)N1CCC(c2nc(-c3ccc(S(C)=O)cc3)c(Sc3ccc(Cl)cn3)o2)CC1] | 1-(4-{5-[(5-chloropyridin-2-yl)sulfanyl]-4-[4-methylsulfinyl)phenyl]-1,3-oxazol-2-yl}piperidin-1-yl)ethanone | 476.4 |
| A7.19 | 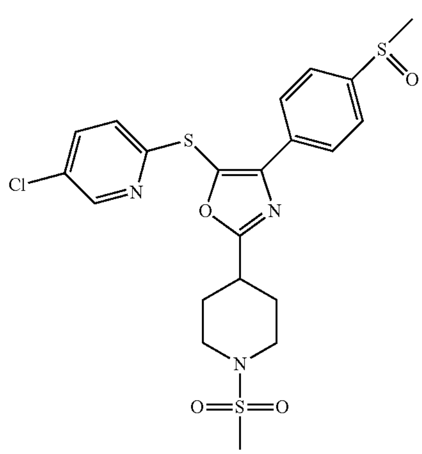 [SMILES: CS(=O)c1ccc(-c2nc(C3CCN(S(C)(=O)=O)CC3)oc2Sc2ccc(Cl)cn2)cc1] | 5-chloro-2-({4-[4-(methylsulfinyl)phenyl]-2-[1-(methylsulfonyl)piperidin-4-yl]-1,3-oxazol-5-yl}sulfanyl)pyridine | 512.4 |

| Ex # | Structure | IUPAC name | M + 1 |
| --- | --- | --- | --- |
| A7.20 | 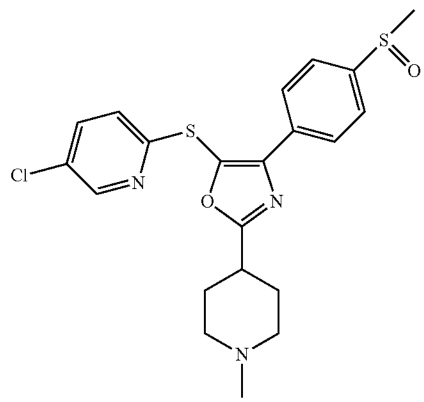 [SMILES: CN1CCC(c2nc(-c3ccc(S(C)=O)cc3)c(Sc3ccc(Cl)cn3)o2)CC1] | 5-chloro-2-({2-(1-methylpiperidin-4-yl)-4-[4-(methylsulfinyl)phenyl]-1,3-oxazol-5-yl}sulfanyl)pyridine | 448.4 |
| A7.21 | 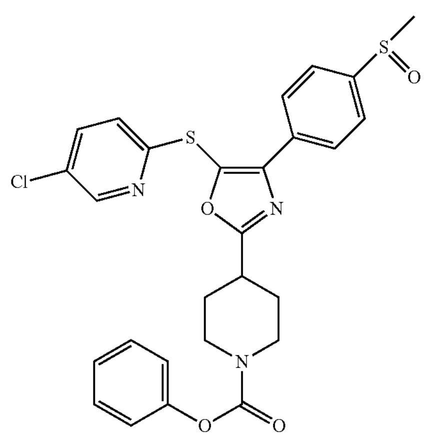 [SMILES: CS(=O)c1ccc(-c2nc(C3CCN(C(=O)Oc4ccccc4)CC3)oc2Sc2ccc(Cl)cn2)cc1] | phenyl 4-{5-[(5-chloropyridin-2-yl)sulfanyl]-4-[4-(methylsulfinyl)phenyl]-1,3-oxazol-2-yl}piperidine-1-carboxylate | 554.1 |
| A7.22 | 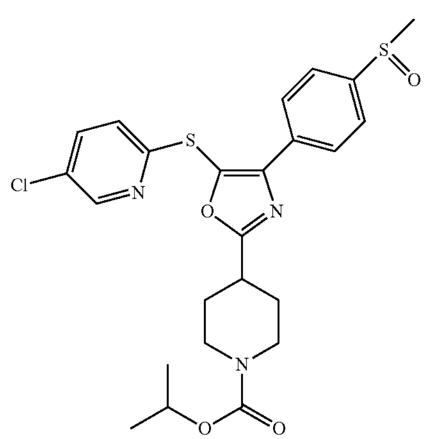 [SMILES: CC(C)OC(=O)N1CCC(c2nc(-c3ccc(S(C)=O)cc3)c(Sc3ccc(Cl)cn3)o2)CC1] | propan-2-yl 4-{5-[(5-chloropyridin-2-yl)sulfanyl]-4-[4-(methylsulfinyl)phenyl]-1,3-oxazol-2-yl}piperidine-1-carboxylate | 520.1 |

| Ex # | Structure | IUPAC name | M + 1 |
|---|---|---|---|
| A7.23 | 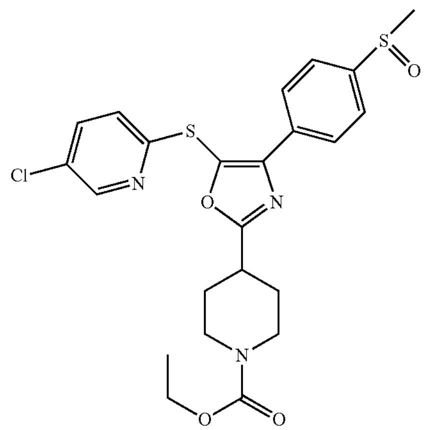 [SMILES: CCOC(=O)N1CCC(c2nc(-c3ccc(S(C)=O)cc3)c(Sc3ccc(Cl)cn3)o2)CC1] | ethyl 4-{5-[(5-chloropyridin-2-yl)sulfanyl]-4-[4-(methylsulfinyl)phenyl]-1,3-oxazol-2-yl}piperidine-1-carboxylate | 506.1 |
| A7.24 | 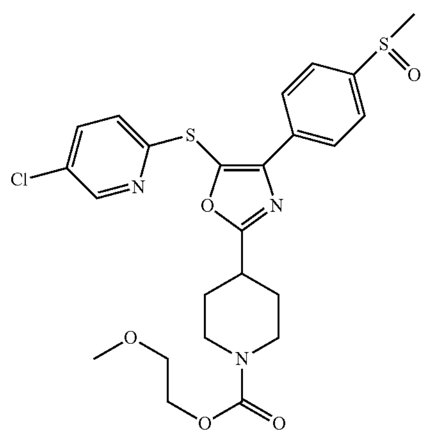 [SMILES: COCCOC(=O)N1CCC(c2nc(-c3ccc(S(C)=O)cc3)c(Sc3ccc(Cl)cn3)o2)CC1] | 2-methoxyethyl 4-{5-[(5-chloropyridin-2-yl)sulfanyl]-4-[4-(methylsulfinyl)phenyl]-1,3-oxazol-2-yl}piperidine-1-carboxylate | 536.1 |
| A7.25 | 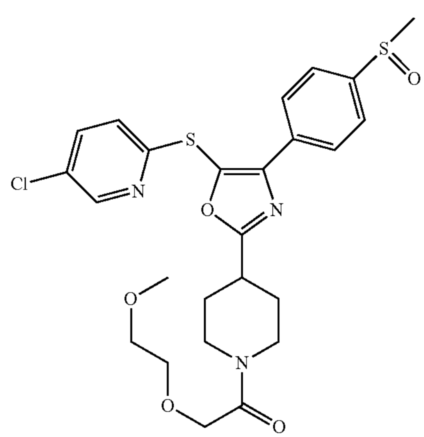 [SMILES: COCCOCC(=O)N1CCC(c2nc(-c3ccc(S(C)=O)cc3)c(Sc3ccc(Cl)cn3)o2)CC1] | 1-(4-{5-[(5-chloropyridin-2-yl)sulfanyl]-4-[4-(methylsulfinyl)phenyl]-1,3-oxazol-2-yl}piperidin-1-yl)-2-(2-methoxyethoxy)ethanone | 550.1 |

| Ex # | Structure | IUPAC name | M + 1 |
| --- | --- | --- | --- |
| A7.26 | 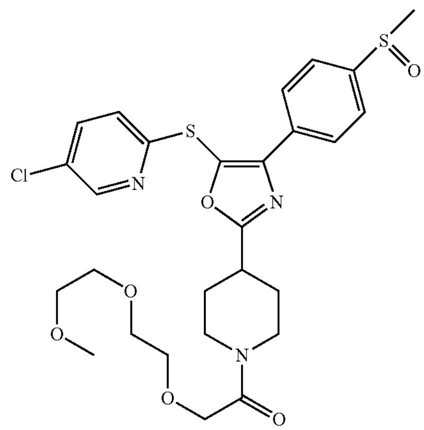 [SMILES: COCCOCCOCC(=O)N1CCC(c2nc(-c3ccc(S(C)=O)cc3)c(Sc3ccc(Cl)cn3)o2)CC1] | 1-(4-{5-[(5-chloropyridin-2-yl)sulfanyl]-4-[4-(methylsulfinyl)phenyl]-1,3-oxazol-2-yl}piperidin-1-yl)-2-[2-(2-methoxyethoxy)ethoxy]ethanone | 594.2 |
| A7.27 | 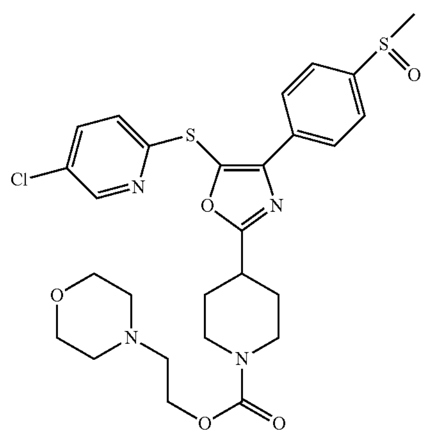 [SMILES: CS(=O)c1ccc(-c2nc(C3CCN(C(=O)OCCN4CCOCC4)CC3)oc2Sc2ccc(Cl)cn2)cc1] | 2-(morpholin-4-yl)ethyl 4-{5-[(5-chloropyridin-2-yl)sulfanyl]-4-[4-(methylsulfinyl)phenyl]-1,3-oxazol-2-yl}piperidine-1-carboxylate | 591.2 |
| A7.28 | 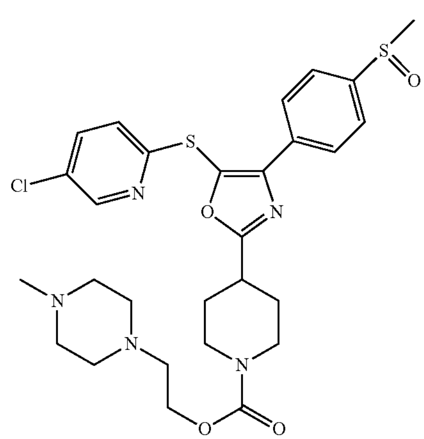 [SMILES: CN1CCN(CCOC(=O)N2CCC(c3nc(-c4ccc(S(C)=O)cc4)c(Sc4ccc(Cl)cn4)o3)CC2)CC1] | 2-(4-methylpiperazin-1-yl)ethyl 4-{5-[(5-chloropyridin-2-yl)sulfanyl]-4-[4-(methylsulfinyl)phenyl]-1,3-oxazol-2-yl}piperidine-1-carboxylate | 549.1 |

| Ex # | Structure | IUPAC name | M + 1 |
| --- | --- | --- | --- |
| A7.29 | 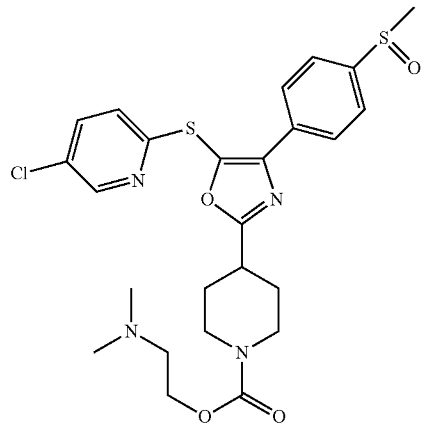 [SMILES: CN(C)CCOC(=O)N1CCC(c2nc(-c3ccc(S(C)=O)cc3)c(Sc3ccc(Cl)cn3)o2)CC1] | 2-(dimethylamino)ethyl 4-{5-[(5-chloropyridin-2-yl)sulfanyl]-4-[4-(methylsulfinyl)phenyl]-1,3-oxazol-2-yl}piperidine-1-carboxylate | 549.5 |
| A7.30 | 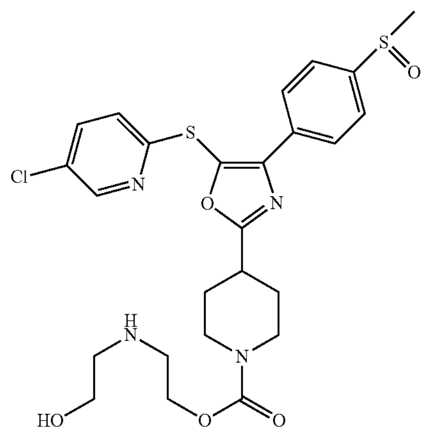 [SMILES: CS(=O)c1ccc(-c2nc(C3CCN(C(=O)OCCNCCO)CC3)oc2Sc2ccc(Cl)cn2)cc1] | 2-[(2-hydroxyethyl)amino]ethyl 4-{5-[(5-chloropyridin-2-yl)sulfanyl]-4-[4-(methylsulfinyl)phenyl]-1,3-oxazol-2-yl}piperidine-1-carboxylate | 565.1 |
| A7.31 | 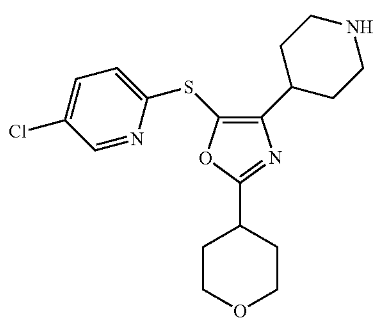 [SMILES: Clc1ccc(Sc2oc(C3CCOCC3)nc2C2CCNCC2)nc1] | 5-chloro-2-{[4-(piperidin-4-yl)-2-(tetrahydro-2H-pyran-4-yl)-1,3-oxazol-5-yl]sulfanyl}pyridine | 380.3 |
| A7.32 | 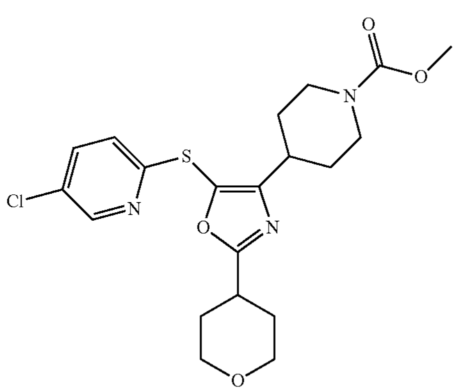 [SMILES: COC(=O)N1CCC(c2nc(C3CCOCC3)oc2Sc2ccc(Cl)cn2)CC1] | methyl 4-{5-[(5-chloropyridin-2-yl)sulfanyl]-2-(tetrahydro-2H-pyran-4-yl)-1,3-oxazol-4-yl}piperidine-1-carboxylate | 438.1 |

| Ex # | Structure | IUPAC name | M + 1 |
| --- | --- | --- | --- |
| A7.33 | 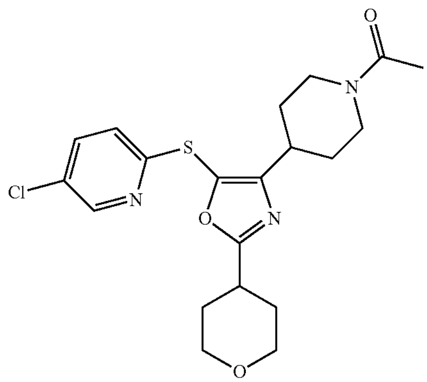 [SMILES: CC(=O)N1CCC(c2nc(C3CCOCC3)oc2Sc2ccc(Cl)cn2)CC1] | 1-(4-{5-[(5-chloropyridin-2-yl)sulfanyl]-2-(tetrahydro-2H-pyran-4-yl)-1,3-oxazol-4-yl}piperidin-1-yl)ethanone | 422.1 |
| A7.34 | 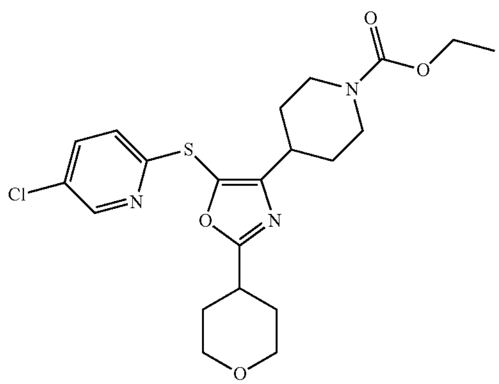 [SMILES: CCOC(=O)N1CCC(c2nc(C3CCOCC3)oc2Sc2ccc(Cl)cn2)CC1] | ethyl 4-{5-[(5-chloropyridin-2-yl)sulfanyl]-2-(tetrahydro-2H-pyran-4-yl)-1,3-oxazol-4-yl}piperidine-1-carboxylate | 452.1 |
| A7.35 | 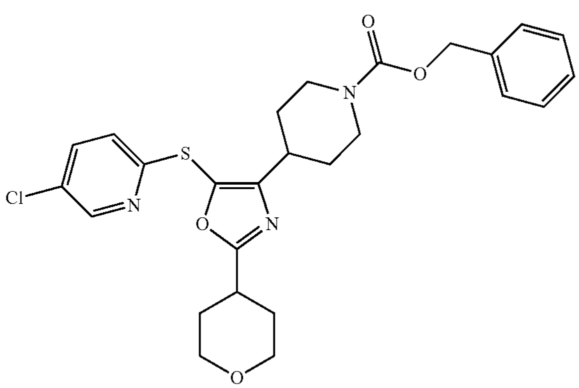 [SMILES: O=C(OCc1ccccc1)N1CCC(c2nc(C3CCOCC3)oc2Sc2ccc(Cl)cn2)CC1] | benzyl 4-{5-[(5-chloropyridin-2-yl)sulfanyl]-2-(tetrahydro-2H-pyran-4-yl)-1,3-oxazol-4-yl}piperidine-1-carboxylate | 514.2 |
| A7.36 | 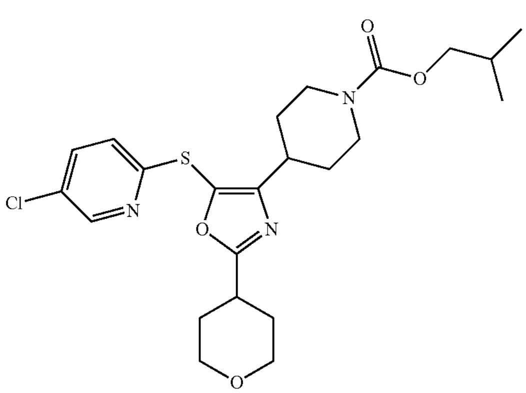 [SMILES: CC(C)COC(=O)N1CCC(c2nc(C3CCOCC3)oc2Sc2ccc(Cl)cn2)CC1] | 2-methylpropyl 4-{5-[(5-chloropyridin-2-yl)sulfanyl]-2-(tetrahydro-2H-pyran-4-yl)-1,3-oxazol-4-yl}piperidine-1-carboxylate | 480.2 |

| Ex # | Structure | IUPAC name | M + 1 |
| --- | --- | --- | --- |
| A7.37 | 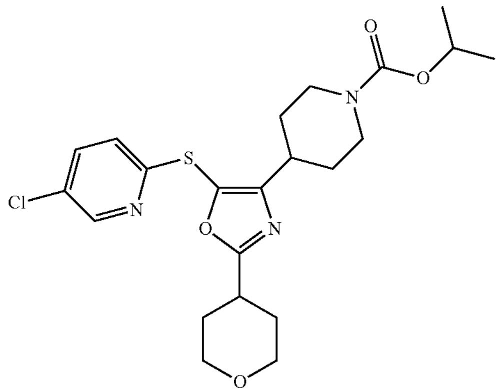 [SMILES: CC(C)OC(=O)N1CCC(c2nc(C3CCOCC3)oc2Sc2ccc(Cl)cn2)CC1] | propan-2-yl 4-{5-[(5-chloropyridin-2-yl)sulfanyl]-2-(tetrahydro-2H-pyran-4-yl)-1,3-oxazol-4-yl}piperidine-1-carboxylate | 466.2 |
| A7.38 | 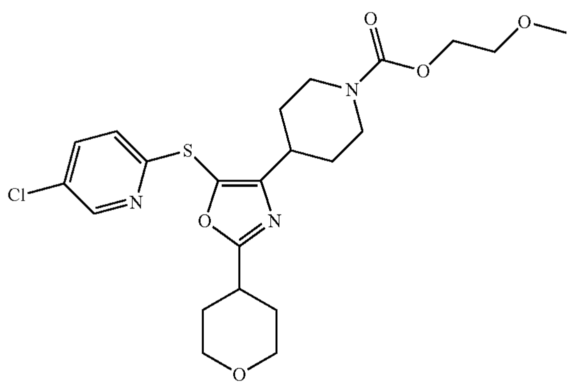 [SMILES: COCCOC(=O)N1CCC(c2nc(C3CCOCC3)oc2Sc2ccc(Cl)cn2)CC1] | 2-methoxyethyl 4-{[5-[(5-chloropyridin-2-yl)sulfanyl]-2-(tetrahydro-2H-pyran-4-yl)-1,3-oxazol-4-yl}piperidine-1-carboxylate | 482.2 |
| A7.39 | 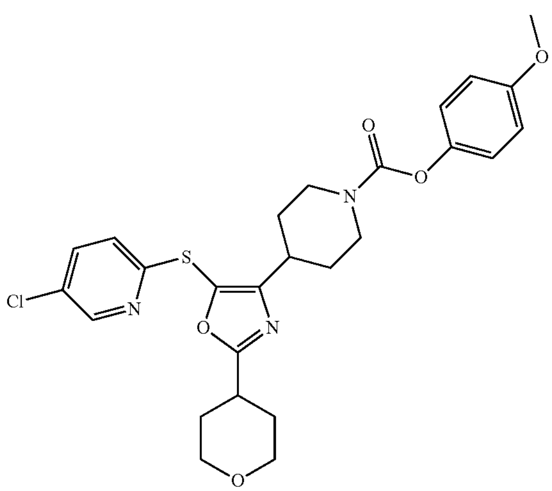 [SMILES: COc1ccc(OC(=O)N2CCC(c3nc(C4CCOCC4)oc3Sc3ccc(Cl)cn3)CC2)cc1] | 4-methoxyphenyl 4-{5-[(5-chloropyridin-2-yl)sulfanyl]-2-(tetrahydro-2H-pyran-4-yl)-1,3-oxazol-4-yl}piperidine-1-carboxylate | 530.2 |

| Ex # | Structure | IUPAC name | M + 1 |
|---|---|---|---|
| A7.40 | 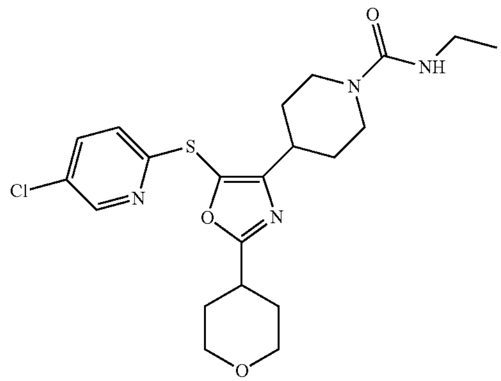 [SMILES: CCNC(=O)N1CCC(c2nc(C3CCOCC3)oc2Sc2ccc(Cl)cn2)CC1] | 4-{5-[(5-chloropyridin-2-yl)sulfanyl]-2-(tetrahydro-2H-pyran-4-yl)-1,3-oxazol-4-yl}-N-ethylpiperidine-1-carboxamide | 451.2 |

Intermediate B4.1

4-bromo-5-[(4-chlorophenyl)sulfanyl]-2-(tetrahydro-2H-pyran-4-yl)-1,3-oxazole

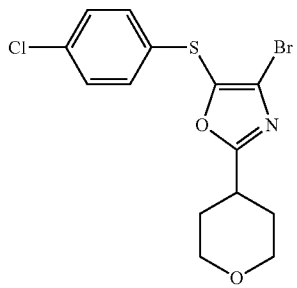 [SMILES: Clc1ccc(Sc2oc(C3CCOCC3)nc2Br)cc1]

Step B.4-1: N-{2-[(4-chlorophenyl)sulfanyl]ethyl}tetrahydro-2H-pyran-4-carboxamide

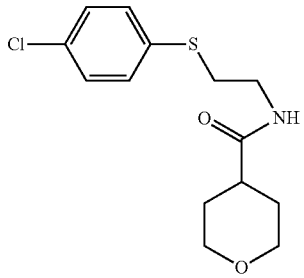 [SMILES: O=C(NCCSc1ccc(Cl)cc1)C1CCOCC1]

To a solution of 2-[(4-chlorophenyl)sulfanyl]ethanamine (15.32 g, 82 mmol, prepared from 4-chlorothiophenol and 2-chloroethylamine as described before) in DMF (247 ml) was added sequentially tetrahydro-2H-pyran-4-carboxylic acid (9.66 g, 74.2 mmol), EDC (15.65 g, 82 mmol) and HOAt (2.021 g, 14.85 mmol) and the reaction mixture was stirred at RT overnight. The reaction mixture was diluted with EtOAc, washed with 1N HCl, aq NaHCO₃, 3M LiCl, dried over sodium sulfate, concentrated in vacuo and purified by flash chromatography (silica 1 kg, 50 to 100% EtOAc in hexane), to give N-{2-[(4-chlorophenyl)sulfanyl]ethyl}tetrahydro-2H-pyran-4-carboxamide (1825 g). MS: M+H=300. H¹NMR (400 MHz, CDCl₃) δ: 7.31 (d, J=9.9 Hz, 2H), 7.26 (d, J=9.9 Hz, 2H), 5.82 (br s, 1 H), 4.40-3.96 (m, 2H), 3.46 (dt, J=7.0, 7.0 Hz, 2H), 3.45-3.36 (m, 2H), 3.05 (t, J=7.0 Hz, 2 H), 2.34-2.26 (m, 1H), 1.82-1.65 (m, 4H).

Step B4.1-2: 5-[(4-chlorophenyl)sulfanyl]-2-(tetrahydro-2H-pyran-4-yl)-1,3-oxazole

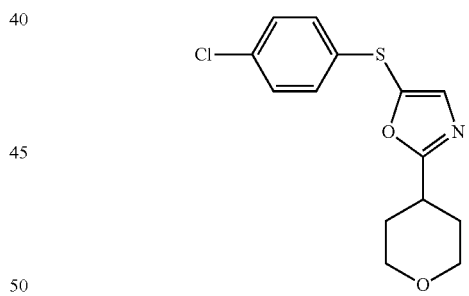

To a solution of N-{2-[(4-chlorophenyl)sulfanyl]ethyl}tetrahydro-2H-pyran-4-carboxamide (9.48 g, 31.6 mmol) in chlorobenzene (316 ml) was added NCS (8.44 g, 63.2 mmol) by portions and the reaction mixture was stirred at RT for 1 h. TFA (1.218 ml, 15.81 mmol) was added and the reaction mixture was stirred at RT for 16 h. The reaction mixture was diluted with DCM, washed with aq NaHCO₃, dried over sodium sulfate, concentrated in vacuo and purified by flash chromatography (silica 2×330 g, 0 to 50% EtOAc in hexane), to give 5-[(4-chlorophenyl)sulfanyl]-2-(tetrahydro-2 H-pyran-4-yl)-1,3-oxazole (7.45 g) as a white solid. MS: M+H=296. H'NMR (400 MHz, CDCl₃) δ: 7.27 (d, J=10.3 Hz, 2 H), 7.26 (s, 1 H), 7.17 (d, J=10.3 Hz, 2 H), 4.01

(dt, J=33, 12.2 Hz, 2 H), 3.51 (td, J=3.7, 12.2 Hz, 2 H), 3.10-3.00 (m, 1 H), 2.04-1.85 (m, 4 H).

Step B4.1-3: 4-Bromo-5-[(4-chlorophenyl)sulfanyl]-2-(tetrahydro-2H-pyran-4-yl)-1,3-oxazole

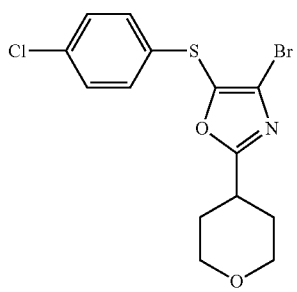 [SMILES: Clc1ccc(Sc2oc(C3CCOCC3)nc2Br)cc1]

To a solution of 5-[(4-chlorophenyl)sulfanyl]-2-(tetrahydro-2H-pyran-4-yl)-1,3-oxazole (521 g, 17.61 mmol) in DCM (176 ml) was added NBS (3.45 g, 19.38 mmol) and the reaction mixture was stirred at RT for 16 h. The reaction mixture was concentrated in vacuo and purified by flash chromatography (silica 330 g, 5 to 30% EtOAc in hexane), to give 4-bromo-5-[(4-chlorophenyl)sulfanyl]-2-(tetrahydro-2 H-pyran-4-yl)-1,3-oxazole (6.16 g). MS: M+H=376. H'NMR (400 MHz, CDCl$_3$) δ: 7.28 (d, J=8.4 Hz, 2 H), 7.22 (d, J=8.4 Hz, 2 H), 4.01 (dt, J=11.7 Hz, 3.6 Hz, 2 H), 3.50 (td, J=2.7, 11.7 Hz, 2 H), 3.09-2.98 (m, 1 H), 2.02-1.86 (m, 4 H).

Example B5.1

2-(5-{5-[(4-Chlorophenyl)sulfanyl]-2-(tetrahydro-2H-pyran-4-yl)-1,3-oxazol-4-yl}pyridin-2-yl)propan-2-ol

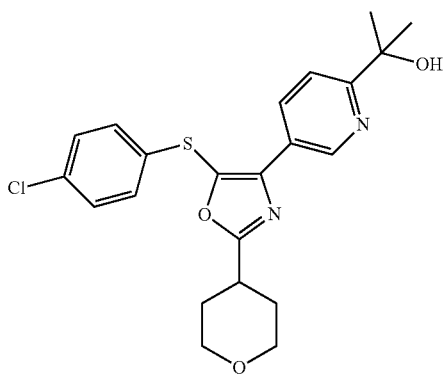 [SMILES: CC(C)(O)c1ccc(-c2nc(C3CCOCC3)oc2Sc2ccc(Cl)cc2)cn1]

To a mixture of B5 (540 mg, 1.44 mmol), tetrakis(triphenylphosphine)palladium(0) (83.0 mg, 0.0720 mmol), and 5-(4,4,5,5-tetramethyl-1,3,2-dioxaborolan-2-yl)-2-{2-[(trimethylsilyl)oxy]propan-2-yl}pyridine (438 mg, 1.73 mmol) in toluene (11.5 mL) was added 2.0 M aqueous solution of K$_2$CO$_3$ (2.2 mL). The resulting mixture was heated at 160° C. in a microwave for 1 h. The process was repeated three more times until the starting material consumed. The reaction mixture was diluted with dichloromethane, dried over Na$_2$SO$_4$ and filtered. The filtrate was concentrated and dissolved in THF (10.7 mL) and treated with TBAF (1.1 mL, 1M in THF) at room temperature for 1 h. The solvent was removed and the residue was purified by silica gel flash chromatography (5-70% EtOAc in hexanes), followed by reverse-phase HPLC (C-18, 20-90% MeCN in H$_2$O, with 0.05% TFA) and a final purification by silica gel flash chromatography (10-70% EtOAc in hexanes) to provide the title compound as a clear oil. The product turned into a white solid after converting to the HCl salt foam. $^1$H NMR (CDCl$_3$, 400 MHz) δ 9.18 (dd, J=1.2, 2.0, Hz, 1H), 8.33 (dd, J=2.0, 8.4 Hz, 1H), 7.42 (dd, J=1.2, 8.4 Hz, 1H), 7.29-7.238 (m, 2H), 7.16-7.13 (m, 2H), 4.85 (s, 1H), 4.06 (td, J=3.6, 8.4 Hz, 2H), 3.55 (dt, J=3.2, 10.8 Hz, 2H), 3.12 (m, 1H), 2.07-1.94 (m, 4H), 1.56 (s, 6H). HRMS (ES) [M+1]$^+$ calcd for C$_{22}$H$_{24}$ClN$_2$O$_3$S: 431.1191. Found: 431.1198.

Intermediates B4.2

(trans-4-{4-Bromo-5-[(4-chlorophenyl)sulfanyl]-1,3-oxazol-2-yl}cyclohexyl)methanol (cis-4-{4-Bromo-5-[(4-chlorophenyl)sulfanyl]-1,3-oxazol-2-yl}cyclohexyl)methanol

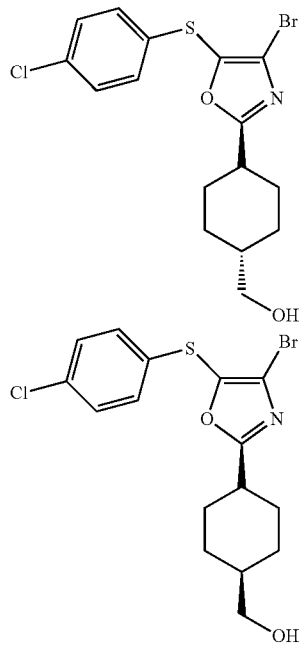

Step B42-1: methyl 4-({2-[(4-chlorophenyl)sulfanyl]ethyl}carbamoyl)cyclohexanecarboxylate

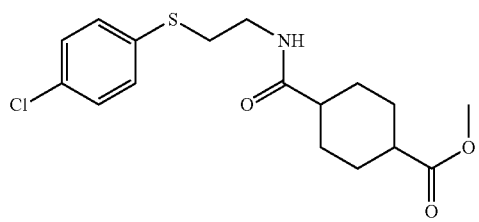 [SMILES: COC(=O)C1CCC(C(=O)NCCSc2ccc(Cl)cc2)CC1]

To a solution of 2-[(4-chlorophenyl)sulfanyl]ethanamine (12.2 g, 542 mmol) in DMF (350 ml) was added sequentially 4-(methoxycarbonyl)cyclohexanecarboxylic acid (cis/trans mixture), EDC (11.4 g, 59.7 mmol) and HOAt (1.48 g, 10.9 mmol) at room temperature followed by Et₃N (17.39 ml, 125 mmol). The reaction was stirred overnight at ambient temperature, diluted with water and extracted with EtOAc. The combined organic layers were dried (Na₂SO₄), filtered and conc. The residue was purified by silica gel flash chromatography (0-70% EtOAc in heptane) to afford the product. LCMS: M+H=356.1.

Step B4.2-2: methyl 4-{5-[(4-chlorophenyl)sulfanyl]-1,3-oxazol-2-yl}cyclohexanecarboxylate

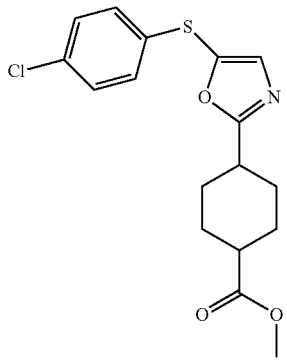 [SMILES: COC(=O)C1CCC(c2ncc(Sc3ccc(Cl)cc3)o2)CC1]

To a solution of the intermediate from step B4.2-1 (10 g, 28.1 mmol) in chlorobenzene (150 ml) was added NCS (7.5 g, 56.2 mmol) in one portion. The mixture was stirred at RT for 2 hrs, followed by the addition of TFA (0.35 ml, 2.81 mmol) and stirred at RT overnight. The reaction mixture was washed with water (50 mL×2), sat.d. NaHCO₃ (50 mL). The organic layer was dried over Na₂SO₄, filtered. TFA (0.216 ml, 2.81 mmol) was then added to the filtrate and the solvent was removed by conc. The residue was purified by silica gel chromatography (0-60% EtOAc in heptane) to provide the product. LCMS: M+H=352.1.

Step B4.2-3: Methyl 4-{4-bromo-5-[(4-chlorophenyl)sulfanyl]-1,3-oxazol-2-yl}cyclohexanecarboxylate

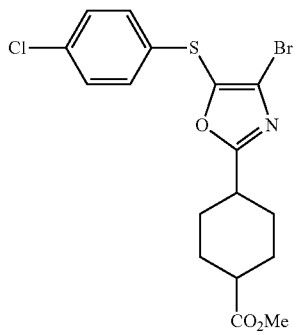 [SMILES: COC(=O)C1CCC(c2nc(Br)c(Sc3ccc(Cl)cc3)o2)CC1]

To a solution of methyl 4-{5-[(4-chlorophenyl)sulfanyl]-1,3-oxazol-2-yl}cyclohexanecarboxylate (3.762 g, 10.69 mmol) in DCM (107 ml) was added NBS (2.093 g, 11.76 mmol) and the reaction mixture was stirred at RT for 16 h. The reaction mixture was concentrated in vacuo and purified by flash chromatography (silica 330 g, 0 to 25% EtOAc in hexane), to give methyl 4-{4-bromo-5-[(4-chlorophenyl)sulfanyl]-1,3-oxazol-2-yl}cyclohexanecarboxylate (3.5 g), as a ca. 2:1 mixture of trans/cis isomers. LCMS: M+H 430.

Step B4.2-4: (trans-4-{4-Bromo-5-[(4-chlorophenyl)sulfanyl]-1,3-oxazol-2-yl}cyclohexyl)methanol (cis-4-{4-Bromo-5-[(4-chlorophenyl)sulfanyl]-1,3-oxazol-2-yl}cyclohexyl)methanol

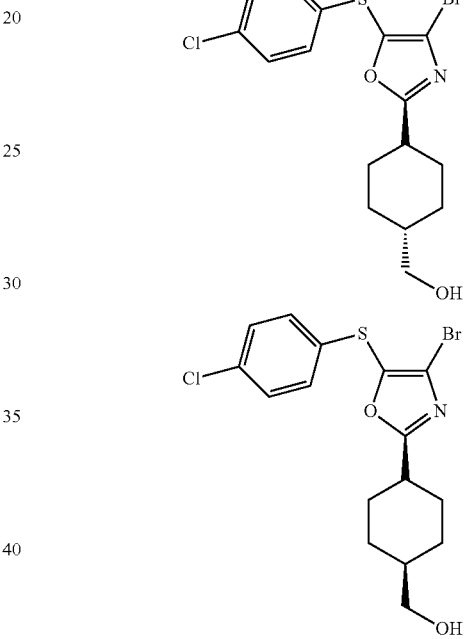

Sodium borohydride (105 mg, 2.79 mmol) was added to a stirred mixture of methyl ester (200 mg, 0.464 mmol) and calcium chloride (206 mg, 1.86 mmol) in ethanol (4.64 ml) and the mixture was stirred at room temperature for overnight. Still small amount of SM. Additional amount CaCl₂ and NaBH₄ and stirred at room temperature for 1 h. Water and brine were added and the mixture was extracted with CH₂Cl₂ (3×). The combined organic layers were washed with brine, dried over Na₂SO₄, filtered and conc. LC-MS: [M+H]⁺= 404.1. The residue was purified by silica (0-60% EtOAc in hex) to isolate two isomers. Fast peak: ¹H NMR (CDCl₃, 400 MHz) δ 7.29-7.26 (m, 2H), 7.22-7.18 (m, 2H), 3.50 (d, J=6.4 Hz, 2H), 3.07 (quintet, J=4.8 Hz, 1H), 2.17-2.10 (m, 2H), 1.77-1.72 (m, 2H), 1.71-1.63 (m, 3H), 1.38-1.30 (m, 2H). Slow peak: ¹H NMR (CDCl₃, 400 MHz) δ 7.30-7.27 (m, 2H), 7.22-7.17 (m, 2H), 3.60-3.40 (ABq, J=6.0 Hz, 2H), 2.77-2.69 (m, 1H), 2.17-2.14 (m, 2H), 1.96-1.92 (m, 2H), 1.63-1.49 (m, 3H), 1.13-1.03 (m, 2H).

Example B5.18

2-(5-{5-[(4-Chlorophenyl)sulfanyl]-2-[cis-4-(hydroxymethyl)cyclohexyl]-1,3-oxazol-4-yl}pyridin-2-yl)propan-2-ol

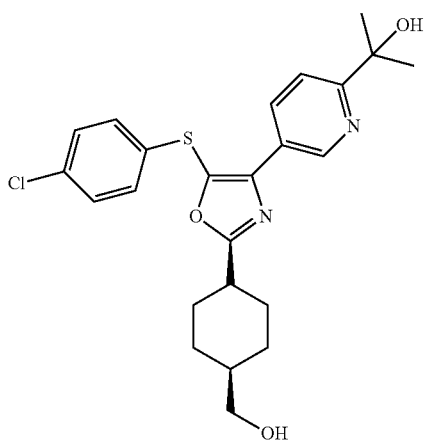

To a mixture of bromide (43.0 mg, 0.107 mmol), 5-(4,4,5,5-tetramethyl-1,3,2-dioxaborolan-2-yl)-2-{2-[(trimethylsilyl)oxy]propan-2-yl}pyridine (40.5 mg, 0.160 mmol), tetrakis(triphenylphosphine)palladium(0) (12.3 mg, 10.7 µmol) in toluene (2000 µl) was added K$_2$CO$_3$ (267 µl, 0.534 mmol) and heated in oil bath at 120° C. for 12 h. The reaction was diluted with CH$_2$Cl$_2$, dried over Na$_2$SO$_4$, filtered and conc. The residue was dissolved in THF (1 mL) and treated with TBAF (107 µl, 0.107 mmol) for 1 h. The solvent was removed and the residue was purified by reverse-phase HPLC (C-18, 20-80% MeCN in H$_2$O, with 0.05% TFA) to provide product as a white solid. $^1$H NMR (CDCl$_3$, 400 MHz) δ 9.37 (s, 1H), 8.86-8.82 (m, 1H), 7.72 (d, J=8.8 Hz, 1H), 7.31-7.27 (m, 2H), 7.22-7.19 (m, 2H), 4.24 (d, 6.0 Hz, 1H), 3.54 (d, J=6.0 Hz, 1H), 2.87-2.78 (m, 1H), 2.27-2.20 (m, 2H), 2.00-1.96 (m, 2H), 1.71 (s, 6H), 1.70-1.43 (m, 3H), 1.26-1.09 (m, 2H). FIRMS (ES) [M+1]$^+$ calcd for C$_{24}$H$_{28}$ClN$_2$O$_3$S: 459.1504. Found: 459.1498.

| Ex # | Structure | IUPAC names | M + 1 |
| --- | --- | --- | --- |
| B5.1 | 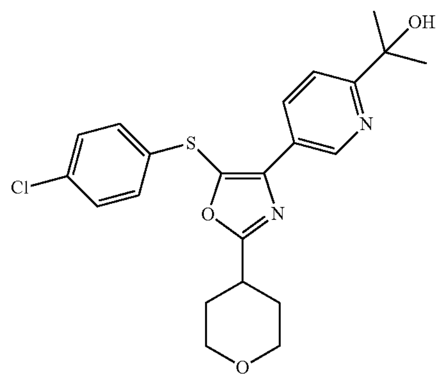 | 2-(5-{5-[(4-chlorophenyl)sulfanyl]-2-(tetrahydro-2H-pyran-4-yl)-1,3-oxazol-4-yl}pyridin-2-yl)propan-2-ol | 431.3 |
| B5.2 | 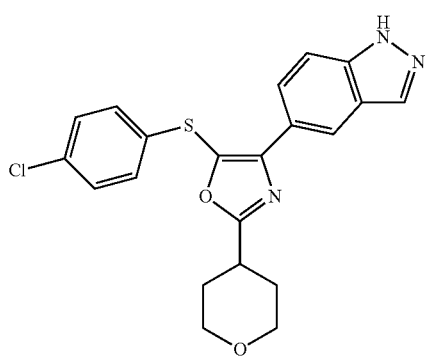 [SMILES: Clc1ccc(Sc2oc(C3CCOCC3)nc2-c2ccc3[nH]ncc3c2)cc1] | 5-{5-[(4-chlorophenyl)sulfanyl]-2-(tetrahydro-2H-pyran-4-yl)-1,3-oxazol-4-yl}-1H-indazole | 412.3 |

| Ex # | Structure | IUPAC names | M + 1 |
|---|---|---|---|
| B5.3 | 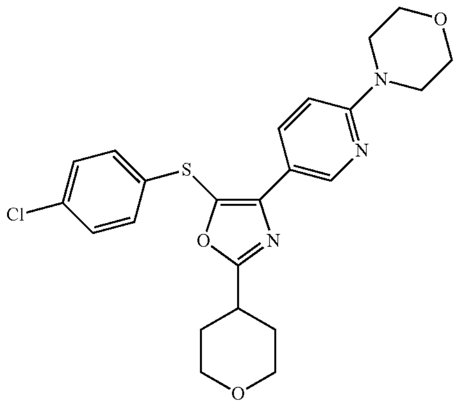 [SMILES: Clc1ccc(Sc2oc(C3CCOCC3)nc2-c2ccc(N3CCOCC3)nc2)cc1] | 4-(5-{5-[(4-chlorophenyl)sulfanyl]-2-(tetrahydro-2H-pyran-4-yl)-1,3-oxazol-4-yl}pyridin-2-yl)morpholine | 458.3 |
| B5.4 | 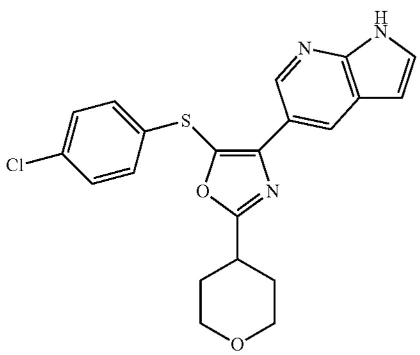 [SMILES: Clc1ccc(Sc2oc(C3CCOCC3)nc2-c2cnc3[nH]ccc3c2)cc1] | 5-{5-[(4-chlorophenyl)sulfanyl]-2-(tetrahydro-2H-pyran-4-yl)-1,3-oxazol-4-yl}-1H-pyrrolo[2,3-b]pyridine | 412.3 |
| B5.5 | 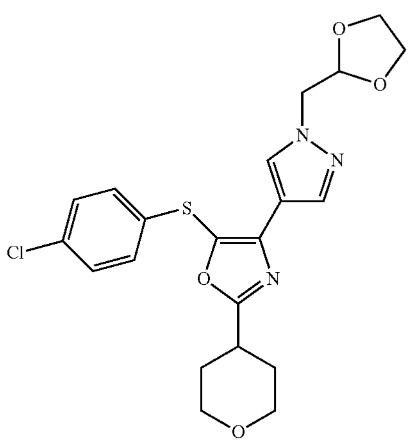 [SMILES: Clc1ccc(Sc2oc(C3CCOCC3)nc2-c2cnn(CC3OCCO3)c2)cc1] | 5-[(4-chlorophenyl)sulfanyl]-4-[1-(1,3-dioxolan-2-ylmethyl)-1H-pyrazol-4-yl]-2-(tetrahydro-2H-pyran-4-yl)-1,3-oxazole | 448.3 |
| B5.6 | 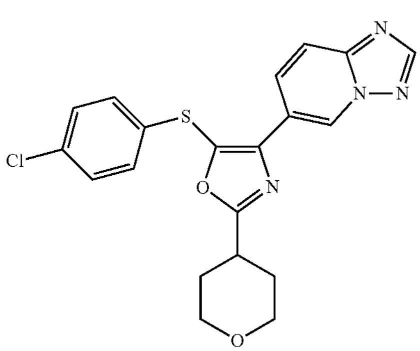 [SMILES: Clc1ccc(Sc2oc(C3CCOCC3)nc2-c2ccc3ncnn3c2)cc1] | 6-{5-[(4-chlorophenyl)sulfanyl]-2-(tetrahydro-2H-pyran-4-yl)-1,3-oxazol-4-yl}[1,2,4]triazolo[1,5-a]pyridine | 413.3 |

| Ex # | Structure | IUPAC names | M + 1 |
|---|---|---|---|
| B5.7 | 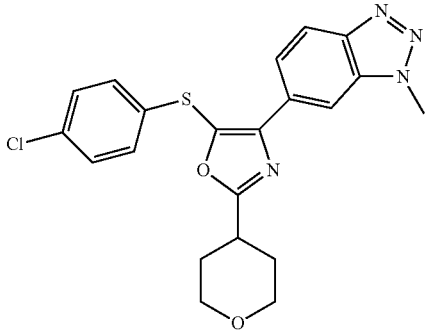 [SMILES: Cn1nnc2ccc(-c3nc(C4CCOCC4)oc3Sc3ccc(Cl)cc3)cc21] | 6-{5-[(4-chlorophenyl)sulfanyl]-2-(tetrahydro-2H-pyran-4-yl)-1,3-oxazol-4-yl}-1-methyl-1H-benzotriazole | 427.3 |
| B5.8 | 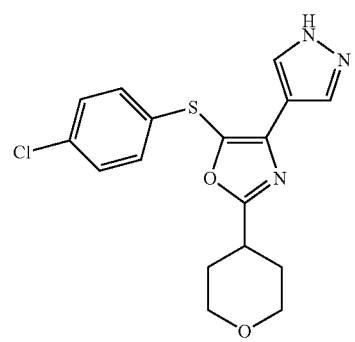 [SMILES: Clc1ccc(Sc2oc(C3CCOCC3)nc2-c2cn[nH]c2)cc1] | 5-[(4-chlorophenyl)sulfanyl]-4-(1H-pyrazol-4-yl)-2-(tetrahydro-2H-pyran-4-yl)-1,3-oxazole | 362.3 |
| B5.9 | 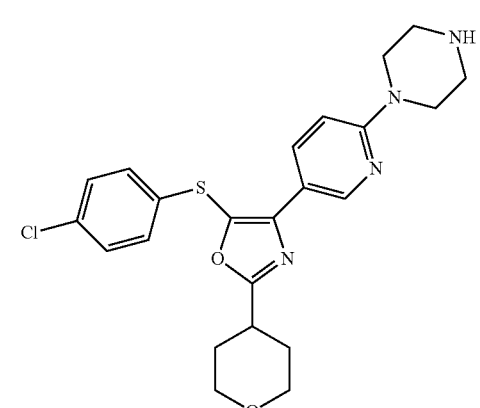 | 1-(5-{5-[(4-chlorophenyl)sulfanyl]-2-(tetrahydro-2H-pyran-4-yl)-1,3-oxazol-4-yl}pyridin-2-yl)piperazine | 457.3 |
| B5.10 | 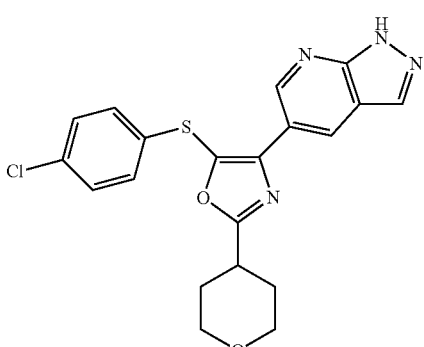 | 5-{5-[(4-chlorophenyl)sulfanyl]-2-(tetrahydro-2H-pyran-4-yl)-1,3-oxazol-4-yl}-1H-pyrazolo[3,4-b]pyridine | 413.3 |

-continued

| Ex # | Structure | IUPAC names | M + 1 |
|---|---|---|---|
| B5.11 | 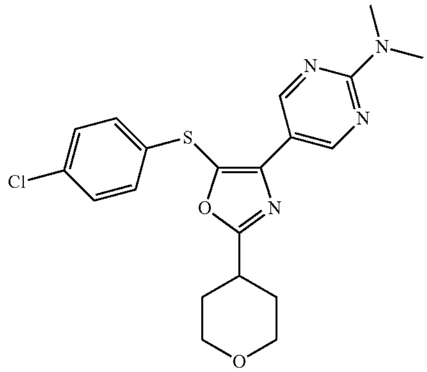 [SMILES: CN(C)c1ncc(-c2nc(C3CCOCC3)oc2Sc2ccc(Cl)cc2)cn1] | 5-{5-[(4-chlorophenyl)sulfanyl]-2-(tetrahydro-2H-pyran-4-yl)-1,3-oxazol-4-yl}-N,N-dimethylpyrimidin-2-amine | 417.4 |
| B5.12 | 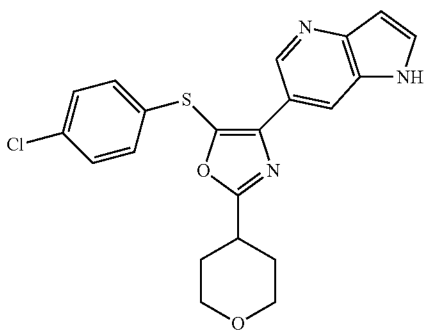 [SMILES: Clc1ccc(Sc2oc(C3CCOCC3)nc2-c2cnc3cc[nH]c3c2)cc1] | 6-{5-[(4-chlorophenyl)sulfanyl]-2-(tetrahydro-2H-pyran-4-yl)-1,3-oxazol-4-yl}-1H-pyrrolo[3,2-b]pyridine | 412.3 |
| B5.13 | 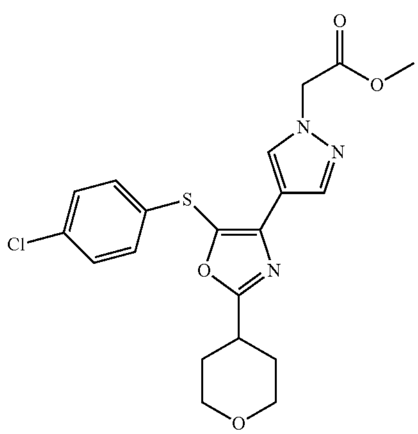 [SMILES: COC(=O)Cn1cc(-c2nc(C3CCOCC3)oc2Sc2ccc(Cl)cc2)cn1] | methyl (4-{5-[(4-chlorophenyl)sulfanyl]-2-(tetrahydro-2H-pyran-4-yl)-1,3-oxazol-4-yl}-1H-pyrazol-1-yl)acetate | 434.3 |
| B5.14 | 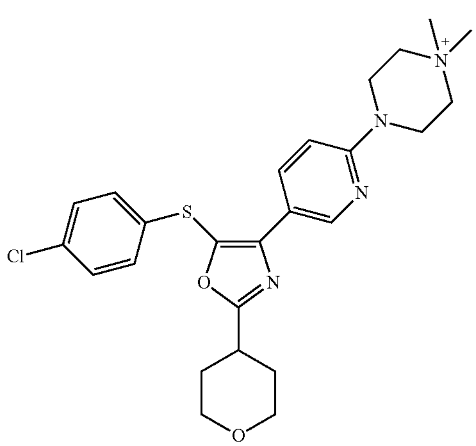 | 4-(5-{5-[(4-chlorophenyl)sulfanyl]-2-(tetrahydro-2H-pyran-4-yl}-1,3-oxazol-4-yl}pyridin-2-yl)-1,1-dimethylpiperazin-1-ium | 458.4 |

-continued

| Ex # | Structure | IUPAC names | M + 1 |
|---|---|---|---|
| B5.15 | 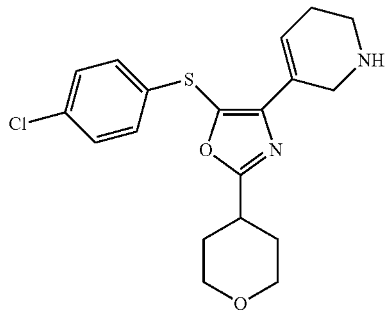 [SMILES: Clc1ccc(Sc2oc(C3CCOCC3)nc2C2=CCCNC2)cc1] | 5-{5-[(4-chlorophenyl)sulfanyl]-2-(tetrahydro-2H-pyran-4-yl)-1,3-oxazol-4-yl}-1,2,3,6-tetrahydropyridine | 377.3 |
| B5.16 | 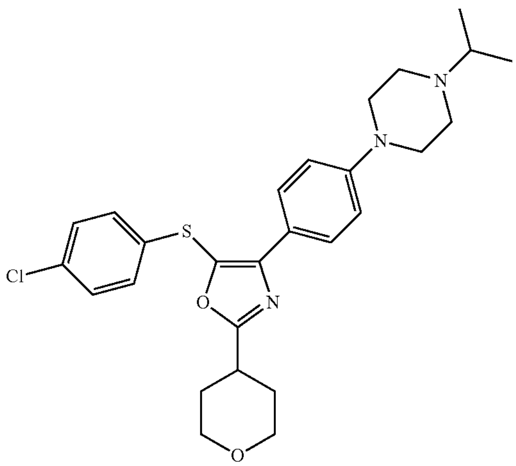 [SMILES: CC(C)N1CCN(c2ccc(-c3nc(C4CCOCC4)oc3Sc3ccc(Cl)cc3)cc2)CC1] | 1-(4-{5-[(4-chlorophenyl)sulfanyl]-2-(tetrahydro-2H-pyran-4-yl)-1,3-oxazol-4-yl}phenyl)-4-(propan-2-yl)piperazine | 498.2 |
| B5.17 | 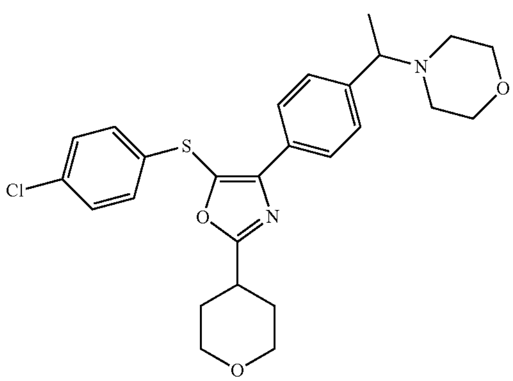 [SMILES: CC(c1ccc(-c2nc(C3CCOCC3)oc2Sc2ccc(Cl)cc2)cc1)N1CCOCC1] | 4-[1-(4-{5-[(4-chlorophenyl)sulfanyl]-2-(tetrahydro-2H-pyran-4-yl)-1,3-oxazol-4-yl}phenyl)ethyl]morpholine | 485.2 |
| B5.18 | 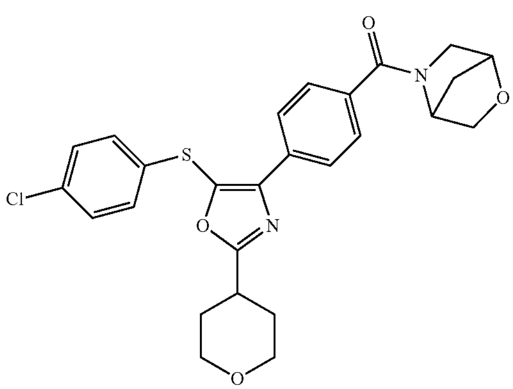 [SMILES: O=C(c1ccc(-c2nc(C3CCOCC3)oc2Sc2ccc(Cl)cc2)cc1)N1CC2CC1CO2] | (4-{5-[(4-chlorophenyl)sulfanyl]-2-(tetrahydro-2H-pyran-4-yl)-1,3-oxazol-4-yl}phenyl)(2-oxa-5-azabicyclo[2.2.1]hept-5-yl)methanone | 497.1 |

| Ex # | Structure | IUPAC names | M + 1 |
|---|---|---|---|
| B5.19 | 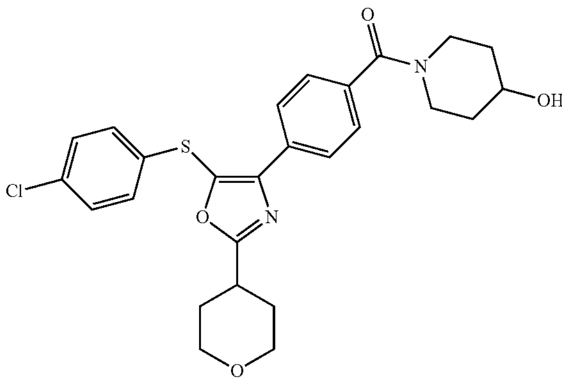 [SMILES: O=C(c1ccc(-c2nc(C3CCOCC3)oc2Sc2ccc(Cl)cc2)cc1)N1CCC(O)CC1] | (4-{5-[(4-chlorophenyl)sulfanyl]-2-(tetrahydro-2H-pyran-4-yl)-1,3-oxazol-4-yl}phenyl)(4-hydroxypiperidin-1-yl)methanone | 499.1 |
| B5.20 | 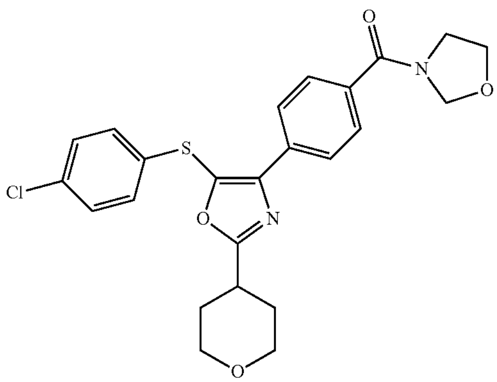 [SMILES: O=C(c1ccc(-c2nc(C3CCOCC3)oc2Sc2ccc(Cl)cc2)cc1)N1CCOC1] | (4-{5-[(4-chlorophenyl)sulfanyl]-2-(tetrahydro-2H-pyran-4-yl)-1,3-oxazol-4-yl}phenyl)(1,3-oxazolidin-3-yl)methanone | 485.1 |
| B5.21 | 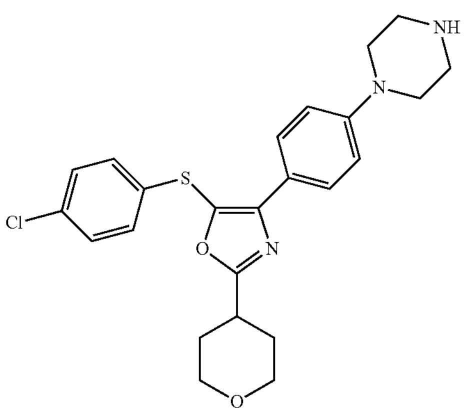 [SMILES: Clc1ccc(Sc2oc(C3CCOCC3)nc2-c2ccc(N3CCNCC3)cc2)cc1] | 1-(4-{5-[(4-chlorophenyl)sulfanyl]-2-(tetrahydro-2H-pyran-4-yl)-1,3-oxazol-4-yl}phenyl)piperazine | 456.2 |
| B5.22 | 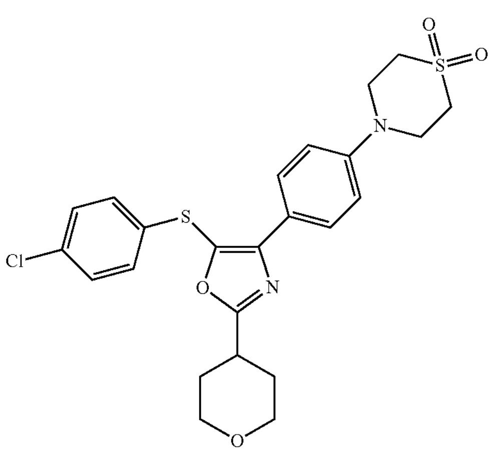 [SMILES: O=S1(=O)CCN(c2ccc(-c3nc(C4CCOCC4)oc3Sc3ccc(Cl)cc3)cc2)CC1] | 4-(4-{5-[(4-chlorophenyl)sulfanyl]-2-(tetrahydro-2H-pyran-4-yl)-1,3-oxazol-4-yl}phenyl)thiomorpholine 1,1-dioxide | 505.1 |

| Ex # | Structure | IUPAC names | M + 1 |
| --- | --- | --- | --- |
| B5.23 | 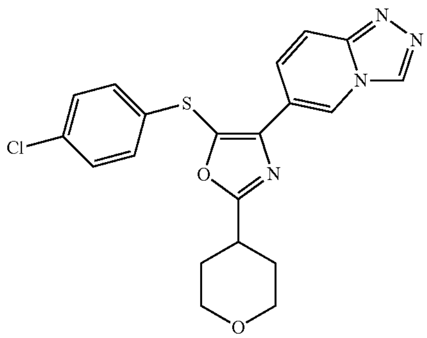 [SMILES: Clc1ccc(Sc2oc(C3CCOCC3)nc2-c2ccc3nncn3c2)cc1] | 6-{5-[(4-chlorophenyl)sulfanyl]-2-(tetrahydro-2H-pyran-4-yl)-1,3-oxazol-4-yl}[1,2,4]triazolo[4,3-a]pyridine | 413.1 |
| B5.24 | 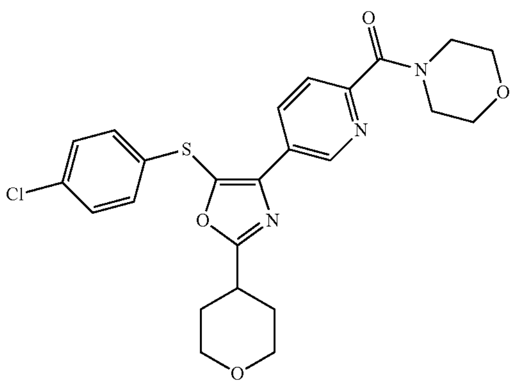 [SMILES: O=C(c1ccc(-c2nc(C3CCOCC3)oc2Sc2ccc(Cl)cc2)cn1)N1CCOCC1] | (5-{5-[(4-chlorophenyl)sulfanyl]-2-(tetrahydro-2H-pyran-4-yl)-1,3-oxazol-4-yl}pyridin-2-yl)(morpholin-4-yl)methanone | 486.1 |
| B5.25 | 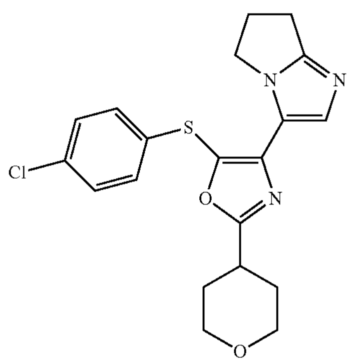 [SMILES: Clc1ccc(Sc2oc(C3CCOCC3)nc2-c2cnc3n2CCC3)cc1] | 3-{5-[(4-chlorophenyl)sulfanyl]-2-(tetrahydro-2H-pyran-4-yl)-1,3-oxazol-4-yl}-6,7-dihydro-5H-pyrrolo[1,2-a]imidazole | 402.1 |
| B5.26 | 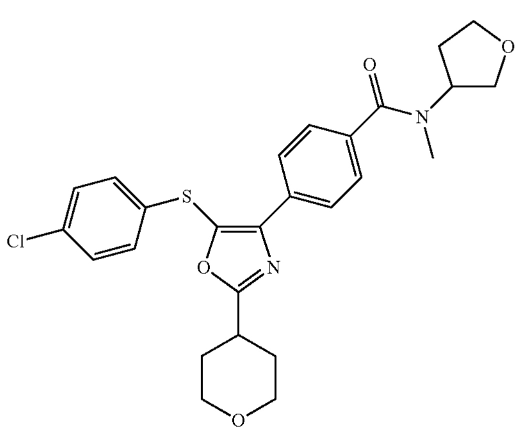 [SMILES: CN(C(=O)c1ccc(-c2nc(C3CCOCC3)oc2Sc2ccc(Cl)cc2)cc1)C1CCOC1] | 4-{5-[(4-chlorophenyl)sulfanyl]-2-(tetrahydro-2H-pyran-4-yl)-1,3-oxazol-4-yl}-N-methyl-N-(tetrahydrofuran-3-yl)benzamide | 499.1 |

| Ex # | Structure | IUPAC names | M + 1 |
|---|---|---|---|
| B5.27 | 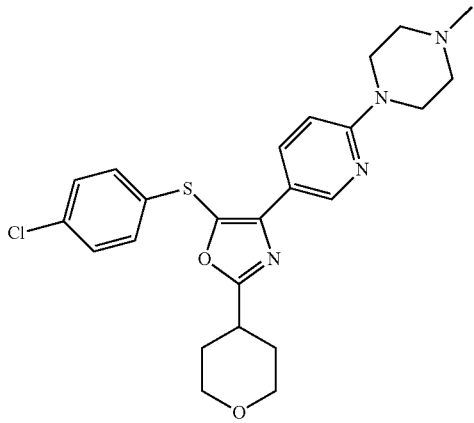 [SMILES: CN1CCN(c2ccc(-c3nc(C4CCOCC4)oc3Sc3ccc(Cl)cc3)cn2)CC1] | 1-(5-{5-[(4-chlorophenyl)sulfanyl]-2-(tetrahydro-2H-pyran-4-yl)-1,3-oxazol-4-yl}pyridin-2-yl)-4-methylpiperazine | 471.2 |
| B5.28 | 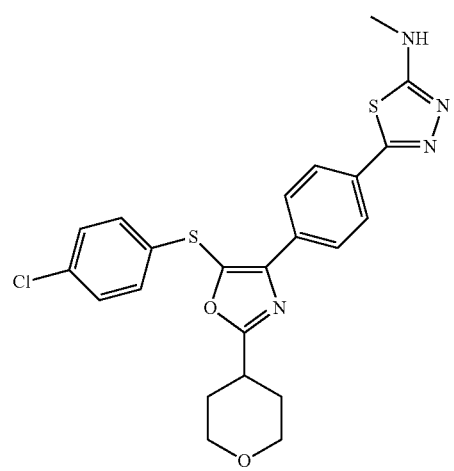 [SMILES: CNc1nnc(-c2ccc(-c3nc(C4CCOCC4)oc3Sc3ccc(Cl)cc3)cc2)s1] | 5-(4-{5-{(4-chlorophenyl)sulfanyl]-2-(tetrahydro-2H-pyran-4-yl)-1,3-oxazol-4-yl}phenyl)-N-methyl-1,3,4-thiadiazol-2-amine | 485.1 |
| B5.29 | 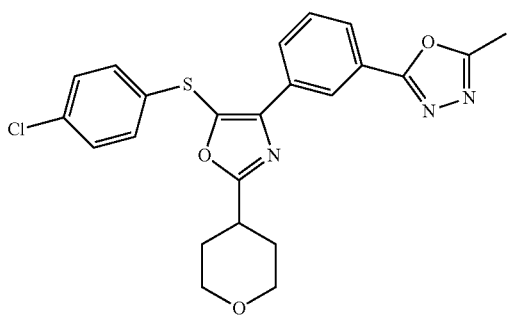 [SMILES: Cc1nnc(-c2cccc(-c3nc(C4CCOCC4)oc3Sc3ccc(Cl)cc3)c2)o1] | 2-(3-{5-[(4-chlorophenyl)sulfanyl]-2-(tetrahydro-2H-pyran-4-yl)-1,3-oxazol-4-yl}phenyl)-5-methyl-1,3,4-oxadiazole | 454.1 |
| B5.30 | 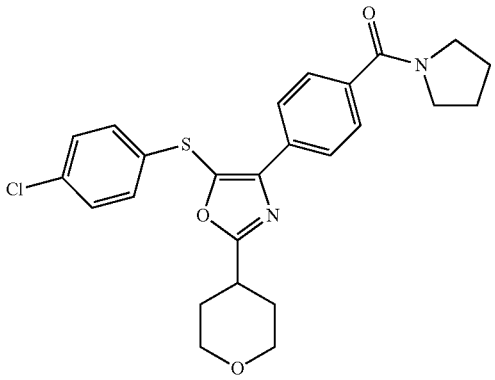 [SMILES: O=C(c1ccc(-c2nc(C3CCOCC3)oc2Sc2ccc(Cl)cc2)cc1)N1CCCC1] | (4-{5-[(4-chlorophenyl)sulfanyl]-2-(tetrahydro-2H-pyran-4-yl)-1,3-oxazol-4-yl}phenyl)(pyrrolidin-1-yl)methanone | 469.1 |

| Ex # | Structure | IUPAC names | M + 1 |
|---|---|---|---|
| B5.31 | 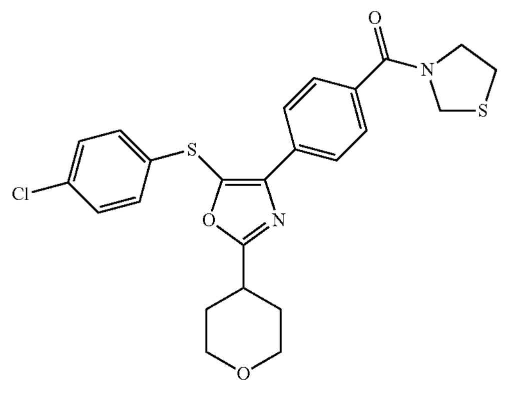 [SMILES: O=C(c1ccc(-c2nc(C3CCOCC3)oc2Sc2ccc(Cl)cc2)cc1)N1CCSC1] | (4-{5-{(4-chlorophenyl)sulfanyl]-2-(tetrahydro-2H-pyran-4-yl)-1,3-oxazol-4-yl}phenyl)(1,3-thiazolidin-3-yl)methanone | 487.1 |
| B5.32 | 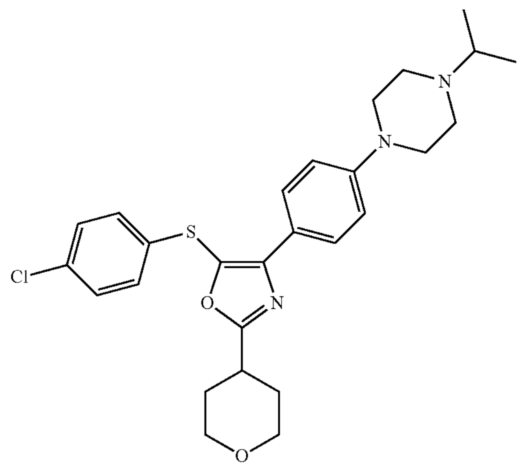 [SMILES: CC(C)N1CCN(c2ccc(-c3nc(C4CCOCC4)oc3Sc3ccc(Cl)cc3)cc2)CC1] | 1-(4-{5-[(4-chlorophenyl)sulfanyl]-2-(tetrahydro-2H-pyran-4-yl)-1,3-oxazol-4-yl}phenyl)-4-(propan-2-yl)piperazine | 498.2 |
| B5.33 | 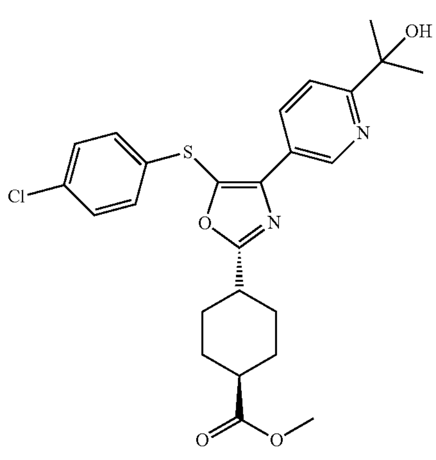 | methyl trans-4-{5-[(4-chlorophenyl)sulfanyl]-4-[6-(2-hydroxypropan-2-yl)pyridin-3-yl]-1,3-oxazol-2-yl}cyclohexanecarboxylate | 488.3 |

| Ex # | Structure | IUPAC names | M + 1 |
|---|---|---|---|
| B5.34 | 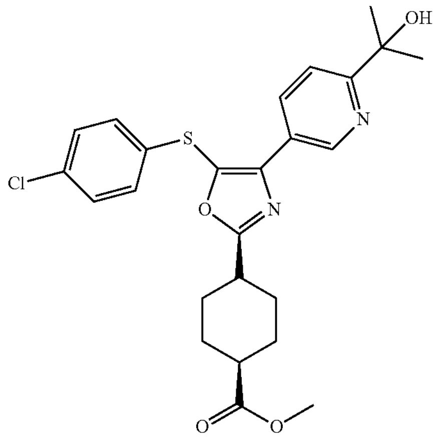 | methyl cis-4-{5-[(4-chlorophenyl)sulfanyl]-4-[6-(2-hydroxypropan-2-yl)pyridin-3-yl]-1,3-oxazol-2-yl}cyclohexanecarboxylate | 488.3 |
| B5.35 | 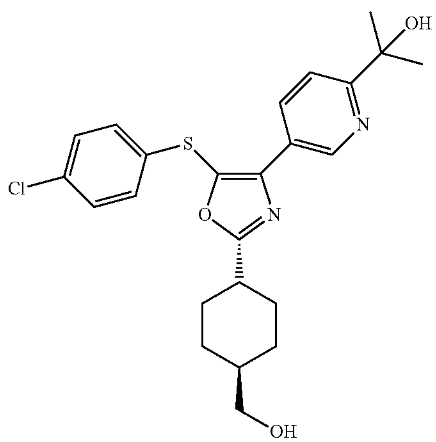 | 2-(5-{5-[(4-chlorophenyl)sulfanyl]-2-[trans-4-(hydroxymethyl)cyclohexyl]-1,3-oxazol-4-yl}pyridin-2-yl)propan-2-ol | 459.3 |
| B5.36 | 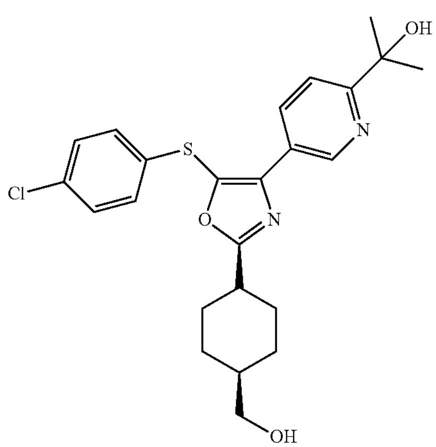 | 2-(5-{5-[(4-chlorophenyl)sulfanyl]-2-[cis-4-(hydroxymethyl)cyclohexyl]-1,3-oxazol-4-yl}pyridin-2-yl)propan-2-ol | 459.3 |

| Ex # | Structure | IUPAC names | M + 1 |
| --- | --- | --- | --- |
| B5.37 | 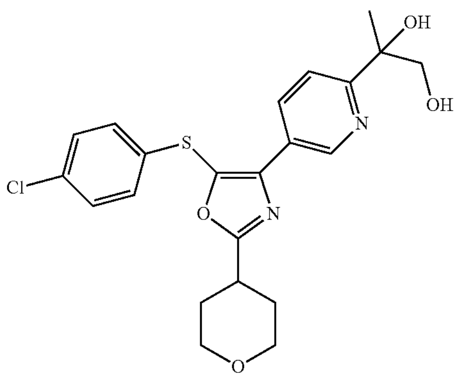 [SMILES: CC(O)(CO)c1ccc(-c2nc(C3CCOCC3)oc2Sc2ccc(Cl)cc2)cn1] | 2-(5-{5-[(4-chlorophenyl)sulfanyl]-2-(tetrahydro-2H-pyran-4-yl)-1,3-oxazol-4-yl}pyridin-2-yl)propane-1,2-diol | 447.3 |
| B5.38 | 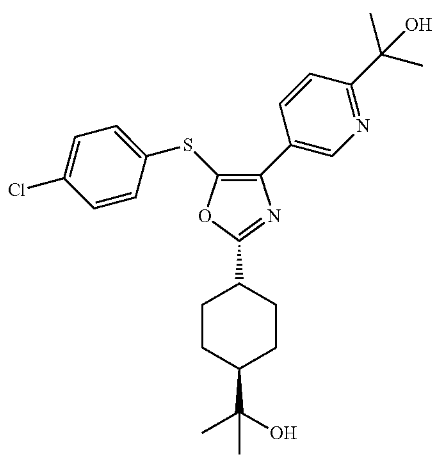 | 2-(5-{5-[(4-chlorophenyl)sulfanyl]-2-[trans-4-(2-hydroxypropan-2-yl)cyclohexyl]-1,3-oxazol-4-yl}pyridin-2-yl)propan-2-ol | 487.3 |
| B5.39 | 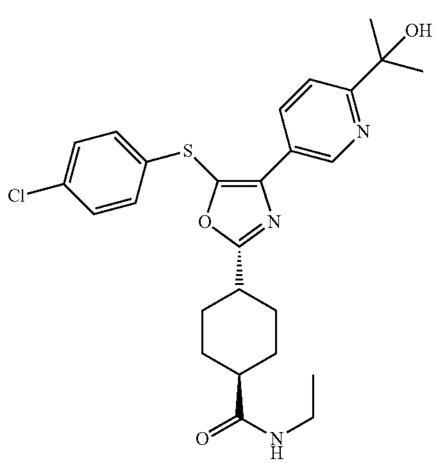 | trans-4-{5-[(4-chlorophenyl)sulfanyl]-4-[6-(2-hydroxypropan-2-yl)pyridin-3-yl]-1,3-oxazol-2-yl}-N-ethylcyclohexanecarboxamide | 500.3 |

Intermediate C5.1

2-Chloro-5-[(4-chlorophenyl)sulfanyl]-4-[4-(methylsulfinyl)phenyl]-1,3-oxazole

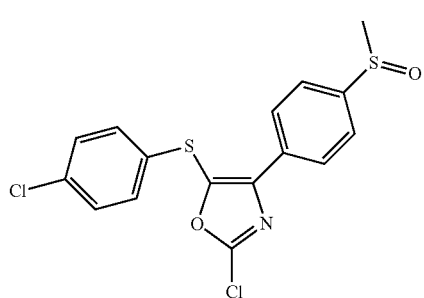 [SMILES: CS(=O)c1ccc(-c2nc(Cl)oc2Sc2ccc(Cl)cc2)cc1]

Step C5.1-1: 2-[(4-Chlorophenyl)sulfanyl]-1-[4-(methylsulfanyl)phenyl]ethanone

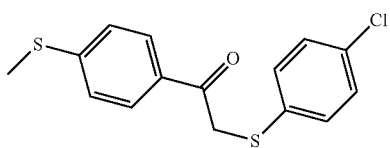 [SMILES: CSc1ccc(C(=O)CSc2ccc(Cl)cc2)cc1]

To a stirring mixture of sodium ethoxide (13.32 g, 196 mmol) in ethanol (1L) in a 2 L RBF was added 4-chlorothiophenol (26.0 g, 179 mmol), followed by 2-bromo-1-[4-(methylsulfanyl)phenyl]ethanone (40 g, 163 mmol). The reaction mixture was heated to reflux until all solid dissolved, hot filtered through a fritted funnel, then allowed to cool slowly to room temperature, then to 0° C. in an ice bath. The title compound was isolated as pink needle-like crystals (43.9 g, 87%) by filtration. LCMS M+1=309.2.

Step C5.1-2: 2-Bromo-2-[(4-chlorophenyl)sulfanyl]-1-[4-(methylsulfanyl)phenyl]ethanone

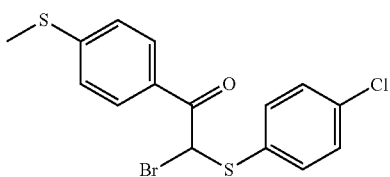 [SMILES: CSc1ccc(C(=O)C(Br)Sc2ccc(Cl)cc2)cc1]

Bromine (7.68 mL, 149 mmol) was added dropwise to a stirring solution of the above product from step C5.1-1 in chloroform (450 mL). After 30 minutes, an additional aliquot of bromine (0.731 mL, 14.2 mmol) was added. The reaction mixture was washed with aqueous saturated sodium bicarbonate (200 mL), followed by aqueous sodium thiosulfate (1M, 200 mL). The organic phase was dried over sodium sulfate, and concentrated to dryness. The product was isolated as yellow solid (50.7 g, 92%) by recrystallization from dichloromethane and hexanes. LCMS M+1=389.2.

Step C5.1-3: 5-[(4-Chlorophenyl)sulfanyl]-4-[4-(methylsulfanyl)phenyl]-1,3-oxazole

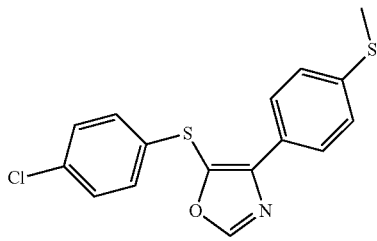 [SMILES: CSc1ccc(-c2ncoc2Sc2ccc(Cl)cc2)cc1]

The above product from step C5.1-2 (50.7 g, 131 mmol) was combined with formamide (155 mL, 3889 mmol) and heated to 95° C. while stirring vigorously for 20 minutes. The cooled reaction mixture was diluted with dichloromethane (150 mL), and washed three times with an aqueous solution of LiCl (3 M, 100 mL). The organic layer was dried over sodium sulfate, and the desired product (13.2 g, 30%) was isolated by silica gel chromatography (0-30% EtOAc in hexanes). LCMS M+1=334.2.

Step C5.1-4: 2-Chloro-5-[(4-chlorophenyl)sulfanyl]-4-[4-(methylsulfanyl)phenyl]-1,3-oxazole

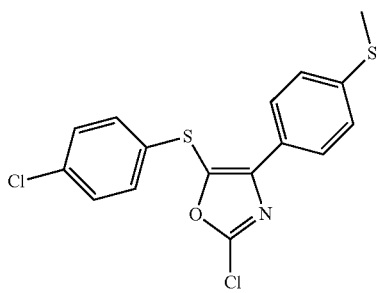 [SMILES: CSc1ccc(-c2nc(Cl)oc2Sc2ccc(Cl)cc2)cc1]

n-Butyl lithium (18.91 mL, 2.5 M, 47.3 mmol) was added dropwise to a stirring solution of the above product from step C5.1-3 (13.15 g, 39.4 mmol) in dry THF (200 mL) under nitrogen at −78° C. When the addition was complete, hexachloroethane (18.65 g, 79 mmol) was added in one portion, and the reaction was allowed to warm to room temperature overnight. The reaction was quenched with methanol, concentrated and purified by silica gel chromatography (0-20% EtOAc in hexanes). The product was isolated as a yellow solid (7.5 g, 52%). LCMS M+1=368.2.

Step C5.1-5: 2-Chloro-5-[(4-chlorophenyl)sulfanyl]-4-[4-(methylsulfinyl)phenyl]-1,3-oxazole

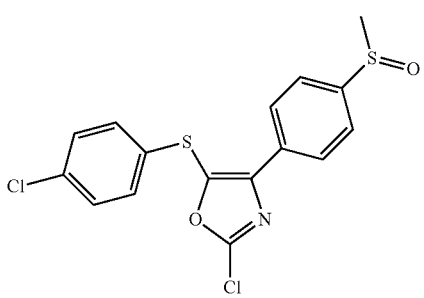 [SMILES: CS(=O)c1ccc(-c2nc(Cl)oc2Sc2ccc(Cl)cc2)cc1]

The above product from step C5.1-4 was dissolved in dichloromethane (55 mL), and stirred vigorously. m-Chloro peroxybenzoic acid (1.25 g, 5.43 mmol), was added dropwise as a solution in dichloromethane (10 mL). The reaction mixture was washed with a saturated aqueous solution of sodium bicarbonate (50 mL). The organic layer was dried over sodium sulfate before concentrating to give the desired product as a yellow oil (2.1 g, 100%). LCMS

Example C6.1

5-[(4-Chlorophenyl)sulfanyl]-2-(cyclohex-1-en-1-yl)-4-[4-(methylsulfinyl)phenyl]-1,3-oxazole

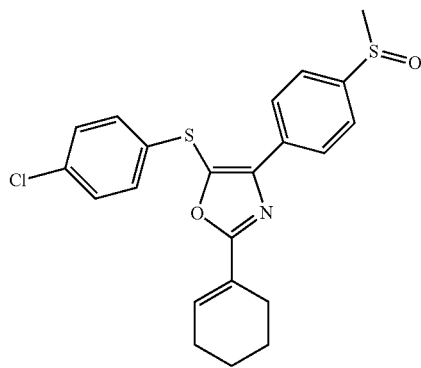 [SMILES: CS(=O)c1ccc(-c2nc(C3=CCCCC3)oc2Sc2ccc(Cl)cc2)cc1]

Intermediate C5.1 was combined with cyclohex-1-en-1-ylboronic acid (22.6 mg, 0.180 mmol), aqueous sodium carbonate (0.180 mL, 2 M, 0.359 mmol), and 1,4-dioxane (1.2 mL) in a microwave vessel. The reaction mixture was degassed with nitrogen for 10 minutes before adding trans-dichloro(bistriphenylphosphine) palladium (12.6 mg, 0.018 mmol). The reaction mixture was heated by microwave for 20 minutes at 150° C. An additional aliquot trans-dichloro(bistriphenylphosphine) palladium (12.6 mg, 0.018 mmol) was added, and the reaction mixture was heated again as before. The reaction mixture was diluted with dichloromethane (10 mL), and washed with brine (10 mL). The organic phase was stirred with Quadrapure resin (Sigma-Aldrich) overnight to remove excess palladium, before purifying by preparative reverse-phase HPLC. $^1$H NMR (CDCl$_3$, 400 MHz) δ 8.25 (d, J=8.3 Hz, 2H), 7.68 (d, J=8.3 Hz, 2H), 7.25 (d, 8.45 Hz, 2H), 7.16 (d, J=8.45 Hz, 2H), 6.92 (m, 1H), 2.74 (s, 3H), 2.54 (m, 2H), 2.28 (m, 2H), 1.77 (m, 2H), 1.70 (m, 2H). HRMS [M+1]$^+$ Calculated: 430.0697, Measured: 430.0706.

Example C6.2

4-{5-[(4-Chlorophenyl)sulfanyl]-4-[4-(methylsulfinyl)phenyl]-1,3-oxazol-2-yl}cyclohex-3-en-1-ol

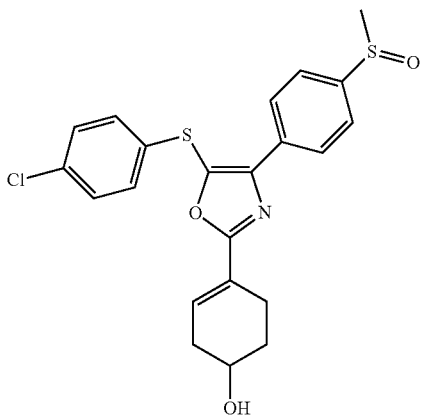 [SMILES: CS(=O)c1ccc(-c2nc(C3=CCC(O)CC3)oc2Sc2ccc(Cl)cc2)cc1]

The product was prepared in the manner of example C6.1 using 4-(4,4,5,5-tetramethyl-1,3,2-dioxaborolan-2-yl)cyclohex-3-en-1-ol. $^1$H NMR (DMSO-d, 500 MHz) δ 8.17 (d, J=8.53, 2H), 7.78 (d, J=8.53, 2H), 7.43 (d, J=8.60 Hz, 2H), 7.27 (d, J=8.60, 2H), 6.76 (m, 1H), 3.84 (m, 1H), 2.76 (s, 3H), 2.63 (m, 2H), 2.12 (m, 2H), 1.85 (m, 2H). HRMS [M+1]+ Calculated: 446.0646, Measured: 446.0669.

| Ex # | Structure | IUPAC name | M + 1 |
|---|---|---|---|
| C6.1 | 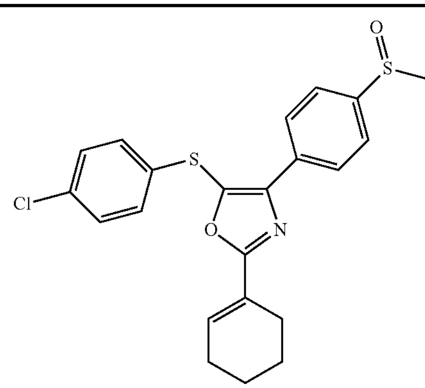 | 5-[(4-chlorophenyl)sulfanyl]-2-(cyclohex-1-en-1-yl)-4-[4-(methylsulfinyl)phenyl]-1,3-oxazole | 430.1 |

| Ex # | Structure | IUPAC name | M + 1 |
|---|---|---|---|
| B6.2 | 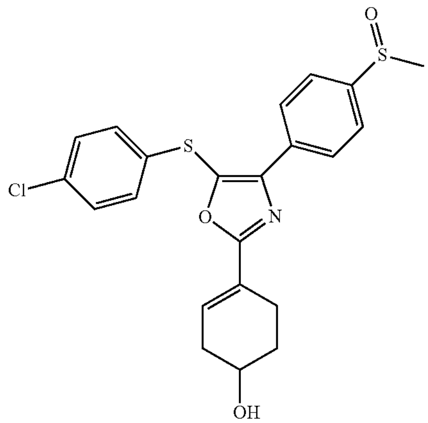 [SMILES: CS(=O)c1ccc(-c2nc(C3=CCC(O)CC3)oc2Sc2ccc(Cl)cc2)cc1] | 4-{5-[(4-chlorophenyl)sulfanyl]-4-[4-(methylsulfinyl)phenyl]-1,3-oxazol-2-yl}cyclohex-3-en-1-ol | 446.1 |
| B6.3 | 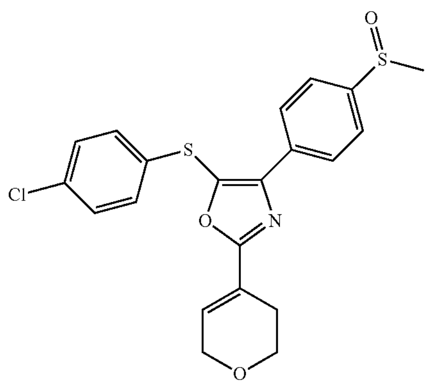 [SMILES: CS(=O)c1ccc(-c2nc(C3=CCOCC3)oc2Sc2ccc(Cl)cc2)cc1] | 5-[(4-chlorophenyl)sulfanyl]-2-(3,6-dihydro-2H-pyran-4-yl)-4-[4-(methylsulfinyl)phenyl]-1,3-oxazole | 432.3 |

What is claimed is:

1. A compound of the Formula

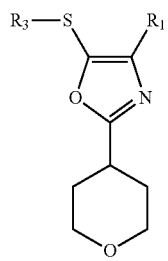

Ib wherein:

n is 0, 1 or 2, and

R$_1$ is selected from the group consisting of:

(1) phenyl, and (2) pyridyl, optionally mono or di-substituted with substituents R$^4$ and R$^5$, which are independently selected from the group consisting of (a) mono, di or tri-halo C$_{1-4}$ alkyl, (b) —C$_{1-4}$alkyl optionally substituted with one or two substituents selected from hydroxyl, —CHF$_2$ and —CF$_3$, (c) —S(O)$_n$C$_{1-4}$alkyl, (d) —C(O)—NR$^{10}$R$^{11}$, wherein R$^{10}$ and R$^{11}$ are each independently selected from H and C$_{1-4}$alkyl, (e) HET$^2$, wherein HET$^2$ is a 5 to 10-membered aromatic, partially aromatic or non-aromatic mono- or bicyclic ring, or N-oxide thereof, said containing 1 to 4 heteroatoms selected from O, S and N, and optionally mono or di-substituted with substituents selected from:

(1) halo, (2) —OH, (3) —C$_{1-4}$alkyl optionally substituted with hydroxy, halo or cyano, (4) —CF$_3$, (5) —OC$_{1-4}$alkyl optionally substituted with hydroxyl or halo, and (6) —C(O)O—C$_{1-3}$alkyl; and R$_3$ is selected from the group consisting of:

(1) phenyl, and (3) pyridyl, wherein R$_3$ is optionally mono or di-substituted with halo, haloC$_{1-4}$alkyl, or —OC$_{1-4}$alkyl optionally substituted with halo.

2. A compound selected from the group consisting of

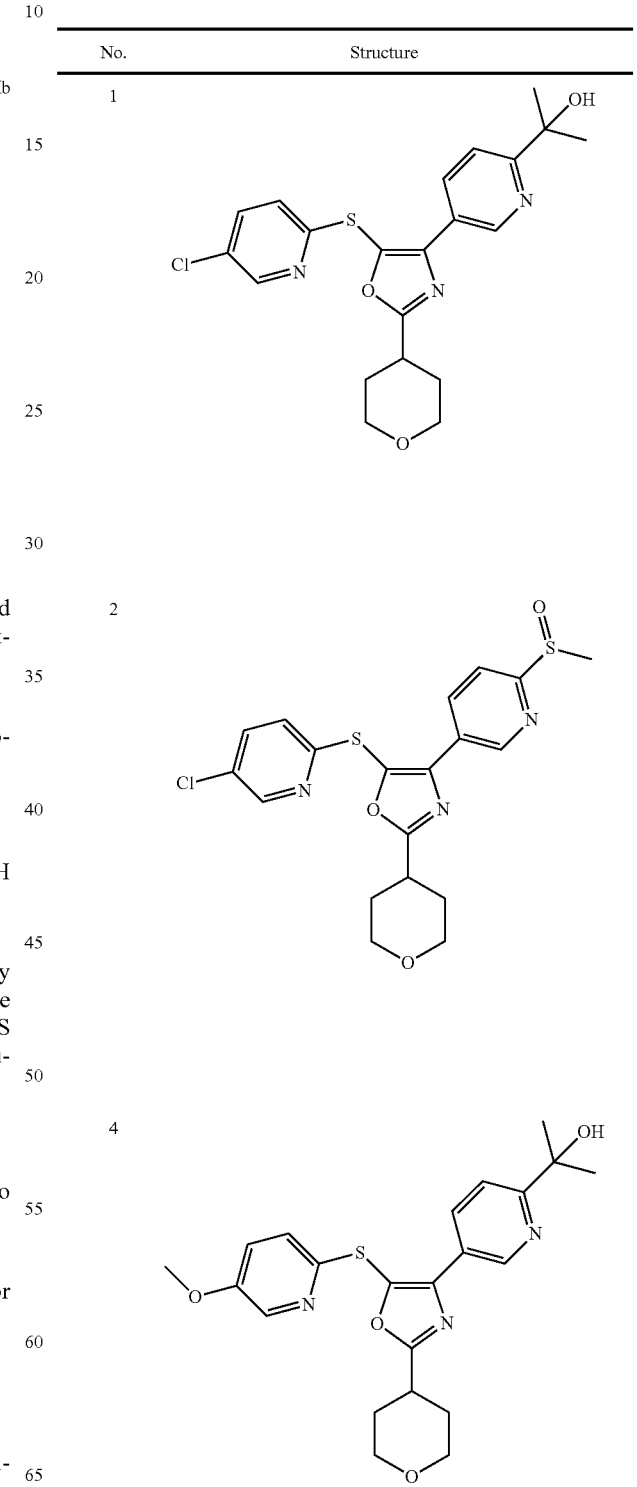

| No. | Structure |
|---|---|
| 5 | 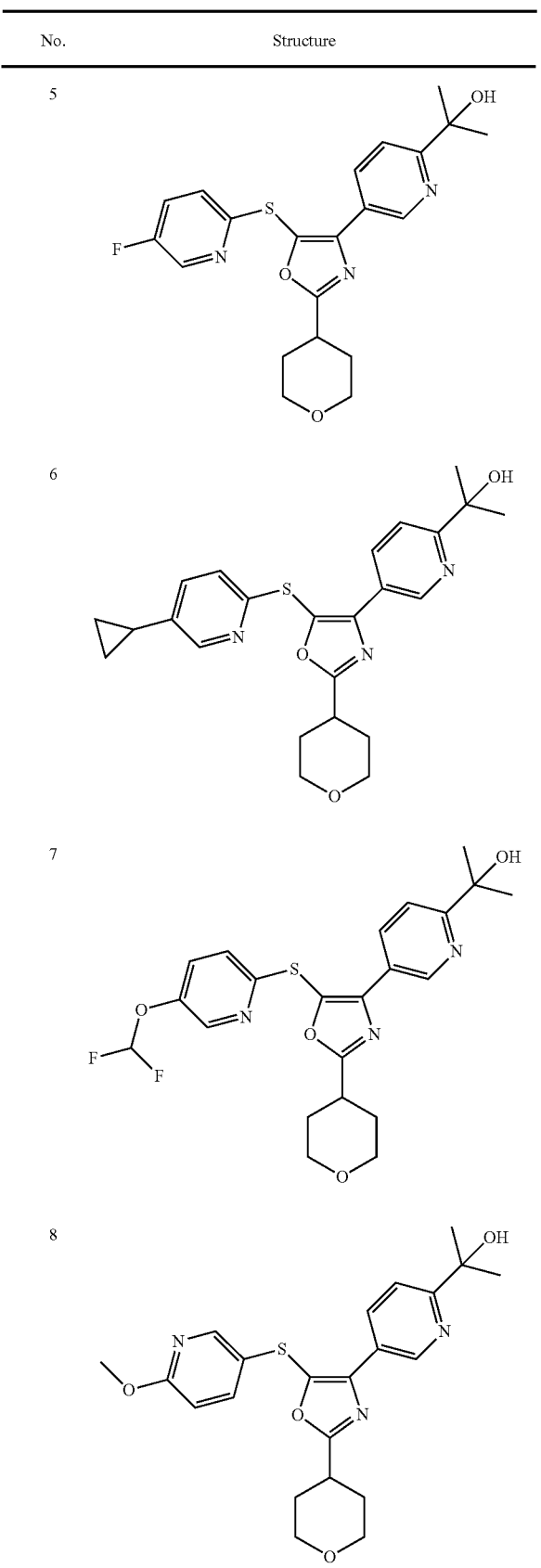 |
| 6 | |
| 7 | |
| 8 | |
| No. | Structure |
|---|---|
| 9 | 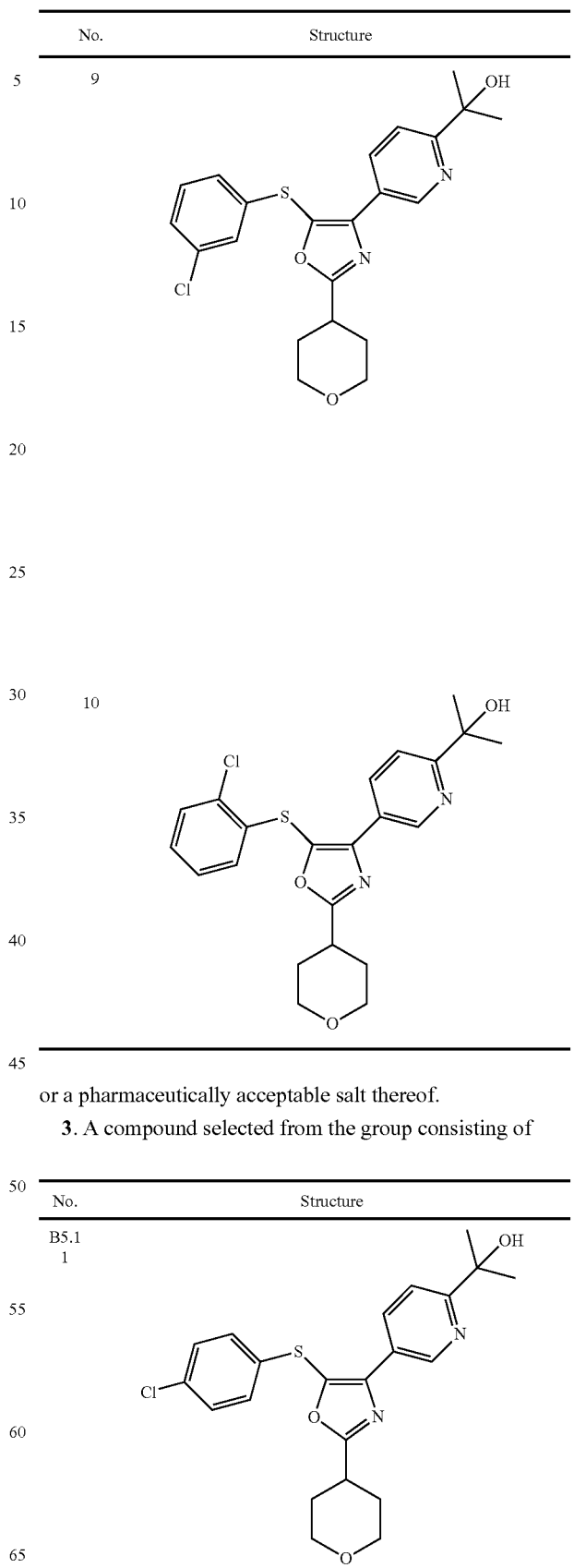 |
| 10 | |
or a pharmaceutically acceptable salt thereof.
3. A compound selected from the group consisting of
| No. | Structure |
|---|---|
| B5.1.1 |  |

-continued

| No. | Structure |
|---|---|
| B5.3.3 | |
| 9 | |
| 14 | |
| 16 | 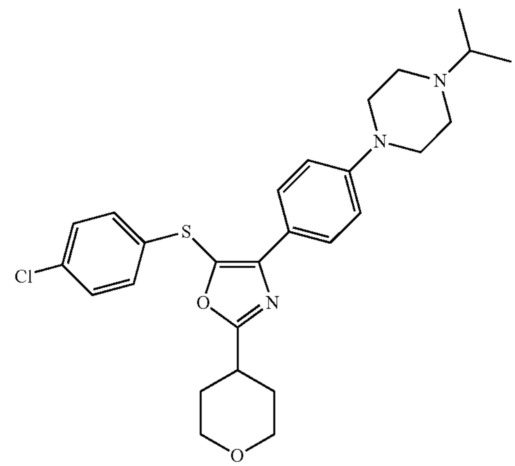 [SMILES: CC(C)N1CCN(c2ccc(-c3nc(C4CCOCC4)oc3Sc3ccc(Cl)cc3)cc2)CC1] |
| 17 | 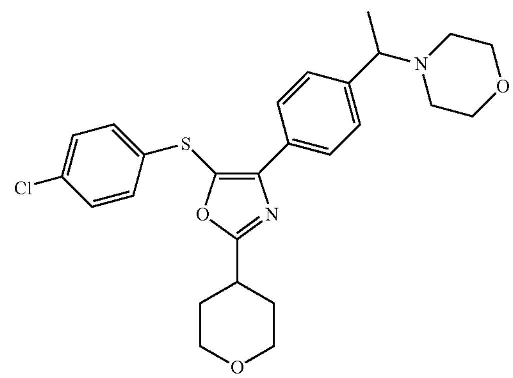 [SMILES: CC(c1ccc(-c2nc(C3CCOCC3)oc2Sc2ccc(Cl)cc2)cc1)N1CCOCC1] |
| 18 | 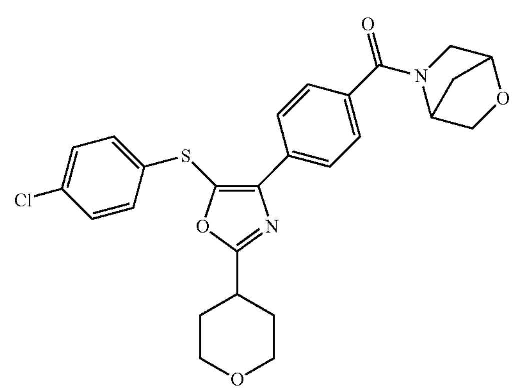 [SMILES: O=C(c1ccc(-c2nc(C3CCOCC3)oc2Sc2ccc(Cl)cc2)cc1)N1CC2CC1CO2] |
| 19 | 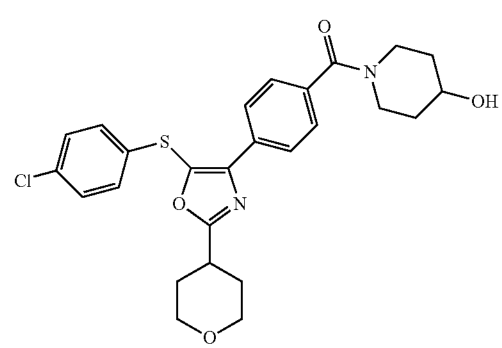 [SMILES: O=C(c1ccc(-c2nc(C3CCOCC3)oc2Sc2ccc(Cl)cc2)cc1)N1CCC(O)CC1] |

| No. | Structure |
|---|---|
| 20 | 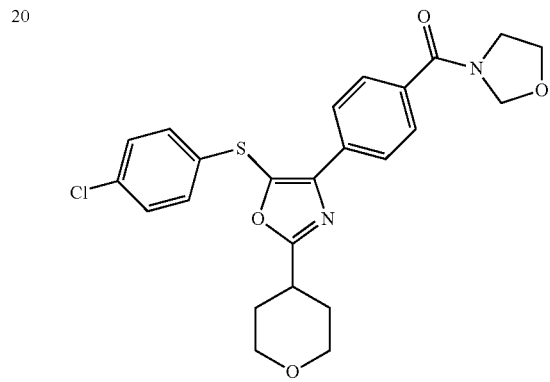 |
| 21 | 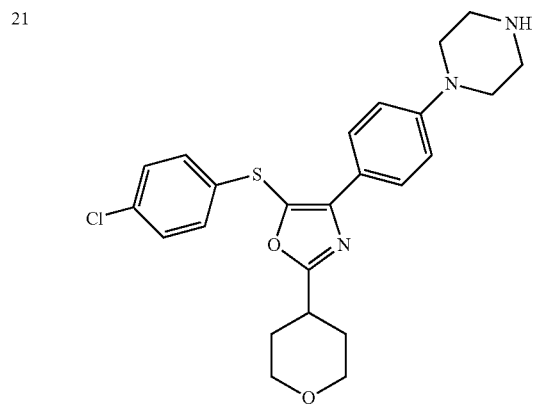 |
| 22 | 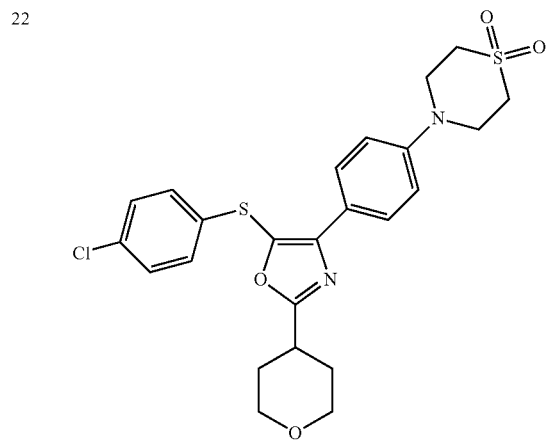 |
| 24 | 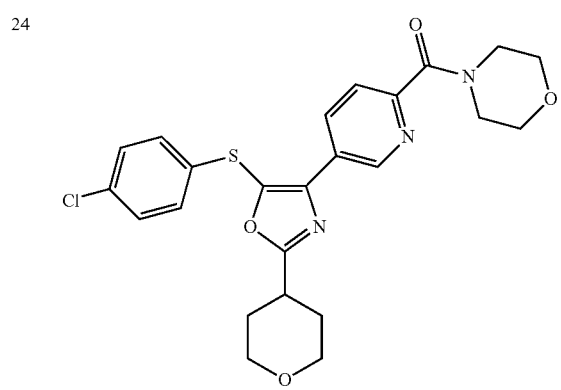 |
| No. | Structure |
|---|---|
| 26 | 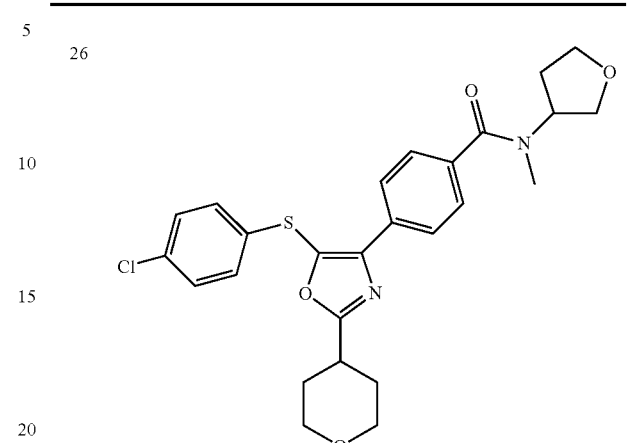 |
| 27 | 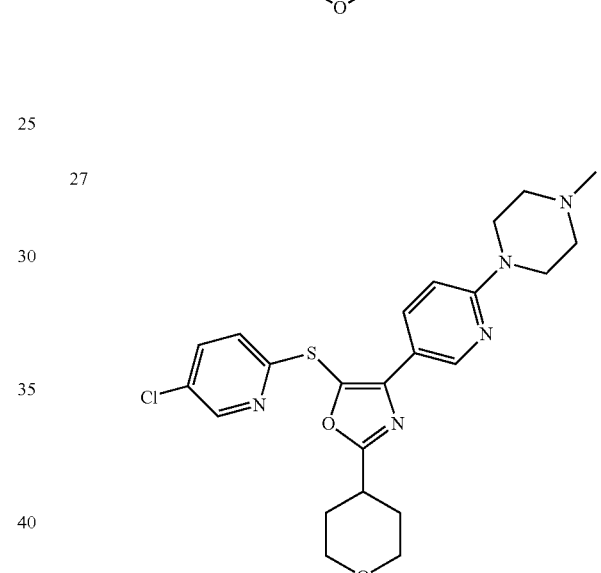 |
| 28 | 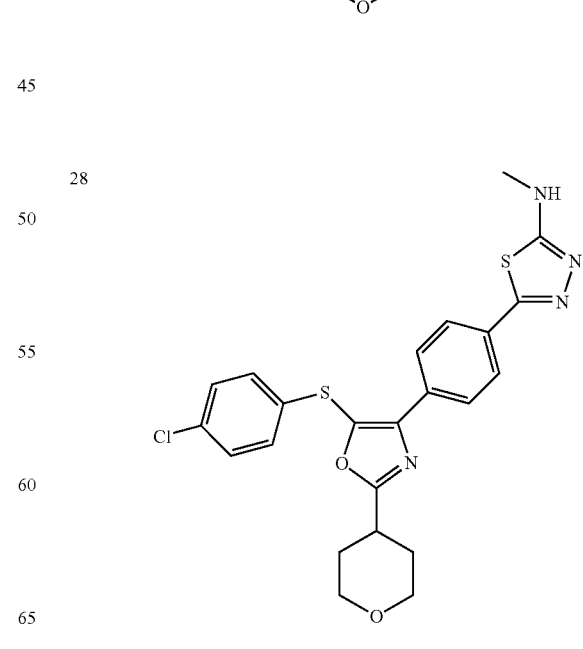 |

| No. | Structure |
|---|---|
| 29 | 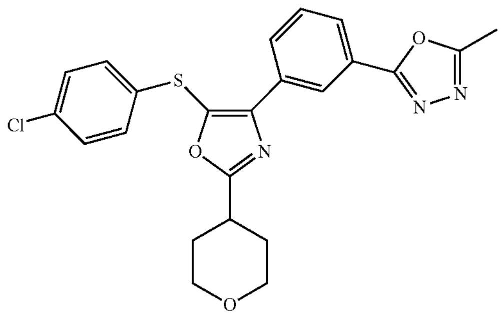 [SMILES: Cc1nnc(-c2cccc(-c3nc(C4CCOCC4)oc3Sc3ccc(Cl)cc3)c2)o1] |
| 30 | 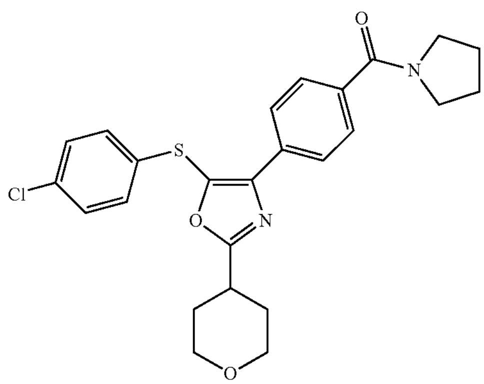 [SMILES: O=C(c1ccc(-c2nc(C3CCOCC3)oc2Sc2ccc(Cl)cc2)cc1)N1CCCC1] |

| No. | Structure |
|---|---|
| 31 | |
| 32 | | or a pharmaceutically acceptable salt thereof.

4. A pharmaceutical composition which comprises an inert carrier and a compound of claim 1 or a pharmaceutically acceptable salt thereof.

* * * * *